United States Patent
Richardson et al.

(10) Patent No.: US 7,060,295 B2
(45) Date of Patent: Jun. 13, 2006

(54) FORMULATIONS FOR THE PREVENTION AND TREATMENT OF INSULIN RESISTANCE AND TYPE 2 DIABETES MELLITUS

(75) Inventors: Kenneth T. Richardson, Anchorage, AK (US); Don C. Pearson, Lakewood, WA (US)

(73) Assignee: ChronoRX LLC, Anchorage, AK (US)

( * ) Notice: Subject to any disclaimer, the term of this patent is extended or adjusted under 35 U.S.C. 154(b) by 447 days.

(21) Appl. No.: 10/630,436

(22) Filed: Jul. 30, 2003

(65) Prior Publication Data

US 2004/0034030 A1    Feb. 19, 2004

Related U.S. Application Data

(62) Division of application No. 10/033,730, filed on Nov. 2, 2001, now Pat. No. 6,689,385.

(60) Provisional application No. 60/256,033, filed on Dec. 13, 2000, provisional application No. 60/245,471, filed on Nov. 3, 2000, provisional application No. 60/245,950, filed on Nov. 3, 2000.

(51) Int. Cl.
  *A61K 9/20* (2006.01)
  *A61K 9/48* (2006.01)
  *A61K 9/24* (2006.01)
  *A61K 9/32* (2006.01)
  *A61K 9/14* (2006.01)

(52) U.S. Cl. ............ 424/464; 424/451; 424/472; 424/482; 424/486; 424/489; 514/251

(58) Field of Classification Search ........... 424/464, 424/451, 472, 482, 486, 489; 514/251
  See application file for complete search history.

(56) References Cited

U.S. PATENT DOCUMENTS 6,207,190 B1 *    3/2001    Richardson et al.

* cited by examiner

*Primary Examiner*—Thurman K. Page
*Assistant Examiner*—Humera N. Sheikh
(74) *Attorney, Agent, or Firm*—M. Henry Heines; Townsend and Townsend and Crew, LLP

(57) ABSTRACT

The compositions and dosage forms of the invention are clinically useful as methods for increasing the effectiveness, efficiency and safety of biguanides (metformin) and/or sulfonylureas in the prevention and treatment of insulin resistance and diabetes mellitus, alone or in combination, as a nutrient for humans. The carefully chosen active ingredients of the invention are designed in a modular fashion to prevent and rectify adverse events associated with insulin resistance syndrome and diabetes mellitus, and with the clinical use of biguanides (metformin) and/or the sulfonylureas. These modules are: (1) Mitochondrial Metabolic Group, (2) Plasma and Mitochondrial Membrane Integrity Group, (3) Nocturnal Group and, (4) Insulin Alternative Group. When used in concert with a biguanide, a sulfonylurea or with a combination of both, the invention will broaden the clinical usefulness of these drugs. The invention will retard the progression of insulin resistance to type 2 diabetes, and reduce the serious microvascular and macrovascular complications commonly associated with insulin resistance syndrome and diabetes mellitus.

78 Claims, No Drawings

FORMULATIONS FOR THE PREVENTION AND TREATMENT OF INSULIN RESISTANCE AND TYPE 2 DIABETES MELLITUS

CROSS-REFERENCE TO RELATED APPLICATIONS

This application is a divisional of Ser. No. 10/033,730 filed Nov. 2, 2001, now U.S. Pat. No. 6,689,385.

This application is related to U.S. provisional patent applications Nos. 60/245,471, filed Nov. 3, 2000, 60/245,950, also filed Nov. 3, 2000, and 60/256,033, filed Dec. 13, 2000, all three of which are incorporated herein by reference in their entirety. The present application claims benefits from all three such provisional patent applications for all purposes legally capable of being served thereby.

BACKGROUND OF THE INVENTION

1. Field of the Invention

This invention is in the field of pharmacology, and relates to single-component or multi-component formulations used to enhance the efficiency and safety in the clinical use of the biguanide metformin, the sulfonylureas or combinations of sulfonylurea-metformin, in the pharmacological treatment of insulin resistance and type 2 diabetes mellitus.

2. Description of the Prior Art

Insulin resistance and non-insulin-dependent diabetes are prevalent in up to 35% of the population depending upon the age and nature of the subset. In the United States alone, 16 million people have type 2 diabetes and 13 million have impaired glucose tolerance. In fact type 2 diabetes has reached epidemic proportions worldwide. By 2025, an estimated 300 million people will have diabetes, most of whom will inhabit China, India, and the United States. Because of an aging and increasingly sedentary, obese population with changing, unhealthy diets, insulin resistance is also increasing alarmingly (it is already two to three times more prevalent than type 2 diabetes). This apparent increase in the prevalence of insulin resistance and type 2 diabetes occurs in all ethnic populations, but especially in those that have migrated from their native lands to more urbanized and westernized regions of the world.

Insulin resistance and type 2 diabetes exist not merely as part of the aging process, but also as a process that advances aging. Diabetes affects metabolism in totality: carbohydrate, lipid and protein. Its causes and its management are very, very complex and strikingly nonlinear.

Patients with diabetes of all types have considerable morbidity and mortality from microvascular (retinopathy, neuropathy, nephropathy) and macrovascular (heart attacks, stroke, peripheral vascular disease) pathology, all of which carry an enormous cost. For example: a) Proliferative retinopathy (the leading cause of blindness in the United States) and/or macular edema occur in about 50% of patients with type 2 diabetes, as do peripheral and/or autonomic neuropathy. b) The incidence of diabetic renal disease is 10% to 50% depending on ethnicity. c) Diabetics have heart attacks, strokes and peripheral vascular disease at about triple the rate of non-diabetics. The cost of treating diabetes and its complications exceeds $100 billion annually. In addition to these dreadful data, insulin resistance (a prelude to type 2 diabetes in about 50% of those effected) with its associated hypertension, coagulopathy, dyslipidemia and obesity substantially adds to these morbidity, mortality and cost statistics.

There are two clinical forms of diabetes, each with a different pathogenesis: type 1, insulin dependent diabetes mellitus and type 2, non-insulin dependent diabetes mellitus. The latter represents 90% of all diabetics. In type 2 diabetes, cellular resistance to the functional effectiveness of insulin results in above normal levels of insulin secretion. When this compensatory increase of insulin production cannot be maintained, and/or when cellular insulin resistance increases further, blood sugar rises, lipid and protein metabolism are disturbed, and the insidious processes of vascular complications of long-term diabetes begin.

The fasting hyperglycemia of type 2 diabetes exists in the presence of hyperinsulinemia; this reflects the presence of insulin resistance in the liver with resultant glycogenolysis and gluconeogenesis. In addition to the impaired insulin suppression of hepatic glucose production, a decrease of insulin-mediated glucose uptake by muscle cells contributes (about 50%) to the resultant hyperglycemia.

After ingestion of glucose, the maintenance of normal blood sugar therefore depends upon: 1) stimulation of insulin secretion; 2) insulin-mediated suppression of hepatic glycogenolytic and gluconeogenic glucose production, and 3) insulin-mediated glucose uptake by muscle. Although hyperglycemia has an independent, direct effect in suppressing hepatic gluconeogenesis and stimulating muscle glucose uptake, these effects are modest compared to those of insulin and are inadequate to compensate for the countering effects of insulin resistance.

The congeries of micro and macro pathologies from hyperinsulinemia and/or hyperglycemia have as causative mechanisms: free radical damage, nonenzymatic protein glycation, lipoprotein disturbances, disturbances of physiological NO effects, reduced synthesis of heparan sulfate and disorders of sorbitol and myoinositol metabolism.

Free radical generation and induced nitric oxide synthase (iNOS) production secondary to the hyperglycemia of type 2 diabetes can lead to pancreatic β-cell destruction, and the production of diagnostic enzymatic indicators characteristic of type 1 diabetes. This fact has introduced the term "type 1.5 diabetes". In this scenario, β-cells are not only "exhausted" by the progression of pathology from insulin resistance to type 2 diabetes, but may also undergo destruction induced by chronic hyperglycemia.

Hypertension, dyslipidemia, coagulopathy, obesity and development of type 2 diabetes—all of which may follow chronic insulin resistance—are largely preventable, as are the eventual diabetic micro- and macrovascular complications. In those patients with insulin resistance who do progress to type 2 diabetes, successful treatment requires maintenance of blood glucose at a normal preprandial level (or at a postprandial level below 180 dl) and a hemoglobin A1c level below 7.0%. This degree of glucose control is often not consistently attainable over long periods of time.

Likewise, good glycemic control avoids the impaired synthesis of the basement membrane proteoglycan, heparan sulfate, which accompanies hyperglycemia. Heparan sulfate is an essential component of the basement membrane of many cells. Most importantly, it supports many of the normal functions of endothelial cells by maintaining the integrity of the basement membrane and its anionic charge, both of which are critical in maintaining physiologic membrane impermeability: It is the predominant glycosaminoglycan produced by the glomerular epithelial cells. Microproteinuria, due to its inadequacy in the glomerular basement membrane, is one of the earliest, most consistent early signs of diabetes, and diabetic nephropathy is invariably associated with progressive proteinuria. Reductions of heparan sulfate in the basement membrane of retinal and renal capillaries also leads to the increased capillary permeability that occurs at both sites significantly contributing to diabetic retinopathy and nephropathy.

Glucose tolerance declines with age because of: 1) increased cell receptor resistance to insulin; 2) intracellular post receptor disturbances and 3) diminished pancreatic islet β-cell sensitivity to insulin and glucose. Insulin resistance, with secondary hyperinsulinemia and/or hyperglycemia, contributes to many disorders associated with aging, i.e., hypertension, obesity, atherosclerosis, lipid abnormalities, coagulopathies and chronic metabolic—perturbations including type 2 diabetes.

Although insulin resistance and type 2 diabetes each have an inherited pathogenic component, they both are substantially influenced by inappropriate diet and inadequate exercise.

In aging, as in diabetes, elevated circulating glucose reacts nonenzymatically with proteins and nucleic acids to form products that: 1) disturb the functionality of the cellular phospholipid membrane; 2) diminish tissue elasticity and 3) secondary to free radical formation, increase lipid peroxidation.

The ingestion of sugars, fats, and sodium have been linked to insulin resistance, while caloric restriction, exercise, ingestion of chromium, vanadium, magnesium, and certain antioxidants are associated with greater insulin sensitivity. Lifespan may favorably be affected, and the incidence of many chronic disorders commonly associated both with aging and with diabetes can be reduced, by manipulating the diet and its influence upon the glucose/insulin system.

Diabetes—Pertinent Anatomy and Physiology of Glucose Metabolism

The pancreas functionally integrates its exocrine and endocrine domains to modulate the kinetics and dynamics of intermediary metabolism:

1. Exocrine acinar cells produce amylase, which breaks down complex carbohydrates to monosaccharides in the intestine for absorption.
2. Endocrine islet α- and β-cells produce insulin, glucagon and somatostatin which regulate glucose production and utilization.

Glucose homeostasis requires a modulated endocrine system capable of controlling glucose flux into and out of the extracellular space. Insulin (β-cells) and glucagon (α-cells) must maintain a balance between glucose production, intracellular translocation and glucose utilization in the liver, adipose, muscle and neuronal tissue.

Failure of this integration between the exocrine and endocrine pancreatic functions is evident in diabetics: there is a loss of autocorrection—i.e., although exocrine acinar amylase mRNA may decrease, endocrine-produced insulin normally reverses this, causing a corrective increase in acinar mRNA and amylase production.

Insulin

Insulin is synthesized from a very large physiologically inactive polypeptide, proinsulin, which is derived from a still larger polypeptide, preproinsulin. Insulin itself is a large, dual-chain polypeptide with, respectively, 21 and 30 amino acids in the A and B chains. The A and B chains of the dimer are linked by disulfide bonds and then complexed with zinc ($Zn^{2+}$) for storage in the pancreatic β-cells.

Insulin is released from β-cells in response to elevated glucose levels. Under conditions of marked hyperglycemia, proinsulin is released in addition to insulin. Because of its slower disappearance, proinsulin may represent as much as 50% of the measured circulating "insulin" in persons with hyperglycemia. If hyperglycemia is sustained, the continued overproduction of inactive proinsulin may exhaust β-cells as they attempt to respond. This ultimately results in reduced insulin production. Moreover, the "numbing" (or progressive reduction in the response) of β-cells to the small amount of insulin that is present may ultimately lead to clinically overt type 2 diabetes and its more serious, often devastating complications. (See below.)

In addition to maintaining glucose translocation into cells, insulin stimulates cellular uptake of potassium and ascorbate. Thus, when combined with the usually existing $Mg^{2+}$ inadequacy of diabetes, insulin deficiencies exaggerate or cause hypertension, reductions in available circulating ascorbate and the "tissue scurvy" commonly associated with type 2 diabetes. This ascorbate deficit in turn contributes to the hypertension of insulin resistance and diabetes by reducing available BH4, the cofactor essential for endothelial nitric-oxide synthase (eNOS) activity, which maintains physiological vasodilatation.

Caveolar Insulin Transport

Most hydrophilic cell signaling substances like insulin have difficulty crossing cell membranes to institute intracellular effects. Instead, signal transduction to the inside of the cell occurs at caveolae—clusters of receptors located in specialized areas of the cell membrane. Caveolae, in fact, are membrane systems responsible for signal transduction and facilitating the integration of nutritional, mechanical and humoral information at the cell surface. Rich in phospholipids, cholesterol and lipid-anchored membrane proteins, they present as coherent patches immersed in the lipid bilayer, like floating rafts in the sea. Resident molecules move through endocytotic/exocytotic caveolar compartments. Caveolae and other similarly functional glycolipid rafts are especially abundant in the cellular membranes of insulin-sensitive cells.

Although many different signaling molecules may be available, the caveolae are the major sites for the integration of cellular signalling—"integration" in this context refers to the interplay of two or more signaling processes that result in reciprocal modulation. In the treatment of type 2 diabetes, the ability of caveolae to sequester molecules provides a target for influencing both imported and locally produced molecules in the modulation of cellular signaling.

Within caveolae, glycosylphosphatidylinositol (GPI) proteins transfer information between different membrane compartments. In particular caveolin-1, an insulin receptor, interacts with these GPI proteins permitting insulin translocation. (See GLUT4, below.)

Three types of receptor proteins are located within the caveolae of cell membranes:

Type I receptors have enzyme activity and usually possess an intracellular phosphotyrosine kinase (PTK) domain. Once the domain is activated by a ligand, e.g., insulin, PTK phosphorylates the intracellular tyrosine present in multiple proteins. These proteins then bind to phosphorylated tyrosine receptors of caveolin-1 (either to the insulin receptor itself or complexed with it) and a cascade of signalling proceeds to other parts of the cell.

Type II receptors are ion channels. Here, binding with a ligand, e.g., acetylcholine, causes rapid opening of an ion channel within the membrane protein permitting passage of selected ions: $Na^+$, $K^+$ or $Cl^-$.

Type III receptors as a class are referred to as G (guanine nucleotide) proteins. These are 7-helix transmembrane proteins that transfer their signal via a complex intracellular second messenger system. These receptors only recently have had their structure completely defined.

Once insulin is bound to Type I caveolin-1 receptors and initiates phosphorylation of the intracellular tyrosine domain, the resulting phosphorylation cascade activates GLUT4 vesicles. These fuse to the plasma membrane and proceed to translocate glucose into the cell. This activation and fusion require interaction between GLUT4 vesicle protein and cell membrane protein Syntaxin 4 (S4). As long as S4 is complexed with the cell membrane protein Synip, GLUT4 vesicles are inactive. Insulin dissociates the Synip:S4 complex, frees S4 to bind with GLUT4 vesicles and vesicle translocation of glucose into the cell becomes possible. Synip is the primary insulin regulated protein directly involved in glucose transport and GLUT4 vesicle translocation. It should be noted here that the antihyperglycemic effect of the trace element vanadium may in part be due to direct activation of the insulin receptor and in part to a prolongation of the action of insulin, possibly by inhibiting the formation of this Synip:S4 complex.

Apparently complex spatial compartmentalization is involved in the specificity of insulin action. As examples:

Once it is complexed, the insulin-activated receptor (caveolin-1) within the caveola is itself translocated endocytotically into the cytoplasm where its passenger insulin is released.

In addition to dissociating the Synip:S4 complex, insulin also activates "protein targeting for glycogen" (PTG) which forms a distinct insulin pool of protein phosphatase 1 (PP1). This is complexed with enzymes regulating a dephosphorylation cascade leading to the production and storage of glycogen. The insulin receptor is then exocytotically translocated to a position within a caveola of the cell membrane, under control of a feedback mechanism.

Caveolae are sensitive to lipids, especially cholesterol, and contain receptors that bind HDL, LDL and oxidized lipoproteins (oxLDL). The presence of elevated levels of oxLDL adersely affect caveolar efficiencies. (See, below.)

Disruption of these functions can have unexpected consequences given their involvement not only in insulin cell signaling but also in calcium ($Ca^{2+}$) metabolism, blood clotting and cholesterol transport.

Confounding any understanding of these already intricate, interrelated facets of insulin functionality are the varieties of its actions according to cell type, dosage, time of dosage and the presence of other hormones. And to make things even more complicated, insulin may initiate either phosphorylation or dephosphorylation cascades within the cell. Although the insulin receptor itself is phosphorylated in its tyrosine domain (as noted above), the subsequent changes in protein phosphorylation occur predominantly on serine and threonine residues and, in addition, L-arginine supports ligand binding to phosphotyrosine receptors, including the insulin receptor.

Many steps in these phosphorylation cascades involve ATPase, which is dependent on $Mg^{2+}$ as a cofactor. $Mg^{2+}$ deficiency is sufficiently common in diabetics that its oral supplementation is recommended by the American Diabetes Association for diabetics with normal renal function.

OxLDL (which is increased by hyperinsulinemia and hyperglycemia) displaces cholesterol from the caveolae, driving eNOS from caveolae and impairing its activation: vasoconstriction and increased coaguability arise from this destabilization of the physiological balance between the vasodilation of NO, the vasoconstriction of ET-1 and the availability of cGMP. Although HDL helpfully reduces the ability of oxLDL to decrease eNOS activation(and thus preserve subcellular levels of eNOS and indirectly NO), the level of HDL is reduced in patients with insulin resistance.

Mitochondria and Pancreatic β-Cell Apoptosis

Pancreatic β-cell apoptosis is responsible for irreversible progression toward insulin dependence in type 2 diabetes.

Apoptosis is an enzyme-driven catabolic cell-death process. Activation of endonucleases and specific proteases (caspases) occurs when mitochondria make a "decision to die". Inhibition of endonucleases and caspases do not prevent apoptosis, indicating that that the "decision to die" is taken before catabolic enzymes are activated and that the activation of these enzymes is by-product of the cell-death process and not a regulatory event.

The sequence leading to apoptosis is: 1) A pre-mitochondrial (induction) phase, in which numerous physiological and some pathological stimuli trigger an increase in mitochondrial membrane permeability (e.g., prooxidants, increased cytosolic $Ca^{2+}$, induced NO). 2) A mitochondrial (effector) phase during which mitochondrial membrane integrity is lost and the "decision to die" is made. 3) A post-mitochondrial (degradation) phase during which intermembrane proteins (e.g., cytochrome C, apoptosis-inducing factor) are released which activate catabolic hydrolases (endonucleases, caspases) responsible for apoptotic degradation of essential proteins and nuclear DNA. This invention reduces the pathologic stimuli of the induction phase of apoptosis, including that of the β-cell.

Not unexpectedly, the complexity of the involved pathophysiologies defines their nonlinearity. This complexity also emphasizes the necessity for modulation at the many points of potential instability in these processes. The inadequacy or lack of such modulation at multiple points may eventually lead to overt type 2 diabetes itself. The identification and influence of these modulation points represent therapeutic opportunities and underly the rationale of this invention.

Pertinent Pathophysiology of Diabetic Mellitus

In normal subjects, after an overnight fast, glucose is produced from hepatic glycogen (25%) and gluconeogenesis (75%); the kidney in addition to the liver is capable of gluconeogenesis. The main gluconeogenic precursors for the liver are amino acids (predominantly alanine and glutamine derived from muscle protein) and glycerol from triglyceride hydrolysis in adipose tissue. Catecholamines stimulate gluconeogenesis, as does glucagon via cAMP, while cortisol has a delayed effect in causing hyperglycemia. Insulin opposes these gluconeogenic and glycogenolytic actions.

Hepatic glucose production can be autoregulated according to portal vein glucose levels, assuming there is a normal response to insulin.

As previously stated, the initial event in insulin action is its binding to an enzymatic caveolar receptor. This causes a conformational change in the intracellular tyrosine kinase domain of the receptor, its autophosphorylation and an intracellular phosphorylation cascade that mediates some of insulin's effects. After caveolin-1 binding occurs, the resulting insulin-receptor complex is internalized endocytotically and insulin dissociates intracellularly. Some residual receptors simply degrade, some pass to the Golgi apparatus to join others, newly synthesized, and are recycled exocytotically to a caveolar membrane region to await another insulin ligand.

In persistent hyperglycemia the turnover of receptor binding and internalization are increased resulting in a net reduction in the number of available receptors at the cell membrane (downregulation). As more and more receptors are occupied, adjacent unoccupied receptors become less receptive (negative co-operativity). Downregulation and negative co-operativity combine to decrease insulin effectiveness during sustained hyperinsulinemia. In short, sustained hyperinsulinemia results in decreased receptivity, increased insulin resistance.

Although circulating insulin levels are frequently elevated early in type 2 diabetes, a deficiency of intracellular insulin and increased cellular resistance to many of insulin's actions simultaneously occur: there is resistance to the stimulation of glucose uptake by muscle and liver, there is resistance to the suppression by insulin of hepatic glucose production, there is resistance to the suppression by insulin of lipolysis in adipose tissue, etc. Several possibilities for these inadequacies have been postulated: that there is some structural abnormality in the insulin receptor or in the region of the caveolin-1 insulin receptor which results in disruption of the intracellular phosphorylation cascade; or that there is an abnormality in the endocytotically intracellular insulin release effecting glycogenic enzymes; or that there is a Synip related effect. Again, the process is unclear, complex and nonlinear.

Recent research suggests that there is a high expression of the cytokine tumor necrosis factor-α (TNF-α) in the adipocytes of obese individuals, and that this TNF-α is a principal contributor to insulin resistance and its subsequent type 2 diabetes of obesity. TNF-α is an important regulator of the processes of apoptosis and thus modulates the volume of tumor, adipose and muscular tissues. It is produced not only by immunocompetent cells but also by adipocytes and muscle cells. This cytokine is activated in tumors and obesity, among other conditions. By acting on the phosphorylation of IRS-1 and PI-3 kinase, by modifying resistance through regulation of the synthesis of the insulin responsive glucose transporter GLUT4, and through interference with insulin signaling (perhaps via leptin), TNF-α promotes insulin resistance and anorexia.

Studies conducted on obese human patients have demonstrated a correlation between levels of TNF-α, the extent of obesity, as well as the level of hyperinsulinemia (results of a recent study are consistent with the hypothesis that TNF-α could be involved in the regulation of plasma leptin concentrations in obese subjects).

Irrespective of the cause, insulin resistance is associated with widespread and adverse effects on health. This is true even when glucose tolerance is only mildly impaired but not yet in the overt diabetic range. Notable among the adverse effects is the predisposition to vascular disease affecting large blood vessels and an association with hypertension and dyslipidemia (elevated triglycerides and decreased HDL). In fact, this combination of 1) glucose intolerance, 2) insulin resistance, 3) hypertension and 4) dyslipidemia is common enough to have acquired the name Syndrome X, the insulin resistance syndrome or Reaven's syndrome. Clinically it defines hundreds of millions of people worldwide.

It is clear that the process governing both insulin resistance and type 2 diabetes is diagrammically syncytial. It is not a linear, straightforward process that lends itself to a single treatment modality. Neither disease is a singularity and the pathophysiologic continuum of each is not rationally approachable with a pharmaceutical "silver bullet".

Aging and Diabetes Mellitus

With aging there is a gradual decline in glucose tolerance at least in part because of a progressively increased resistance to insulin at its receptor site and a decreased response by the pancreatic β-cells to glucose levels. In aging, similar to diabetes, the elevated circulating glucose secondary to increasing insulin resistance reacts nonenzymatically with proteins and nucleic acids to form products that disturb cell membrane function and diminish tissue elasticity. Also, these disturbances in glucose/insulin metabolism are associated with increased lipid peroxidation from elevated free radical formation resulting from the autooxidation of glucose. Augmented free radical formation and lipid peroxidation, common in diabetes mellitus, are associated with the "premature aging" of diabetic patients: Long term, excessive ingestion of sugars, fats and sodium have been linked to decreased insulin sensitivity, while caloric restriction, exercise, ingestion of chromium, vanadium, $Mg^{2+}$, certain free radical scavengers and nuclear factor kappa B (NFkappaB) inhibitors are associated with greater insulin sensitivity. Thus, manipulation of the diet by influencing the glucose/insulin system may favorably affect lifespan and reduce the incidence of the microvascular and macrovascular complications of type 2 diabetes.

Vascular Pathology

The earliest microvascular lesion of diabetes is a variable thickness of the basement membrane. A healthy basement membrane provides vascular stability and importantly, a permeability barrier. Cellular impermeability requires a negative electrical charge provided by heparan sulfate, a polyanionic proteoglycan. Sulfate groups provided by lipoic acid, n-acetylcysteine (NAC) and possibly taurine may contribute to the adequacy of this necessary negativity of the cell membrane. In diabetes both the basement membrane thickness and heparan sulfate levels are decreased. As a result, vessel permeability is increased. Increased vessel permeability is the most notable initial microvascular complication in diabetes.

Early in diabetes there are additional abnormal microvascular (arteriolar and capillary) dysfunctions; intraluminal pressure and flow are both increased. These, plus the increased permeability of the basement membrane and the associated vascular endothelial dysfunction, limit normal vascular autoregulatory mechanisms. This combination of failures leads to the familiar diabetic clinical manifestations of microvascular and macrovascular insufficiencies of the legs, feet, heart, eye and brain.

Microvascular Complications
1. Diabetic retinopathy is the leading cause of blindness in the working population.
2. Diabetic nephropathy is common in type 2 diabetes. Risk of death is increased 100 fold.
3. Diabetic neuropathy increases each decade to a 60% incidence after 25 years.

Macrovascular Complications
1. Cardiovascular risk of death is increased three fold.
2. Cerebrovascular risk of death is increased.
3. Amputation risk is increased five fold.

Biochemical Mechanisms of Diabetic Complications
Free Radical Damage
Release of cytochrome C from chromosomal mitochondria
Non-enzymatic glycation
Lipoprotein modifications
Disturbances of physiological NO effects
Sorbitol and myoinositol metabolism alteration
Interference with proteoglycans Although diabetes mellitus and insulin resistance are progressive, complex and frequently unpredictable processes with many points of potential instability, the latter are identifiable. To have any long-term chance of favorably influencing the cellular pathophysiology of insulin resistance and type 2 diabetes, any clinical approach must involve not only the coordination of life style modification, but also utilize finely calibrated combinations of pharmaceutical agents acting at multiple biomolecular nodes of modulation.

Therefore it is useful to consider, in turn, the pathologic states caused by insulin resistance and type 2 diabetes, the underlying molecular biologic defects or deficiencies, the existing modalities for favorably modulating these and the complementary, beneficial interactions of some of these approaches.

A. Pathologic States Caused by or Worsened by Insulin Resistance and/or Type 2 Diabetes
SPECIFIC: MICROVASCULAR COMPLICATIONS
  1. NEPHROPATHY
  2. NEUROPATHY
  3. RETINOPATHY
NON-SPECIFIC: MACROVASCULAR COMPLICATIONS
  1. ATHEROSCLEROIS
  2. HYPERTENSION
  3. CORONARY ARTERY DISEASE
  4. CEREBROVASCULAR DISEASE
  5. PERIPHERAL VASCULAR DISEASE
RELATED MORBIDITY
  1. OBESITY
  2. POOR RESISTANCE TO INFECTION
  3. PREMATURE AGING
  4. CATARACTS
  5. ALZHEIMER'S DISEASE (POSSIBLE)

B. Cellular Physiological and Molecular Biological Disturbances in Insulin Resistance and/or Type 2 Diabetes
1. INSULIN SENSITIVITY IS DECREASED
2. INSULIN RESISTANCE IS INCREASED
3. DURATION OF INSULIN ACTION IS DECREASED
4. HYPERINSULINEMIA
5. β-CELL INSULIN SECRETION IS INITIALLY INCREASED, THEN DECREASED
6. β-CELL DYSFUNCTIONAL APOPTOSIS
7. β-CELL SENSITIVITY IS DECREASED
8. HYPERGLYCEMIA
9. ADVANCED GLYCATION PRODUCTS (AGES) OCCUR
10. GLUCOSE AUTOOXIDATION OCCURS WITH FORMATION OF ROS (OXIDATIVE STRESS)
11. FREE RADICALS ARE INCREASED
12. GLUTATHIONE (GSH) EFFECTS ARE DECREASED
13. ENDOTHELIUM BECOMES DYSFUNCTIONAL
14. VASOCONSTRICTION IS INCREASED
15. DEFECTIVE ACETYLCHOLINE (ACH) RESPONSE→VASOCONSTRICTION
16. SYMPATHETIC NERVOUS SYSTEM ENHANCED: NOCTURNAL HEART RATE INCREASED
17. CALCIUM SIGNALING IS DISTURBED
18. REDUCED eNOS→IMPAIRED VASODILATION
19. ET-1 IS INCREASED WITH INTENSE, PROLONGED VASOCONSTRICTION
20. VASCULAR SMOOTH MUSCLE (VSMC) HYPERTROPHY RESULTS
21. VCAM-1 & ICAM-1 (VASCULAR ADHESION MOLECULES) INCREASE
22. DESTABILIZATION OF PLATELETS
23. REDUCED SYNTHESIS OF HEPARAN SULFATE WITH PROTEINURIA
24. SECONDARY ELEVATION OF HOMOCYSTEINE
25. HOMOCYSTEINE AGGRAVATION OF DIABETIC HYPERTENSION & ATHEROGENESIS
26. VITAMIN C→DEHYDRO ASCORBIC ACID (DHAA) IMBALANCE OCCURS
27. VITAMIN C MAY BECOME A PROOXIDANT
28. EXHAUSTION OF VITAMIN E
29. CELL MEMBRANE LIPID PEROXIDATION
30. DESTABILIZATION OF CELLULAR AND SERUM LIPIDS
31. DESTABILIZTION OF MEMBRANE CAVEOLAE
32. LDL OXIDATION
33. MACROPHAGE ACTIVITY INCREASED (FOAM CELL DEVELOPMENT)
34. ALDOSE REDUCTASE IS UNINHIBITED RESULTING IN INCREASED SORBITOL
35. POLYOL OSMOTIC EFFECT IS INCREASED
36. MYOINOSITOL AND TAURINE OSMOLAR EFFECTS ARE DISTURBED
37. STRUCTURAL AND FUNCTIONAL PERICYTE AND NEURONAL DISRUPTION
38. MICROVASCULAR BLOOD FLOW IS REDUCED
39. NERVE CONDUCTION VELOCITY IS DECREASED
40. HYPOMAGNESEMIA OCCURS, DECREASING INSULIN EFFECT→CELL MALFUNCTIONS
41. POSSIBLE DIABETIC ADVANCEMENT OF ALZHEIMER'S DISEASE Oral Hypoglycemic Agents—Aspects of Biochemistry There are various pharmacological approaches to improving glucose homeostasis, but those currently used in clinical practice either do not succeed in restoring normoglycemia in most patients, fail after a variable period of time, or have side effects that preclude their use in some patients. The components of this invention will improve the performance, duration of effectiveness and safety of therapies, which depend upon the inclusion of the biguanides (e.g., metformin), of the sulfonylureas (various), or of sulfonylurea-biguanide combinations.

For glycemic regulation, four classes of oral drugs are currently available: biguanides (e.g., metformin), sulfonylureas (e.g., tolbutamide, glyburide, glipizide and others), α-glucosidase inhibitors (e.g., acarbose and miglitol) and thiazolidinediones (e.g., troglitazone and rosiglitazone), each of these has a different mode and site of action.

This invention focuses on adjunctive therapy for patients using a biguanide, one of the sulfonylureas or the concurrent use of both ( i.e., a combination of sulfonylurea and biguanide) for treatment of progressive insulin resistance and type two diabetes.

The principle of long-term maintenance of glucose control applies to both progressive insulin resistance and type 2 diabetes. The treatment strategies while similar, are somewhat different. Progressive insulin resistance has as its central abnormality hyperinsulinemia. The latter persists as the disease progresses to type 2 diabetes with its central abnormality, hyperglycemia. In each case the process is nonlinear and its pharmacological modulation is complex.

A. Sulfonylureas

A.1. Sulfonylureas: Pharmacodynamics and Pharmacokinetics

The sulfonylurea group has dominated oral antidiabetic treatment for years. They primarily increase insulin secretion. Their action is initiated by binding to and closing a specific sulfonylurea receptor (an ATP-sensitive $K^+$ channel) on pancreatic β-cells. This closure decreases $K^+$ influx, leading to depolarization of the membrane and activation of a voltage-dependent $Ca^{2+}$ channel. The resulting increased Ca²⁺ flux into the β-cell, activates a cytoskeletal system that causes translocation of insulin to the cell surface and its extrusion by exocytosis.

The proximal step in this sulfonylurea signal transduction is the binding to (and closure) of high-affinity protein receptors in the β-cell membrane. There are both high and low-affinity sulfonylurea receptor populations. Sulfonylurea binding to the high-affinity sites affects primarily K(ATP) channel activity, while interaction with the low-affinity sites inhibits both Na/K-ATPase and K(ATP) channel activities. The potent second-generation sulfonylureas, glyburide and glipizide, are able to saturate receptors in low nM concentration ranges, whereas older, first-generation drugs bind to and saturate receptors in microM ranges.

The association of sulfonylurea receptors (SURs) with K(IR)6.x subunits to form ATP-sensitive K⁺ channels, presents perhaps the most unusual function known for members of the transport ATPase family. The integration of these two protein subunits extends well beyond conferring sensitivity to sulfonylureas. These SUR-K(IR)6.x interactions are critical for all of the properties associated with native K(ATP) channels including quality control over surface expression, channel kinetics, inhibition and stimulation by magnesium nucleotides and response both to channel blockers like sulfonylureas and to potassium channel openers. The K(ATP) channel is a unique example of the physiologic and medical importance of a transport ATPase and provides a paradigm for how other metallic members of the family may interact with other ion channels. This also speaks to the importance and the mechanism of modulation by Mg²⁺ of many aspects of membrane channel receptors.

The activity of ATP-sensitive K⁺ channels is also controlled by insulin secretagogues, by glucose and by certain amino acids such as cationic L-arginine and the non-polar, essential amino acid L-leucine. The amino acid secretagogues must be metabolized to inhibit the K⁺ channel activity and appear to do so by increasing the level of ATP, or by increasing the ATP/adenosine diphosphate (ADP) ratio. As a result, the increased availability of ATP reduces channel activity by binding to a specific site on the cytoplasmic surface of the receptor protein. To function as an insulin secretagogue, L-arginine requires adequate thiamine and L-leucine requires thiamine for its catabolic metabolism as well. This invention will enhance the effectiveness of sulfonylureas by supplying complementary amino acid secretagogues in a complementary milieu.

There is a synergy between the action of glucose and that of the sulfonylureas: sulfonylureas are better effectors of insulin secretion in the presence of glucose. For that reason, the higher the level of plasma glucose at the time of initiation of sulfonylurea treatment, the greater the reduction of hyperglycemia.

Exposure of perfused rat hearts to the second-generation sulfonylurea glyburide leads to a dramatic increase in glycolytic flux and lactate production. When insulin is included in the buffer, the response to glyburide is significantly increased. (Similarly, glyburide potentiates the metabolic effects of insulin.) Because glyburide does not promote glycogenolysis, this increase in glycolytic flux is caused solely by a rise in glucose utilization. Since the drug does not alter oxygen consumption, the contribution of glucose to overall ATP production rises while that of fatty acids falls. These metabolic changes aid the heart in resisting ischemic insults.

Insulin, on the other hand, is released by the pancreas into the portal vein, where the resultant hyperinsulinemia suppresses hepatic glucose production and the elevated level of arterial insulin enhances muscle glucose uptake, leading to a reduction in postprandial plasma glucose levels.

The initial hypoglycemic effect of sulfonylureas results from increased circulating insulin levels secondary to the stimulation of insulin release from pancreatic β-cells and, perhaps to a lesser extent, from a reduction in its hepatic clearance. Unfortunately, these initial increases in plasma insulin levels and β-cell responses to oral glucose are not sustained during chronic sulfonylurea therapy. After a few months, plasma insulin levels decline to those that existed before treatment, even though reduced glucose levels are maintained. Because of downregulation of β-cell membrane receptors for sulfonylurea, its chronic use results in a reduction in the insulin stimulation usually recorded following acute administration of these drugs. More globally, impairment of even proinsulin biosynthesis and, in some instances, inhibition of nutrient-stimulated insulin secretion may follow chronic (greater than several months) administration of any of the sulfonylureas. (However, the initial view that the proinsulin/insulin ratio is reduced by sulfonylurea treatment seems unlikely in light of recent research.) If chronic sulfonylurea therapy is discontinued, a more sensitive pancreatic β-cell responsiveness to acute administration of the drug is restored.

It is probable that this long-term sulfonylurea failure results from chronically lowered plasma glucose levels (and a resulting feedback reduction of sulfonylurea stimulation); it does, however, lead to a diminishment of the vicious hyperglycemia-hyperinsulinemia cycle of glucose toxicity. As a result, the sulfonylureas reduce nonenzymatic glycation of cellular proteins and the association of the latter with an increased generation of advanced glycation end products (AGEs), and improve insulin sensitivity at the target tissues. But, it should be kept in mind that one of these cellular proteins is insulin, which is readily glycated within pancreatic β-cells and under these conditions, when it is secreted it presumably is now ineffective as a ligand The formulations of this invention reduce protein glycation and will thereby increase the amount of secreted insulin that is effective at the target tissues.

It has been suggested that sulfonylureas may have a direct effect in reducing insulin resistance on peripheral tissues. However, most investigators believe that whatever small improvement in insulin action is observed during sulfonylurea treatment is indirect, possibly explained (as above) by the lessening of glucose toxicity and/or by decreasing the amount of ineffective, glycated insulin.

When sulfonylurea treatment is compared with insulin treatment it is found that: (1) treatment with sulfonylurea or insulin results in equal improvement in glycemia and insulin sensitivity, (2) the levels of proinsulin and plasminogen activator inhibitor-1 (PAI-1) antigen and its activity are higher with sulfonylurea, and (3) there are no differences in lipid concentrations between therapies.

Because sulfonylureas (glyburide) are weak acids they are more than 98% bound to albumin, but this does not appear to be influenced by the extent of albumin glycation.

A.2. Sulfonylurea: Effectiveness

The hypoglycemic potency of sulfonylureas is directly related to the starting fasting plasma glucose level. The higher the fasting plasma glucose level, the greater its decrease when treated with sulfonylureas. In the United States, the mean $HbA_{1C}$ value in diabetic patients is 10%, which corresponds to a fasting plasma glucose level of more than 200 mg/dL. In such patients treated with sulfonylureas, one can expect the fasting plasma glucose level to decrease by 60 to 70 mg/dL and the $HbA_{1C}$ value to decrease by 1.5 to 2.0 percentage points. Approximately 25% of type 2 diabetics treated with a sulfonylurea will achieve a fasting plasma glucose level lower than 140 mg/dL. However this also means that 75% will not reach this goal, and thus will require some type of additional therapy.

In some type 2 diabetics, autoantibodies to islet-cell cytoplasm (ICA) and glutamic acid decarboxylase (GADA) can occur. The phenotype of older adults is similar to type 2 diabetics without antibodies, and the occurrence of these antibodies predicts an increased likelihood of insulin treatment because of progressive β-cell loss. Signs of islet cell autoimmunity occur in 12% of type 2 diabetics over the age of 65.

In addition, there is an increase in fibrinogen (P=0.005) and C-reactive protein levels (P=0.025) in type 2 diabetic patients with autoantibodies. A pronounced activation of the acute-phase response, found to be associated with islet cell autoimmunity, may in part explain the associated defects in insulin secretion. This not only has direct implications for adequate classification and treatment of type 2 diabetes in the elderly, but also for understanding the autoimmune/inflammatory mechanisms involved in the pathogenesis of hyperglycemia.

By reducing dysfunctional β-cell apoptosis, this invention will enhance the effectiveness of sulfonylurea therapy by stopping or slowing the progression of type 2 diabetes toward this stage of progressive autoimmune/inflammatory β-cell destruction—sometimes referred to as "type 1.5" diabetes.

Of those patients who have a good initial response to sulfonylurea therapy, the secondary failure rate is about 5% to 7% per year. After 10 years this failure has mounted to over 50% and most sulfonylurea-treated patients require a second oral agent. Less than 20% of type 2 diabetics have satisfactory long-term therapy after 10 years of sulfonylurea treatment. First and second generation sulfonylureas are equally subject to secondary failure. Switching from a first to a second-generation sulfonylurea has been more or less equally "successful", but ultimately treatment is unsatisfactory. It is the intention of this invention to extend the duration of effect of sulfonylurea treatment of type 2 diabetes by delaying the onset, and slowing the progression, of β-cell dysfunction and inappropriate β-cell apoptosis.

All sulphonylureas fail at rates that are dependent both on the phenotype at presentation and (perhaps) on the agent used initially. Higher eventual failure rates are found in those with higher initial glucose concentrations, those who are younger, those with lower β-cell reserve and (in the UKPDS study) those randomized to second generation drugs, compared with first generation drugs. Prospective placebo-controlled trials have shown that second generation sulfonylureas (glipizide, glyburide, and glimepiride) exert equipotent glucose-lowering effects, but it is not known whether they also differ in their therapeutic end results.

Regarding the benefit of intensive therapy with sulfonylureas (chlorpropamide, glibenclamide) or with insulin in type 2 diabetes, the UKPDS interpreted their data to indicate that " . . . intensive blood glucose control by either of the sulphonylureas or by insulin, substantially decreases the risk of microvascular complications, but not macrovascular disease . . . ".

Management of patients with progressive insulin resistance and type 2 diabetes should focus on decreasing the excess macrovascular disease with which these are associated, as well as preventing or minimizing microvascular disease. As shown by the UKPDS data, near-normoglycemic control can reduce microvascular disease. However, this requires the concomitant management of the cardiovascular risk factors of the insulin resistance syndrome associated with type 2 diabetes: e.g., a reduction of the macrovascular-disease-promoting sulfonylurea side effects (e.g., carnitine depletion) and/or (possibly) a reduction of metformin-induced hyperhomocysteinemia.

The formulations of the invention will enhance the microvascular benefits associated with the sulfonylureas. In addition, by rectifying the adverse side effects of sulfonylurea treatment, and by modifying the adverse components of the insulin resistance syndrome, the invention will decrease the risk of macrovascular disease.

If combined with caloric dietary regulation, rapid- and short-acting sulfonylureas may help patients reach and maintain euglycemia without provoking chronic hyperinsulinemia or weight increase. There is no evidence that sulfonylurea treatment causes β-cell exhaustion; instead, the antihyperglycemic effect helps improve β-cell function. Sulfonylurea "failures" are often dietary failures or due to late introduction of these drugs, i.e., when β-cell function is already attenuated. Desensitization of the insulinotropic effect of sulfonylureas may occur, but might be avoided by discontinuous (less than 24 h/day) sulfonylurea exposure, i.e., once-daily administration of a short-acting sulfonylurea in a moderate dose. That is, the failure rate seems to dose related. The invention will permit the clinician more latitude in adjusting downward the dosage of a prescribed sulfonylurea, and it will permit "pulsing" of the latter and avoid desensitization. Furthermore, it will provide the luxury of a safe delay of use of the because of a prophylactic prolongation of improved β-cell function: this delay in the use of the sulfonylureas will delay the onset of their failure. It is not expected that it will eliminate entirely ultimate failure.

A.3. Sulfonylurea: Additional Beneficial Effects

Type 2 diabetes mellitus is part of a complicated metabolic-cardiovascular pathophysiologic cluster alternately referred to as the insulin resistance syndrome, Reaven's syndrome, the metabolic syndrome or syndrome X. Since the macrovascular coronary artery disease associated with insulin resistance and type 2 diabetes is the major cause of death in the latter, it is desirable that any hypoglycemic agent favorably influences known cardiovascular risk factors. But the results in this area have been only mildly encouraging. This invention will improve the ability of the sulfonylureas to reduce macrovascular cardiovascular risk factors.

Sulfonylureas have been reported to have a neutral or just slightly beneficial effect on plasma lipid levels: plasma triglyceride levels decrease modestly in some studies. This hypolipidemic effect probably results from both a direct effect of sulfonylurea on the metabolism of very-low-density lipoprotein (VLDL) and an indirect effect of sulfonylurea secondary to its reduction of plasma glucose levels.

It has been shown the sulfonylurea gliclazide (but not necessarily another oral hypoglycemic) reduces platelet aggregation and has a beneficial effect on the fibrinolytic system. As a group, the sulfonylureas decrease vessel permeability in a manner that is independent of their hypoglycemic properties. These additional actions may be useful in preventing or attenuating the long-term vascular complications of diabetes, e.g., diabetic retinopathy. While the favorable effect of reducing platelet aggregation seems established, a disturbing recent study shows an increase in PAI-1 in chronically treated sulfonylurea patients.

The formulations of this invention will enhance and/or extend the beneficial sulfonylurea effect on plasma lipids, coagulopathy and microvascular permeability.

A.4. Sulfonylurea: Adverse Effects

The most frequent adverse effect associated with sulfonylurea therapy is weight gain, which is also implicated as a cause of secondary drug failure.

Sulfonylureas frequently: (1) stimulate renal renin release; (2) inhibit renal carnitine resorption; (3) increase PAI-1; and (4) increase insulin resistance.

Renal effects from treatment with the sulfonylureas can be detrimental. Because the sulfonylureas are K(ATP) blockers they are diuretics although, fortunately, they do not produce kaliuresis. They may stimulate renin secretion from the kidney, initiating a cascade to angiotensin II in the vascular endothelium that results in vasoconstriction and elevated blood pressure.

They inhibit renal carnitine reuptake. This raises the question as to what role they play in the homeostasis of other amino acids for which deficiencies should be avoided in progressive insulin resistance and type 2 diabetes, e.g., taurine and L-arginine. Given these renal effects of the sulfonylureas, it is not surprising that there macrovascular benefits are not associated with their use. (See above.) Sulfonylureas, while reducing hyperglycemia, tend to intensify the insulin resistance syndrome: obesity, insulin resistance, hypertension, and coagulopathy. The formulations of this invention reduce this negative effect on the insulin resistance syndrome and the secondary amino acid deficiencies caused by the clinical use of sulfonylureas.

The kidney plays an important role in the homeostasis of carnitine, reabsorbing it almost completely from the glomerular filtrate. Carnitine is pivotal for the mitochondrial energy system to function efficiently. Its deficiency leads to reduced fatty acid oxidation and ATP production, both of which are important in avoiding weight gain and maintaining the effectiveness of nutrient insulin secretagogues. This invention improves sulfonylurea-induced inhibition of hepatic fatty acid oxidation and provides support for the production of ATP (necessary for physiologic pancreatic insulin production), thereby lessening the adverse weight gain secondary to sulfonylurea treatment and reducing the accumulation of fatty acid-derived free radicals.

Sulfonylurea treatment induces coronary vasoconstriction from $K^+$ ATP-channel blockade, and thus reduces coronary blood flow at rest by about 25%. It does not reduce flow during exercise so long as the L-arginine-cNOS-NO-cGMP pathway is normal. The invention provides support for the cGMP pathway.

PAI-1 antigen and activity increase with sulfonylurea treatment compared to insulin perhaps explaining, in part, the failure of prevention of macrovascular complications in spite of glycemic control.

Proinsulin levels may increase during sulfonylurea therapy.

The most discussed, important adverse effect of chronic sulfonylureas use is long lasting, significant hypoglycemia. The latter may lead to permanent neurological damage or even death, and is most commonly seen in elderly subjects who are exposed to some intercurrent event (e.g., acute energy deprivation) or to drug interactions (e.g., aspirin, alcohol). Long-lasting hypoglycemia is more common with the longer-acting sulfonylureas glyburide and chlorpropamide. For this reason sulfonylurea therapy should be maintained at the lowest possible dose. (Surprisingly, the dose-response relationships of the sulfonylureas have been poorly investigated.) By complementing and efficiently optimizing the therapeutic action of sulfonylurea, the formulations of this invention permit the use of minimal doses of sulfonylureas, thereby lowering the risks of sulfonylurea therapy, including hypoglycemia.

There is a greater suppression of hepatic glucose production with glyburide, which may explain the higher incidence of hypoglycemia seen with its use: mild hypoglycemic reactions occur in about 4% of patients, and severe hypoglycemic reactions requiring hospitalization have been stated to occur with a frequency of 0.4 cases per 1000 patient treatment years. The UKPDS reported a somewhat higher incidence.

In two surveys (1969 and 1984), all emergency wards in Switzerland reported on the incidence in their units of severe episodes of hypoglycemia during treatment with sulfonylureas. Each of these surveys referred to a ten-year period (period A 1960–1969, period B 1975–1984). The number of severe episodes of hypoglycemia reported was 78 for period A and 116 for period B. The incidence of fatalities from sulfonylurea hypoglycemia in these facilities was 6.5% in period A (1960–1969), and 4.3% in period B (1975–1984). Advanced age was a risk factor in hypoglycemia in these patients: 77% of patients with hypoglycemia were over 69 years of age, whereas only 50% of all diabetics treated with sulfonylurea preparations were in this age group. Further risk factors were impaired renal function (21%) and possible drug interactions (27%).

As our population ages and as the prevalence of 'couch potatoes' rises, the danger of sulfonylurea hypoglycemia continually increases. The formulations of this invention are of increasing importance, because they permit clinical reductions in sulfonylurea dose levels.

In patients with a reduced glomerular filtration rate, the risk of hypoglycemia is high, and therapy with sulfonylureas, which are renally excreted, should be avoided.

The various adverse, dose-related drug interactions that have been described (notably, aspirin and alcohol), are especially common with first-generation sulfonylureas.

The controversial results of the University Group Diabetes Program study (1970) suggested that sulfonylureas might exacerbate coronary artery disease in patients with type 2 diabetes. Subsequent clinical trials have not demonstrated these increased cardiac mortality rates in diabetic patients actually treated with sulfonylureas. In fact, the UKPDS found no increased incidence of coronary artery disease in those patients with type 2 diabetes, who were assigned to intensive therapy with sulfonylureas, when compared with patients receiving diet therapy. There is no published data to support an advantage of any one sulfonylurea with respect to coronary artery disease. An American Diabetes Associations policy statement opposes any formal restrictions based on the interpretations of the University Group Diabetes Program findings.

| A.5. Currently available sulfonylureas (USA: | | | |
|---|---|---|---|
| SULFONYLUREAS | Approved Daily Dosage mg | Usual Daily Dosage mg | Duration of Action hours |
| SECOND GENERATION | | | |
| Glimepiride | 1–8 | 1–4 | 16–24 |
| Glipizide | 5–40* | 5–20 | 12–24 |

-continued

A.5. Currently available sulfonylureas (USA:

| SULFONYLUREAS | Approved Daily Dosage mg | Usual Daily Dosage mg | Duration of Action hours |
|---|---|---|---|
| Glipizide (XL) | 5–20 | 5–20 | 24 |
| Glyburide | 1.5–12? | 5–20? | 12–24 |
| Glyburide (micronase) | 2.5–20 | 5–20 | 16–24 |
| FIRST GENERATION | | | |
| Acetohexamide | 250–1500 | 500–750 | 12–18 |
| Chlorpropamide | 100–500 | 250–375 | 60 |
| Tolazamide | 100–1000 | 250–500 | 12–24 |
| Tolbutamide | 500–2500 | 1000–2000 | 6–12 |

*Although short-acting glipizide has been approved at a dosage of 40 mg/d, the maximally effective dosage is 20 mg/d.
Other sulfonylureas (gliclazide, gliquidone, glibornuride, and glisoxepide) are available outside the United States.

Sulfonylureas are divided into first-generation and second-generation drugs. First-generation sulfonylureas have a lower binding affinity to the sulfonylurea receptor and require higher doses than second-generation sulfonylureas. Generally, therapy is initiated at the lowest effective dose and titrated upward every 1 to 4 weeks until a fasting plasma glucose level of 110 to 140 mg/dL is achieved. Most (75%) of the hypoglycemic action of the sulfonylurea occurs with a daily dose that is half of the maximally effective dose. If no hypoglycemic effect is observed with half of the maximally effective dose, it is unlikely that further dose increases will have a clinically significant effect on blood glucose level.

In summary, sulfonylureas are effective glucose-lowering drugs that work by stimulating insulin secretion. They have a beneficial effect on diabetic microangiopathy, but no appreciable effect on diabetic macroangiopathy. Weight gain is common with their use. Sulfonylureas may cause hypoglycemia, which can be severe, even fatal. They may reduce platelet aggregation and slightly increase fibrinolysis, perhaps indirectly. However they also may increase PAI-1. They have no direct effect on plasma lipids. They inhibit renal resorption of carnitine and may stimulate renal renin secretion. The sulfonylureas, especially generics, are inexpensive and are the oral antidiabetic drug of choice if cost is the major consideration. Sulfonylurea dosage can be minimized, their therapeutic effect maximized, their safety improved and the scope of their beneficial effects broadened in progressive insulin resistance, insulin resistance syndrome and type 2 diabetes by formulations of this invention.

A.6. Adjunctive Use of the Invention for the Prevention and Treatment of Insulin Resistance Syndrome and Type 2 Diabetes As illustrated by the foregoing list of cellular physiological and molecular biological disturbances, both insulin resistance syndrome and type 2 diabetes are progressive complex, dynamic metabolic system failures with potential instability at many points. Its genesis is in part related to the aging process and is in part a product of environment and lifestyle. Underlying it all is a genetic dimension, which is not singular in nature. Because there are so many points of physiologic instability, neither pathologic process will predictably respond in its entirety to a single treatment modality. Rather, it is more logical to provide a favorable physiologic milieu by identifying those multiple points where influence upon biochemical modulation may reasonably be brought to bear and to design multicomponent therapeutic formulations to target them concurrently. In this fashion the therapy will insure that molecular deficiencies or inadequacies do not trigger the system to respond nonlinearly to those stresses known to be detrimental to persons with the potential for developing (or who already have) insulin resistance or type 2 diabetes. This physiologic modulation is achieved by the formulations of this invention and is the basis for their improvement in the therapeutic efficiency and safety of sulfonylureas.

As an individual progresses toward and into type 2 diabetes, an increasing number of specific complementary biomolecules, biofactors and trace elements are necessary to compliment sulfonylureas, as shown in the following illustrations. It should be pointed out that a "shotgun" approach that throws everything in the biochemical bible at insulin resistance or the type 2 diabetic not only is illogical, unnecessary and expensive, but also may be detrimental. Errors of commission in this regard are as inappropriate as errors of omission.

The present invention resides in a pharmaceutical preparation for use as an oral dosage form for increasing the effectiveness, efficiency and safety of sulfonylureas in prevention and treatment of insulin resistance and/or type 2 diabetes. The preparation contains specific, sometimes unique, therapeutic biomolecules, biofactors and trace elements selected because of their particular and critical, combinational physiological effects. These are formulated in amounts to achieve maximum complementarity of action with sulfonylureas.

When used separate from the sulfonylureas, the formulations of the invention will be effective in preventing the development or slowing the progression of insulin resistance and type 2 diabetes. This may delay the time when a sulfonylurea is required and so reduce the adverse effects that accumulate with prolonged use.

In the United States alone, 16 million people have type 2 diabetes and a substantial multiple, perhaps 4× to 5×, are insulin resistant—at least one-half of these are undiagnosed. Type 2 diabetes is preceded by a long period of insulin resistance, impaired glucose tolerance and a reversible metabolic state associated with an increasing prevalence of macrovascular complications. At the time of diagnosis, long-term complications have already developed in almost one fourth of these patients, largely because of insulin resistance and its associated hyperinsulinemia and dyslipidemia.

Susceptibility to type 2 diabetes requires both genetic (most likely polygenic) and acquired factors. Its continuing pathogenesis involves an interplay of progressive cellular insulin resistance and pancreatic β-cell failure. Any ideal treatment of type 2 diabetes must reduce insulin resistance and β-cell dysfunction in a majority of treated patients and prevent, delay, or reverse the long-term complications.

One strategy of this invention is an attack on multiple pathophysiological processes by innovatively potentiating sulfonylurea. This is accomplished by combinations of biomolecules (some unique), biofactors and trace elements with disparate, although often complementary or synergistic, mechanisms of action in order to provide for better sulfonylurea management of the insulin resistance syndrome, more efficient prevention of type 2 diabetes, better management of type 2 diabetes and for prevention of long-term macrovascular and microvascular complications.

This invention enhances sulfonylureas' insulin secretagogue effect and its effect on reducing glucose toxicity.

The complexity of type 2 diabetes pathophysiology provides the opportunity to expand sulfonylureas' clinical usefulness by the administration of complementary, novel combinations of biomolecules, biofactors and trace elements, many of which are deficient or functionally inadequate in diabetics, or which may be unfavorably altered by sulfonylurea therapy.

The invention will enhance sulfonylureas' efficiency by:
Reducing diabetic microvascular complications,
Modulating $Ca^{2+}$ signaling and β-cell membrane polarization,
Increasing insulin secretion and reducing hyperglycemia,
Maintaining synergy in the β-cells between amino acids and sulfonylureas,
Inhibiting platelet aggregation,
Reducing norepinephrine (NE) release from cardiac sympathetic nerves.

The invention will expand sulfonylureas' areas of effect by:
Reducing diabetic macrovascular complications,
Inhibiting mitochondrial-derived apoptosis,
Increasing the number of insulin receptors and the duration of action of insulin,
Increasing hepatic and peripheral insulin sensitivity,
Optimizing the β-cell cytoplasmic free $Ca^{2+}$ level,
Improving lipid profiles,
Reducing non-enzymatic glycation and advanced glycation end products,
Reducing the free radical effect at the caveolae and insulin receptor,
Reducing PAI-1 inhibitor and improving fibrinolysis.

The invention will reduce sulfonylureas' adverse effects by:
Reducing sulfonylurea-induced weight gain and inadequate fatty acid oxidation,
Reducing the sulfonylurea risk of hypoglycemia,
Reducing sulfonylurea gastrointestinal side effects,
Lessening the sulfonylurea hypofibrinolytic effect,
Reducing sulfonylurea-induced vasoconstriction.

This invention provides adjunct formulations to enhance treatment of progressive insulin resistance and type 2 diabetes with a sulfonylurea. This invention addresses sulfonylurea-induced mitochondrial malfunction and the failure of sulfonylurea to prevent diabetic macrovascular disease. It improves the useful antihyperglycemic effects of the sulfonylureas and adds an antihyperinsulinemia effect. It improves nocturnal control. It will in some patients provide at least a temporary substitute for insulin. The cumulative effect of this invention will extend the period of time that sulfonylureas can provide effective reduction of hyperglycemia.

By these various means, the invention will increase the number of patients who will benefit from sulfonylureas and the sulfonylurea-like oral antidiabetic drugs, in particular repaglinide.

B. Biguanides (Metformin)

B.1. Metformin: Pharmacodynamics and Pharmacokinetics

The biguanides metformin (GLUCOPHAGE®) and phenformin were introduced in 1957. Phenformin was withdrawn in many countries because of an association with lactic acidosis a complication with which metformin is only rarely involved. This invention focuses on the diethyl biguanide, metformin Metformin has a unique mechanism of action and controls glycemia in both obese and normal-weight, type 2 diabetes patients without inducing hypoglycemia, insulin stimulation or hyperinsulinemia. It prevents the desensitization of human pancreatic islets usually induced by hyperglycemia and has no significant effect on the secretion of glucagon or somatostatin. As a result it lowers both fasting and postprandial glucose and $HbA_{1c}$ levels. It improves the lipid profile. It does not increase lactate production as much as other biguanides from skeletal muscle (e.g., phenformin): lactic acidosis associated with metformin use is rare (reported incidence of 0.03/1,000 patient-years exposure) and has occurred mostly in patients for whom the drug was inappropriate. Metformin can be safely used in the elderly, providing conservative doses are used.

Glucose levels are reduced during metformin therapy secondary to reduced hepatic glucose output from inhibition of gluconeogenesis and glycogenolysis. To a lesser degree it increases insulin action in peripheral tissues. Metformin also may decrease plasma glucose by reducing the absorption of glucose from the intestine, but this does not appear to be of clinical importance.

Metformin enhances the sensitivity of both hepatic and peripheral tissues (primarily muscle) to insulin as well as inhibiting hepatic gluconeogenesis and hepatic glycogenolysis. This decline in basal hepatic glucose production is correlated with a reduction in fasting plasma glucose levels. Its enhancement of muscle insulin sensitivity is both direct and indirect. Improved insulin sensitivity in muscle from metformin is derived from multiple events, including increased insulin receptor tyrosine kinase activity, augmented numbers and activity of GLUT4 transporters, and enhanced glycogen synthesis. However, the primary receptor through which metformin exerts its effects in muscle and in the liver is as yet unknown. In metformin-treated patients both fasting and postprandial insulin levels consistently decrease, reflecting a normal response of the pancreas to enhanced insulin sensitivity.

Metformin has a mean bioavailability of 50–60%. It is eliminated primarily by renal filtration and secretion and has a half-life of approximately 6 hours in patients with type 2 diabetes; its half-life is prolonged in patients with renal impairment. It has no effect in the absence of insulin. Metformin is as effective as the sulfonylureas in treating patients with type 2 diabetes, but has a more prominent postprandial effect than either the sulfonylureas or insulin. It is therefore most useful in managing patients with poorly controlled postprandial hyperglycemia and in obese or dyslipidemic patients; in contrast, the sulfonylureas or insulin are more effective in managing patients with poorly controlled fasting hyperglycemia.

B.2. Metformin: Effectiveness

Except perhaps for its appearance in aging, insulin resistance and type 2 diabetes do not usually occur in isolation, but as part of the complex metabolic-cardiovascular 'Syndrome X', mentioned previously. Hyperinsulinemia and hyperglycemia are risk factors for all of the pathologies involved with the syndrome. Therefore, an initial recognition of these many intermingled relationships must precede the design of effective treatment of these entwined pathologies, and both hyperinsulinemia and hyperglycemia must be controlled if adverse macrovascular and microvascular complications are to be avoided. Long-term prospective studies have shown that treatment of hypertension and dyslipidemia reduces cardiac events in patients with type 2 diabetes. As an example, the United Kingdom Prospective Diabetes Study (UKPDS) showed that improved control of blood pressure reduced not only macrovascular complications (heart attacks, strokes, and death), but also the risk for microvascular end points by 37% (P=0.009). It is clearly important that pharmacological therapy not aggravate risk factors but leads to their improvement. Because obesity and physical inactivity are global risk factors for coronary artery disease as well as for diabetes, the need for weight loss and exercise must be stressed when diabetes initially is diagnosed, and must be reinforced throughout the natural history of the disease. However, modification of these may not be sufficient for clinical management. Metformin has been an attractive therapeutic aid.

Metformin is absorbed mainly from the small intestine. It is stable, does not bind to plasma proteins, and is excreted unchanged in the urine. It has a half-life of 1.3 to 4.5 hours. The maximum recommended daily dose of metformin is 3 g, taken in three doses with meals.

When used as monotherapy, metformin clinically decreases plasma triglyceride and low-density lipoprotein (LDL) cholesterol levels by 10% to 15%, reduces postprandial hyperlipidemia, decreases plasma free fatty acid levels, and free fatty acid oxidation. Metformin reduces triglyceride levels in non-diabetic patients with hypertriglyceridemia. HDL cholesterol levels either do not change or increase slightly after metformin therapy. By reducing hyperinsulinemia, metformin improves levels of plasminogen activator inhibitor (PAI-1) and thus improves fibrinolysis in insulin resistance patients with or without diabetes. Weight gain does not occur in patients with type 2 diabetes who receive metformin; in fact, most studies show modest weight loss (2 to 3 kg) during the first 6 months of treatment. In one 1-year randomized, double blind trial, 457 non-diabetic patients with android (abdominal) obesity, metformin caused significant weight loss.

Metformin reduces blood pressure, improves blood flow rheology and inhibits platelet aggregation. In part this results from the maintenance physiologic levels of constitutive NO; in part by attenuation of the agonist-stimulated ($Ca^{2+}$) response in VSMC in parallel with the effect of calcium channel blockers.

Treatment of insulin resistance with metformin may also have important applications unique to women, particularly in polycystic ovary syndrome by reducing ovarian cytochrome P450c17 alpha activity and ameliorating hyperandrogenism. It is also possible that improving insulin sensitivity after menopause improves the cardiovascular prognosis of aging women.

These beneficial effects of metformin on various elements of the insulin resistance syndrome help define its usefulness in the treatment of insulin resistance and type 2 diabetes. These useful effects are enhanced when metformin is combined with components of this invention. The latter increase its effectiveness and efficiency, improve its safety and expand the arena of its medical benefit.

Unquestionably the UKPDS established that type 2 diabetes is a progressive disorder. Ideally, treatment with metformin (or a sulfonylurea, or insulin) would halt the progressive deterioration of glycemic control; this is not the case. For example: After an initial (and equivalent) decrease in elevated plasma glucose levels ($HbA_{1c}$) of 1.5 to 2.0 percentage points, the long term rate of increase in this value during treatment with metformin (or a sulfonylurea, or insulin) was identical to that for a group treated merely with diet therapy. These results suggest that once overt fasting hyperglycemia has developed, the decline in glycemic control is relentless. In the UKPDS, this decline was related to deterioration of β-cell function. The University Group Diabetes Program study similarly confirmed the progressive nature of type 2 diabetes. These important studies emphasize the need for constant reassessment of patients with insulin resistance and/or diabetes, and for appropriate adjustment of the therapeutic regimen in order to avoid hyperinsulinemia, deterioration or apoptosis of β-cells and progressive loss of control over hyperglycemia.

Metformin reduces measurable levels of plasma triglycerides and LDL cholesterol and is the only oral, monotherapy, antidiabetic agent that has the potential to reduce macrovascular complications, although this favorable effect is attenuated by its tendency to increase homocysteine levels. Likewise, it is the only oral hypoglycemic drug wherein most patients treated lose weight or fail to gain weight.

This invention introduces a strategy to increase the safety and efficiency of metformin in suppressing recognized risk factors, thus slowing disease progression by extending both the duration and the breadth of metformin's therapeutic value. The strategy of this invention will increase the number of patients by whom metformin can be used at reduced dose levels, thereby avoiding, delaying and lessening metformin's adverse effects.

B.3. Metformin: Adverse Effects

Gastrointestinal side effects (diarrhea, nausea, abdominal pain, and metallic taste—in decreasing order) are the most common adverse events, occurring in 20% to 30% of patients. These side effects usually are mild and transient and can be minimized by slow titration. If side effects occur during titration, they can be eliminated by return to the dose at which no symptoms were encountered.

Metformin interferes with vitamin B12 absorption (an effect which is likely to be exaggerated in the elderly) and reduces serum vitamin B12 levels. This is a probable factor in the elevated levels of homocysteine (Hcy) which develop during treatment with metformin: the metabolism of Hcy depends on the vitamins $B_6$, $B_{12}$ and folate.

Lactic acidosis due to interference with the pyruvate oxidative pathway has rarely been reported with metformin use: a reported frequency of 3 cases per 100,000 patient-years occurs. However, patients with renal impairment should not receive metformin; since it is cleared by urinary excretion, severe lactic acidosis can result. Hepatic disease, a past history of lactic acidosis (of any cause), cardiac failure, and chronic hypoxic lung disease are additional contraindications to its use. These conditions all predispose to increased lactate production and hence to potentially lethal lactic acidosis.

This potentially fatal complication of biguanide therapy follows excessive circulating biguanide levels and is a greater risk in elderly patients—especially those older than 80—in whom an age-related decrease in glomerular filtration rate is often seen. In such patients, it is recommended that creatinine clearance be measured before starting metformin therapy and that the metformin dose be minimized.

This invention, by specifically countering metformin side effects and/or by reducing the optimal metformin dose, will in turn, reduce the adverse effects of metformin therapy, while enhancing its beneficial effects. This is especially true for elderly patients. It may permit a least a limited number of patients with marginal renal and hepatic function to safely use metformin.

Metformin may be used alone or may be combined in a stepwise fashion with formulations of this invention in order to manage insulin resistance syndrome, avoid hyperinsulinemia and subsequent hyperglycemia, and help to provide ideal glycemic control. Adjunct uses of this invention comprise pharmacological approaches that will help to improve glycemic control by reducing the risks associated with specific abnormalities of several conditions and functions frequently associated with insulin resistance and/or type 2 diabetes. These include, among others, dysfunctional vascular endothelium, inappropriate apoptosis, undesirable platelet agglutination, inadequate maintenance of cell volume, dyslipedemia, hyperhomocysteinemia, β-cell "exhaustion" or destruction, and the accumulation of advanced glycation end products.

B.4. Adjunctive Use of the Invention for the Prevention and Treatment of Insulin Resistance Syndrome and Type 2 Diabetes an individual progresses from often-covert insulin resistance toward and into type 2 diabetes, and has a corresponding need for drug therapy, metformin is often the drug of choice. However, because of limitations upon its chronic use and cumulative adverse effects, an increasing number of specific biomolecules, biofactors and trace elements, as shown in the following illustrations, become necessary to compensate for these deficiencies and adverse side effects. Oral dosage forms are described by the invention.

In addition to rectifying adverse effects secondary to the clinical use of metformin, the present invention defines pharmaceutical formulations for use as oral dosage forms for increasing the effectiveness, efficiency and safety of metformin therapy in the treatment of insulin resistance and/or type 2 diabetes. The preparation contains specific, sometimes unique, therapeutic biomolecules, biofactors and trace elements selected because of their particular and critical, combinational physiological effects.

One strategy of this invention is to modulate multiple pathophysiological processes to innovatively improve the clinical use metformin. This is accomplished by combinations of active ingredients with disparate, although often complementary or synergistic, mechanisms of action in order to provide for better metformin management of the insulin resistance syndrome, more efficient prevention of type 2 diabetes, better management of type 2 diabetes and for prevention of long-term macrovascular and microvascular complications.

The invention will enhance metformin's areas of influence in:
Reducing diabetic microvascular complications.
Modulating gluconeogenesis.
Reducing dyslipidemia.
Reducing hypertension (increase NO).
Reducing hypertension (modify dysfunctional calcium signaling).
Improving polycystic ovary syndrome.
Increasing insulin receptor sensitivity .
Inhibiting platelet adhesion and aggregation.
Reducing AGEs.
Reducing cell membrane damage from free radicals.
The invention will expand metformin's areas of effect by:
Reducing diabetic macrovascular complications.
Inhibiting mitochondrial effected apoptosis.
Preventing progression from type 2 to "type 1.5" diabetes.
Improving insulin secretion.
Modifying post-receptor disturbances of insulin resistance.
Increasing the number of insulin receptors and the duration of action of insulin.
The invention will prevent or reduce metformin's dose-related adverse effects by:
Reducing gastrointestinal side effects.
Reducing hyperhomocysteinemia.
Reducing risk of lactic acidosis This invention provides formulations to be used as adjuncts to the clinical use of metformin toward the end of enhancing the treatment of progressive insulin resistance and type 2 diabetes. By these various means, the invention will increase the number of patients who will benefit from metformin therapy.

C. Combined Biguanide (Metformin)-Sulfonylurea

The invention contemplates the clinical use of therapeutic combinations of metformin and a member of the sulfonylurea family; that is, situations which may arise clinically in which a practitioner may prescribe the concurrent use of metformin and a sulfonylurea, either in a single dosage form or as separate dosage forms.

The above recitations describe side effects and deficiencies that arise from the individual use of metformin and of the sulfonylureas. Certainly all of the deficiencies and adverse effects that are listed may occur together in a single individual—it is more likely that the incidence of each adverse effect or deficiency should be considered a clinical variable with a significantly wide degree of incidence across patient populations. As a result, predicting the frequency and intensity of each adverse effect or deficiency for either metformin or for one of the sulfonylureas, becomes a statistical consideration of greater or lesser accuracy.

The clinical use of combinations of metformin and a sulfonylurea introduces more variables into this statistical calculation. Until sufficient clinical use of these combinations has occurred and has been evaluated, the existence or development of unique side effects and deficiencies cannot be known. It may rationally be assumed, however, that the side effects and deficiencies of each will statistically sort into about the same incidence currently present when each drug is used individually. However, whether or not some unknown adverse synergy may develop is not now predictable. It therefore cannot be therapeutically anticipated.

The invention contemplates that the formulations described individually for these two treatments—metformin and the sulfonylureas—will be equally useful and effective when these therapeutic drugs are used concurrently.

The invention gives the practitioner an opportunity to provide adjunctive support for a wide spectrum of patients who are at risk of insulin resistance and type 2 diabetes, including those who do not require either metformin or a sulfonylurea, those who are prescribed one or the other, and those patients who require both.

Formulation Groups of This Invention

The ingredients within the invention are organized into four functionally interrelated and interdependent, adjunct formulation groups: 1. Mitochondrial Metabolic Group, 2. Plasma and Mitochondrial Membrane Integrity Group, 3. Nocturnal Group and 4. Insulin Alternative Group. What follows is a summary. More extensive discussion of each ingredient is present further below in the document.

| I. MITOCHONDRIAL METABOLIC GROUP) Dosages in Milligrams | | |
|---|---|---|
| | Preferred | Most Preferred |
| L-Carnitine | 90 to 2500 | 300 to 1000 |
| Ascorbate | 75 to 2500 | 250 to 1000 |
| Choline | 15 to 250 | 50 to 100 |
| Taurine | 75 to 3125 | 250 to 1250 |
| Magnesium | 30 to 1000 | 100 to 400 |
| Folic Acid | 0.03 to 2.0 | 0.10 to 0.80 |

Metformin is involved in a cell-signaling pathway targeted to the mitochondrial respiratory chain complex I and has a persistent effect even after cessation of the signaling process. Mitochondrial abnormalities occur in the hepatocytes of patients with hyperhomocysteinemia via homocysteine-induced expression of the mitochondrial electron transport chain gene, cytochrome c oxidase III/ATPase 6,8. Homocysteine and $H_2O_2$ (but not $H_2O_2$ alone) causes a decrease in mitochondrial RNA levels, providing evidence that homocysteine and $H_2O_2$ act synergistically to cause mitochondrial damage. Homocysteine, associated with vasoconstriction, hypertension and thrombogenesis, tends to be elevated by metformin treatment. Metformin-induced hyperhomocysteinemia can be prevented by folic acid, a component of this group.

Sulfonylureas reduce available carnitine by restricting the renal reuptake of carnitine. In turn, this reduces the carnitine-directed transfer of long chain fatty acids into the mitochondria—the main ATP (energy) source for the latter. Exogenous carnitine and choline (which lessens carnitine renal loss) tend to normalize the mitochondrial fuel supply. Taurine, often low in progressive insulin resistance and type 2 diabetes, is required to move $Ca^{2+}$ into the mitochondria to signal ATP production. Magnesium is also necessary in the modulation of intracellular $Ca^{2+}$: it works with mitochondrial-generated ATP to transfer excess cytoplasmic $Ca^{2+}$ out of the cell—this transfer re-establishes cell membrane repolarization, which is necessary for sulfonylurea-metformin to activate the next shift of insulin into the bloodstream.

II PLASMA AND MITOCHONDRIAL MEMBRANE INTEGRITY GROUP
Dosages in Milligrams

|  | Preferred | Most Preferred |
|---|---|---|
| D-α-Lipoic Acid | 30 to 1500 | 100 to 600 |
| N-acetyl-Cysteine | 78 to 3900 | 200 to 1200 |
| Ubiquinone | 4.5 to 225 | 15 to 90 |
| Selenium | 0.02 to 0.75 | 0.05 to 0.3 |
| Tocopherol-Tocotrienol | 15 to 1600 | 50 to 800 |
| L-Arginine | 75 to 3125 | 250 to 1250 |
| Tetrahydrobiopterin | 24 to 3000 | 80 to 1200 |

The plasma membrane consists of a bilayer of amphipathic phospholipids that provides an anionically charged fluid barrier with selective permeability and selective active-transfer mechanisms. The membrane houses protein molecules in arrangements that support their functionality and provide a surface consistent with the needs of ligands. In the case of the vascular endothelium, this arrangement must provide a physiologic surface that is proper both for circulating cells and favorable luminal flow. If the cell membrane loses its integrity, $Ca^{2+}$ modulation is impossible, endothelin-1(ET-1) increases and NO is induced into an iNOS Type II inflammatory condition: the latter contributes to inflammation and cell death, including pancreatic β-cells. The sum of these events leads to further loss of membrane integrity. There now exists the proverbial circle in a spiral of, vascular degradation, local hypoxia, thrombogenesis and atrophy/apoptosis causing the macrovascular complications of progressive insulin resistance and type 2 diabetes.

The permeability transition pore, a multiprotein complex formed at the contact site between the mitochondrial inner and outer membranes, is the rate limiter of apoptosis. This mitochondrial permeability pore becomes dysfunctional (it opens) because of: (1) uncoupling of the respiratory chain within the membrane leading to the cessation of ATP synthesis, (2) hyperproduction of superoxide anions, (3) repletion or oxidation of non-oxidized glutathione, and (4) disruptions of $Ca^{2+}$ homeostasis. These perturbations are lethal to the status levels of mitochondrial energy. Ubiquinone (coenzyme Q10) is integral to the mitochondrial respiratory chain and additionally, working synergistically with α-tocopherol, it reduces mitochondrial superoxide anions.

Some diabetic complications relating to cell membrane integrity may be worsened by sulfonylurea or metformin treatment.

Glutathione (GSH) is the most important intracellular defense against free radicals generated by mitochondrial metabolism and excess free radicals secondary to hyperglycemia. It becomes depleted in diabetes. Metformin increases available GSH in both diabetics and non-diabetics, indicating that it has some antioxidant activity that is independent of, and in addition to, its reductions of hyperglycemia.

GSH, a tripeptide is not adequately absorbed from the gastrointestinal tract and requires a substrate; N-acetyl-cysteine is present in this invention as a GSH prodrug. GSH is conserved by the potent free radical scavenger α-lipoic acid. Selenium is an imperative cofactor for glutathione peroxidase, which is required for optimized GSH activity. D-α-tocopherol and ascorbic acid act synergistically to directly reduce peroxidation of membrane phospholipids, complimenting GSH. The combination of these ingredients stabilizes membrane proteoglycans, preserving the anionic charge necessary for normal permeability characteristics, which are imperative if diabetic micro and macrovascular complications are to be avoided.

L-arginine administration maintains the substrate necessary to permit normal, constitutive NO/cGMP. This balances the increased ET-1 of progressive insulin resistance, and compliments prostacyclin in maintaining the smooth, healthy, vascular endothelial surfaces required for normal, laminar blood flow.

Tetrahydrobiopterin (BH4) is an essential cofactor for nitric oxide synthase. In low concentrations of BH4, as is common in diabetes, nitric oxide synthase produces less constitutive NO and, correspondingly, larger quantities of the superoxide anion and hydrogen peroxide.

Excessive pancreatic β-cell apoptosis is responsible for the irreversible progression toward insulin dependence found in type 2 diabetes. The integrity of the mitochondrial membrane is essential for preventing β-cell dysfunctional apoptosis. The components of this group will inhibit the pre-mitochondrial (induction) phase of apoptosis caused by prooxidants, excessive cytosolic $Ca^{2+}$ and elevations of induced NO.

III NOCTURNAL GROUP
Dosages in Milligrams

|  | Preferred | Most Preferred |
|---|---|---|
| Melatonin | 0.15 to 7.5 | 0.5 to 3 |
| L-Carnitine | 90 to 2500 | 300 to 1000 |
| Ubiquinone | 4.5 to 225 | 15 to 90 |
| Folic Acid | 0.03 to 2.0 | 0.10 to 0.80 |
| Magnesium | 30 to 1000 | 100 to 400 |
| L-Arginine | 75 to 3125 | 250 to 1250 |
| Tetrahydrobiopterin | 24 to 3000 | 80 to 1200 |

Sulfonylureas can increase the risk of nocturnal hypertension and decrease myocardial tolerance for ischemia and reperfusion. They do appear to have some antiarrhythmic effect in preventing ventricular arrhythmias induced by transient myocardial hypoxemia.

Nocturnal occurrences of myocardial ischemia/reperfusion events is common in progressive insulin resistance and type 2 diabetes, and the post-infarction mortality rate in these patients is double that of non-diabetics. Bedtime adjunctive therapy, as defined in this invention, assist in reducing the nighttime risks of blunted nocturnal falls in blood pressure, myocardial ischemia and cardiac arrythmias; thereby complementing sulfonylurea and/or metformin treatment, and adding a dimension of protection against diabetic macrovascular complications.

The increased incidence of nocturnal myocardial ischemia and arrhythmias in progressive insulin resistance and type 2 diabetes relates to: (1) hypertension, (2) a blunted nocturnal fall in blood pressure, (3) hypoxemia induced by sleep apnea, (4) autonomic neuropathy, and (5) thrombogenesis. These are often interrelated. For example: in hypertension, sleep apnea syndrome and diabetes the normal nocturnal fall in blood pressure is absent or reversed. As another example: progressive insulin resistance causes hypertension and is associated with visceral obesity, which itself is a factor, along with insulin resistance, in causing sleep apnea. (See Reaven's syndrome above.) As mentioned earlier, the sulfonylureas increase visceral obesity by interfering with normal fatty acid oxidation in the mitochondria.

The formulations of this invention, as adjuncts to the use of sulfonylureas and/or metformin, will restore more normal circadian vascular physiology by: (1) reducing the nocturnal vasoconstriction related to hypertension and blunted nocturnal drops in blood pressure, (2) lessening cardiac autonomic neuropathy, (3) reducing thrombogenesis, (4) restoring physiologic fatty acid oxidation, and (5) reducing sleep apnea.

| IV INSULIN ALTERNATIVE GROUP Dosages in Milligrams | | |
|---|---|---|
| | Preferred | Most Preferred |
| Vanadium | 7.5 to 375 | 25 to 150 |
| L-Arginine | 75 to 3125 | 250 to 1250 |
| Chromium | 0.01 to 0.63 | 0.03 to 0.25 |
| Zinc | 1.5 to 125 | 5 to 50 |

Oral antidiabetic monotherapy, while initially successful in reducing hyperglycemia, seldom succeeds for more than a few years. Even with combinations of antidiabetic oral agents many patients eventually require insulin. The introduction of insulin in patients being treated with sulfonylurea or with metformin increases the twin risks of hypoglycemia and weight gain. It also reintroduces the hyperinsulinemic risks that are associated both with progressive insulin resistance and with primary sulfonylurea treatment. As treatment continues hyperinsulinemia recedes. The need for injectable insulin, however necessary, is a setback for the patient.

When hyperglycemia control inevitably fails, this invention provides a temporary oral alternative to insulin when used as an adjunct during treatment with sulfonylurea or metformin. This is achieved by: (1) adding a natural insulin secretagogue, (2) supplying an insulin-mimetic substance, (3) increasing insulin receptor sensitivity, (4) increasing the number of insulin receptors, (5) improving insulin receptor binding, and (6) prolonging insulin action. These are discussed more extensively further below.

L-arginine is an insulin secretagogue that directly supports insulin binding to its receptor, and increases insulin receptor sensitivity via constitutive NO. Glucose uptake is augmented by increased perfusion of skeletal muscles secondary to L-arginine/NO-induced vasodilation. Insulin's vasodilatation effect depends on insulin's regulation of NO production by increasing the availability of cofactor BH4 needed for activation of NO synthase. Supplementation of BH4 is a logical insulin mimic in achieving vasodilation.

Vanadium mimics insulin intracellularly and prolongs insulin action. It increases both hepatic and peripheral insulin sensitivity, and activates glycogenesis, decreasing hyperglycemia. Vanadium preserves pancreatic β-cells, and decreases diabetic hyperphagia, thereby improving both the safety and effectiveness of sulfonylurea and metformin.

Chromium, often deficient in diabetes, is a cofactor for insulin, increasing its binding to the insulin receptor and reducing insulin resistance. It increases the number of insulin receptors and facilitates insulin internalization by endocytosis from caveolae, thereby enhancing metformin's beneficial effect on peripheral insulin sensitivity.

$Zn^{2+}$ is involved with the synthesis, storage and secretion of insulin (thus aiding the sulfonylureas) as well as preserving its conformational integrity At the insulin receptor site, $Zn^{2+}$ prevents hyperglycemia by increasing insulin activity (aiding metformin); diabetics tend to have low plasma $Zn^{2+}$ concentrations and decreased total body $Zn^{2+}$, resulting in reduced insulin efficiency and hyperglycemia. Diabetics have increased urinary loss of $Zn^{2+}$, which in turn contributes to hyperglycemia. This vicious cycle supports the use of supplemental $Zn^{2+}$.

When added to an ongoing sulfonylurea and/or metformin regimen, this oral dosage form will usually be used in the evening, as is usually true when insulin is added. However, it is specifically designed to be used concomitantly and safely with daytime dosage forms of this invention, adding therapeutic complementarity without increasing risk. This provides the physician wide latitude of treatment options according patient need.

an adjunct to combined sulfonylurea and/or metformin therapy, this invention will reduce sulfonylurea and/or metformin requirements and will prevent or delay the need for injectable insulin in type 2 diabetes.

Molecular Complexes which May be Included in Formulations

The molecular complexes of this invention address various aspects of insulin resistance and type 2 diabetes such as 1) mitochondrial metabolism, 2) mitochondrial membrane integrity, 3) plasma membrane integrity, 4) adverse cytokine cascades, 5) dysfunctional β-cell apoptosis, 6) inappropriate $Ca^{2+}$ signaling, 7) insulin secretion, 8) insulin receptor sensitivity and 9) adverse effects of combinations of sulfonylurea-metformin.
1. Metal α-lipoic acid complexes
2. Metal L-arginine or L-arginine ascorbate complexes
3. Metal L-carnitine or L-carnitine ascorbate complexes
4. Metal L-taurine or L-taurine ascorbate complexes
5. Tocotrienol nicotinate, tocotrienol picolinate
6. D,α-tocopherol nicotinate, D,α-tocopherol picolinate
7. Peroxovanadate-nicotinic acid (POV)
8. Propionylcarnitine taurine bi-amide 1. α-Lipoic Acid Complexes
   α-Lipoic acid complexes included in the invention are used to increase the effectiveness, efficiency and safety of metformin in the prevention and treatment of progressive insulin resistance and diabetes mellitus. They have the following formulae:

[A]MX wherein,
a. A is α-lipoic acid or thioctic acid,
b. M is a metal ion taken from $Mg^{2+}$ or $Zn^{2+}$,
c. X is an anion taken from the group including hydroxides, halides, acetates or ascorbates acid salts.

or

M[A]

wherein,
a. A is α-lipoic acid or thioctic acid,
b. M is a metal ion taken from $Mg^{2+}$ or $Zn^{2+}$.

The α-lipoic acid is preferably in the form of either (a) an α-lipoic acid salt of a metal ion which is either $Mg^{2+}$ or $Zn^{2+}$, (b) a complex of α-lipoic acid, a metal ion which is either $Mg^{2+}$ or $Zn^{2+}$, and an anion which is either hydroxide, halide, acetate, or ascorbate.

The invention is a method for the oral administration of lipoic acid ascorbate or metallolipoate complexes, alone or in combination, as a nutrient for humans. The cation of the metallolipoate complexes may be $Mg^{2+}$ or $Zn^{2+}$.

The compound is preferably administered in an oral daily dosage with Preferred and Most Preferred amounts of individual components as shown in the example below.

EXAMPLE

Magnesium α-Lipoate

| Ranges in milligrams per day | Including Excipients Compound | Magnesium | α-Lipoate |
|---|---|---|---|
| Preferred | 87 | 3.6 | 60 |
| to | 1735 | 72 | 1200 |
| Most Preferred | 173 | 7 | 120 |
| to | 867 | 36 | 600 |

2. L-Arginine Complexes

L-arginine complexes included in the invention are used to increase the effectiveness, efficiency and safety of metformin in the prevention and treatment of progressive insulin resistance and diabetes mellitus. They have the following formulae:

[Arg]C wherein,
a. A is L-arginine or bis-L-arginine,
b. C is ascorbic acid or ascorbate, or

[Arg]MX a. Arg is the amino acid L-arginine or bis-L,arginine,
b. M is a metal ion taken from $Mg^{2+}$ or $Zn^{2+}$,
c. X is an anion taken from the group including hydroxides, halides, sulfates, phosphates, acetates, ascorbates or bis-ascorbic acid salts, or M[Arg]

wherein,
a. M is a metal ion taken from $Mg^{2+}$ or $Zn^{2+}$,
b. Arg is L-arginine or bis-L,arginine.

The L-arginine is preferably in the form of either (a) L-arginine ascorbate, (b) bis-L-arginine ascorbate, (c) an L-arginine salt of either $Mg^{2+}$ or $Zn^{2+}$, (d) a bis-L-arginine salt of either $Mg^{2+}$ or $Zn^{2+}$, or (e) a complex of L-arginine or bis-L-arginine, a metal ion that is either $Mg^{2+}$ or $Zn^{2+}$, and an anion that is either hydroxide, halide, acetate, or ascorbate.

The invention is a method for the oral administration of arginine ascorbate or metalloarginate complexes, alone or in combination, as a nutrient for humans. The cation of the metalloarginate complexes may be $Mg^{2+}$ or $Zn^{2+}$.

The compound is preferably administered in an oral daily dosage with Preferred and Most Preferred amounts of individual components as shown in the example below.

EXAMPLE

L-Arginine Ascorbate

| Ranges in milligrams per day | Including Excipients Compound | L-Arginine | Ascorbate |
|---|---|---|---|
| Preferred | 213 | 83 | 75 |
| to | 7113 | 2761 | 2500 |
| Most Preferred | 711 | 276 | 250 |
| to | 2845 | 1104 | 1000 |

3. L-Carnitine Complexes

Metal L-carnitine complexes included in the invention are used to increase the effectiveness, efficiency and safety of metformin in the prevention and treatment of progressive insulin resistance and diabetes mellitus. They have the following formulae:

[Car]C wherein,
a. Car is L-carnitine or bis-L-carnitine,
b. C is ascorbic acid or ascorbate, or

[Car]MX wherein,
a. Car is L-carnitine or bis-L,carnitine,
b. M is a metal ion taken from $Mg^{2+}$ or $Zn^{2+}$,
c. X is an anion taken from the group including hydroxides, halides, sulfates, phosphates, acetates, ascorbates or bis-ascorbic acid salts, or M[Car]

wherein,
a. M is a metal ion taken from $Mg^{2+}$ or $Zn^{2+}$,
b. Car is the amino acid L-carnitine or bis-L,carnitine.

The L-carnitine is preferably in the form of either (a) L-carnitine ascorbate, (b) bis-L-carnitine ascorbate, (c) an L-carnitine salt of either $Mg^{2+}$ or $Zn^{2+}$, (d) a bis-L-carnitine salt of either $Mg^{2+}$ or $Zn^{2+}$, or (e) a complex of L-carnitine or bis-L-carnitine, a metal ion that is either $Mg^{2+}$ or $Zn^{2+}$, and an anion that is either hydroxide, halide, acetate, or ascorbate.

The invention is a method for the oral administration of carnitine ascorbate or metallocarnitate complexes, alone or in combination, as a nutrient for humans. The cation of the metallocarnitate complexes may be $Mg^{2+}$ or $Zn^{2+}$.

The compound is preferably administered in an oral daily dosage with Preferred and Most Preferred amounts of individual components as shown in the example below.

EXAMPLE

Magnesium L-Carnitate

| Ranges in milligrams per day | Including Excipients Compound | Magnesium | Carnitine |
|---|---|---|---|
| Preferred | 44 | 2.3 | 30 |
| to | 1754 | 91 | 1200 |
| Most Preferred | 88 | 5 | 60 |
| to | 877 | 46 | 600 |

4. L-Taurine Complexes

L-taurine complexes included in the invention are used to increase the effectiveness, efficiency and safety of metformin in the prevention and treatment of progressive insulin resistance and diabetes mellitus. They have the following formulae:

[Tau]C wherein,
a. Tau is L-taurine or bis-L-taurine,
b. C is ascorbic acid or ascorbate, or

[Tau]MX wherein,
a. Tau is L-taurine or bis-L,taurine,
b. M is a metal ion taken from $Mg^{2+}$ or $Zn^{2+}$,
c. X is an anion taken from the group including hydroxides, halides, sulfates, phosphates, acetates, ascorbates or bis-ascorbic acid salts, or M[Tau]

wherein,
a. M is a metal ion taken from Mg or $Zn^{2+}$,
b. Tau is the amino acid L-taurine or bis-L,taurine.

The L-taurine is preferably in the form of either (a) L-taurine ascorbate, (b) bis-L-taurine ascorbate, (c) an L-taurine salt of either $Mg^{2+}$ or $Zn^{2+}$, (d) a bis-L-taurine salt of either $Mg^{2+}$ or $Zn^{2+}$, or (e) a complex of L-taurine or bis-L-taurine, a metal ion that is either $Mg^{2+}$ or $Zn^{2+}$, and an anion that is either hydroxide, halide, acetate, or ascorbate.

The invention is a method for the oral administration of taurine ascorbate or metallotarurate complexes, alone or in combination, as a nutrient for humans. The cation of the metallotaurate complexes may be $Mg^{2+}$ or $Zn^{2+}$.

The compound is preferably administered in an oral daily dosage with Preferred and Most Preferred amounts of individual components as shown in the example below.

EXAMPLE

Zinc Taurate

| Ranges in milligrams per day | Including Excipients Compound | Zinc | Taurate |
|---|---|---|---|
| Preferred | 51 | 7.9 | 30 |
| to | 2044 | 317 | 1200 |
| Most Preferred | 102 | 16 | 60 |
| to | 1022 | 158 | 600 |

5. Tocotrienol Nicotinate and Tocotrienol Picolinate

Tocotrienol complexes included in the invention are used to increase the effectiveness, efficiency and safety of metformin in the prevention and treatment of progressive insulin resistance and diabetes mellitus.

EXAMPLE

Tocotrienol Nicotinate

| Ranges in milligrams per day | Including Excipients Compound | Tocotrienol | Nicotinate |
|---|---|---|---|
| Preferred | 61 | 34 | 10 |
| to | 1844 | 1024 | 293 |
| Most Preferred | 307 | 171 | 49 |
| to | 1229 | 683 | 195 |

6. D,α-Tocopherol Nicotinate and D,α-Tocopherol Picolinate

D,α-Tocopherol complexes included in the invention are used to increase the effectiveness, efficiency and safety of metformin in the prevention and treatment of progressive insulin resistance and diabetes mellitus.

EXAMPLE

D,α-Tocopherol Nicotinate

| Ranges in milligrams per day | Including Excipients Compound | Tocopherol | Nicotinate |
|---|---|---|---|
| Preferred | 61 | 34 | 10 |
| to | 1844 | 1024 | 293 |
| Most Preferred | 307 | 171 | 49 |
| to | 1229 | 683 | 195 |

7. Propionylcarnitine Taurine Bi-Amide

This invention is a method for the oral administration of the bi-amide of propionylcarnitine and taurine, for the facilitation of mitochondrial fatty acid oxidation and ATP production. It is included in the invention and used to increase the effectiveness, efficiency and safety of metformin in the prevention and treatment of progressive insulin resistance and diabetes mellitus.

The compound is preferably administered in an oral daily dosage with Preferred and Most Preferred amounts of individual components as shown in the example below.

Propionylcarnitine-Taurine Amide

| Ranges in milligrams per day | Including Excipients Compound | propionylcarnitine | Taurine |
|---|---|---|---|
| Preferred | 97 | 46.2 | 25 |
| to | 3867 | 1849 | 1000 |
| Most Preferred | 193 | 92 | 50 |
| to | 1933 | 924 | 500 |

8. Peroxovanadate-Nicotinic Acid

This invention is a method for the oral administration of the bi-amide of peroxovanadate and nicotinic acid, for the facilitation of fatty acid oxidation and ATP production. It is included in the invention and used to increase the effectiveness, efficiency and safety of metformin in the prevention and treatment of progressive insulin resistance and diabetes mellitus.

The biofactors and the physiological activities listed above are reviewed in more specificity below.

PRESENT INVENTION

The present invention resides in pharmaceutical preparations to be used as adjuncts to pharmaceutical combinations of sulfonylurea and/or metformin in the treatment of progressive insulin resistance and type 2 diabetes. The preparation contains specific, sometimes unique, therapeutic biomolecules, biofactors and trace elements selected because of their particular and critical, combinational physiological effects in improving the safety and effectiveness of sulfonylurea and/or metformin therapy. These are formulated in amounts to achieve maximum complementarity of action.

Type 2 diabetes is preceded by a long period of impaired glucose tolerance and a reversible metabolic state associated with an increasing prevalence of macrovascular complications. Unfortunately, at the time of diagnosis, long-term complications have already developed in almost one fourth of these patients. Susceptibility to type 2 diabetes requires both genetic (most likely polygenic) and acquired factors. Its continuing pathogenesis involves interplay between progressive cellular insulin resistance and pancreatic β-cell failure. Any ideal treatment of type 2 diabetes must reduce insulin resistance and β-cell dysfunction in a majority of treated patients and, in addition, prevent, delay, or reverse long-term complications.

Sulfonylurea and/or metformin treatment reduces hyperglycemia and microvascular complications of the diseases, but fails to prevent macrovascular complications—indeed, such therapy may worsen macrovascular complications: sulfonylurea by promoting hyperinsulinemia; metformin by inducing hyperhomocysteinemia. It is unknown whether combinations of these drugs will result in a summation of these effects.

The therapeutic strategy of the invention is founded upon the modification of multiple pathophysiological processes by innovative combinations of biomolecules, biofactors and trace elements with distinct, but complementary or synergistic, mechanisms of action in order to provide a safe and effective adjunct to ongoing sulfonylurea and/or metformin therapy. The invention clinically expands the effect of this therapy by preventing both diabetic microvascular complications (nephropathy, neuropathy, retinopathy) and diabetic macrovascular complications (heart attack, stroke, peripheral vascular disease).

This invention physiologically complements the clinical use of sulfonylurea and/or metformin by improving the disturbed mitochondrial function that occurs as a result of this treatment, and by preventing the disturbance of plasma and mitochondrial membrane integrity that leads to vascular diabetic complications.

The complexity of progressive insulin resistance and type 2 diabetes pathophysiology, and the nature of the effect of either or both sulfonylurea and of metformin on the disease process, provides an opportunity to improve the clinical value of these drugs and reduce devastating long-term diabetic complications. By the administration of an adjunct, complementary combination of biomolecules, biofactors and trace elements, many of which are deficient or functionally inadequate in progressive insulin resistance and type 2 diabetes, and which are inadequately moderated or worsened by sulfonylurea and/or metformin treatment, the clinical usefulness of the latter will be expanded.

The invention will: (1) improve disturbed mitochondrial function, (2) increase insulin receptor sensitivity, amplifying the sulfonylurea-metformin ability to reduce hyperglycemia, (3) modify diabetic post-receptor disturbances, including deleterious types of $Ca^{2+}$ signaling, (4) reduce plasma and mitochondrial membrane damage from free radicals, (5) optimize repolarization of the β-cell as required for a continued sulfonylurea effect, (6) protect pancreatic β-cells from premature apoptosis, (7) reduce the deleterious metformin induced elevated homocysteine, (8) lessen non-enzymatic glycation and, (9) prolong the timeframe over which sulfonylurea and/or metformin treatment is useful.

COMPONENTS OF THE INVENTION

The components within the invention are those that have substantial and varied complementarity. For a variety of reasons, many of the components are deficient in persons with insulin resistance and in diabetic patients. $Mg^{2+}$, ascorbate, chromium and certain amino acids (viz., carnitine, taurine) are important examples of such diabetic deficiencies, either because of inadequate intake or pathologic depletion.

L-arginine

L-arginine is usually limited in insulin resistance syndrome and type 2 diabetes; an insufficiency that can be overcome by dietary supplementation.

L-arginine is the substrate required for NO synthesis via the endothelial enzyme Type III NOS, leading to the formation of cyclic GMP, the messenger of NO's physiological effects. NO is a chemically unstable radical formed by enzymatic conversion of L-arginine in the presence of molecular oxygen. It elicits relaxation of vascular smooth muscle cells (VSMC) by activating cytosolic guanylate cyclase, the enzyme involved in cGMP production. In addition to its pivotal role in vasodilation, NO inhibits platelet and leukocyte adhesion to endothelial cells, inhibits platelet aggregation and facilitates the dissolution of small platelet aggregates. NO also affects fibrinolytic activity by regulating the release of tissue-type plasminogen activator from the vascular endothelial cells and plasminogen activator inhibitor-1. These biological actions make NO a key substance in the endogenous defense against vascular occlusion and thrombosis, and in improving the dynamic and Theological vascular responses in patients with insulin resistance syndrome and/or type 2 diabetes.

Metformin and L-arginine are complementary in modulating endothelial function by normalizing constitutive NO production. This enhances the antihypertensive effects evident in some individuals, and reduces the hypertensive and thrombogenic effects in those individuals in whom metformin induces hyperhomocysteinemia. Furthermore, metformin and L-arginine are complementary in decreasing both platelet aggregation and blood viscosity.

Activation of ATP sensitive $K^+$ channels (K(ATP)) and the NO-cGMP pathway both reduce norepinephrine (NE) release from cardiac sympathetic nerves during stimulation. In this regard NO and sulphonlyurea-sensitive channels act in a complementary fashion, but appear to be independent of each other in the regulation of heart rate during cardiac sympathetic nerve activation.

As noted above, sulfonylurea treatment can induce coronary vasoconstriction and reduce coronary blood flow at rest by about 25%, but does not reduce flow during exercise, providing the L-arginine-cNOS-NO-cGMP pathway is normal. Increased perfusion pulsatility, as accompanies exercise, offsets vasoconstriction from sulfonylurea-induced $K^+$ ATP-channel blockade. And the channel blockade is reduced by nitric oxide synthase (eNOS) and constitutive NO release from the vascular endothelium. This effect is mediated by A(2A) receptors, activation of which elicit the vasodilation by endothelial release of NO and by the smooth muscle opening of K(ATP) channels.

In addition, L-arginine stimulates insulin secretion via NO and improves insulin sensitivity at the receptor via eNOS. Each of these L-arginine actions augments sulfonylurea therapy: The former as an insulin secretogue, an effect that complements sulfonylurea; the latter by increasing peripheral insulin sensitivity, which both complements and extends the effects of combined sulfonylurea-metformin on glycemic control.

Treatment with L-arginine inhibits lipid peroxidation, additionally protecting the endothelium and reducing long-term microangiopathic complications in insulin resistance syndrome and type 2 diabetes.

Finally, it is reasonable to expect that L-arginine like Viagra® will have a favorable effect on the digestive disorders of diabetics, including perhaps, a reduction in the gastrointestinal side effects of sulfonylurea-metformin.

When L-arginine is administered it increases the effectiveness, efficiency, and safety of combined sulfonylurea-metformin in the prevention and treatment of insulin resistance and diabetes mellitus.

Ascorbic Acid

Diabetics have at least 30% lower circulating ascorbic acid concentrations than people without diabetes mellitus. The cellular uptake and cellular level of vitamin C (ascorbic acid, AA) is promoted by insulin and reduced in insulin resistance and hyperglycemia. Additionally, AA is excessively lost via the diabetic kidney.

Ascorbic acid is a cofactor of two-enzyme hydroxylation in the pathway of carnitine biosynthesis . . . epsilon-N-trimethyllysine hydroxylase and gamma-butyrobetaine hydroxylase. Carnitine levels are reduced in individuals with subnormal (although still non-scorbutic) AA status, providing evidence that metabolic changes occur prior to the classic manifestation of scurvy. In addition to the evident diabetic angiopathies and dyslipidemia derived directly from inadequate carnitine, the symptoms of weakness and fatigue often seen in progressive insulin resistance and type 2 diabetes may relate to carnitine deficient mitochondrial dysfunction, indirectly due to inadequate cytosolic AA.

The hydrophilic scavengers, ascorbate and GSH, are found in mitochondrial compartments. They scavenge oxidizing free radicals in these mitochondrial water compartments by means of one-electron or hydrogen atom transfer.

Mitochondria are cellular organelles in which the generation of reactive oxygen species (ROS) is high and in which ROS production greatly multiplies during pathological processes such as diabetes. Normally ROS are effectively protected against by the high capacity of inherent antioxidative systems: enzymes and water- or lipid-soluble low molecular weight antioxidants. The latter defense systems can be regenerated after or during oxidative stress, as long as the mitochondria are in an energized state. The energizing of mitochondria mainly depends on the availability of suitable respiratory substrates that provide hydrogen for the reduction of either the GSH or α-tocopherol system. GSH is regenerated by glutathione reductase with the substrate NADPH and the α-tocopheroxyl-radical by reduced coenzyme Q or ascorbate. Mitochondria do not undergo damage as long as they can keep a high-energy state. The delicate balance between prooxidative/antioxidative activities can be shifted rapidly towards oxidation if prooxidants exist—such as excessive levels of ascorbate—especially in the presence of iron. After exhaustion of their antioxidative defense systems, damage of mitochondrial membranes finally occurs leading to total degradation of the mitochondria. The formulations of this invention provide supplements in amounts and schedules to provide ascorbate sufficient to avoid its deficiency, but not at excessive, potentially prooxidant levels.

ROS have been implicated in a variety of pathological processes. The generation of highly reactive oxygen metabolites is an integral feature of normal cellular metabolism (mitochondrial respiratory chain, phagocytosis, arachidonic acid metabolism, ovulation and fertilization), however their production can multiply during pathological circumstances. Free oxygen radicals act either on the extracellular matrix or directly upon cellular membranes themselves. The fundamental defenses of the organism against ROS include scavenger enzymes (superoxide dismutase, catalase, glutathione peroxidase) and lipid- and water soluble antioxidant compounds (ascorbic acid, glutathione, albumin, transferrin, etc.). Their role in ischemia-reperfusion models has now been comprehensively investigated and it has become clear that ROS are to be blamed for the bulk of post-ischemic injuries, hence the basis for newly established antioxidant therapy in such cases. Also, more and more studies have concluded a pivotal role of ROS in degenerative and inflammatory conditions, post-radiation processes and aging.

While the free radical scavenging abilities of AA are well established, its complementary actions for free radical defense with other components of the this invention may be less well known: with taurine for HOCl-defense; with GSH for hydrogen peroxide defense; and with $Zn^{2+}$ for superoxide defense.

Insulin is readily glycated and secreted from insulin secreting β-cells under hyperglycemic conditions; the extent of insulin glycation increasing in relation to the level of hyperglycemia, attaining levels up to 27%. Such glycation interferes with its function at the insulin receptor. Cellular insulin glycation is decreased by 66–80% by ascorbate. The reduction of hyperglycemia secondary to the use of long-term treatment with combinations of sulfonylurea-metformin is also associated with a decrease in the extent of insulin glycation. This evidences one of the important complementary actions of sulfonylurea-metformin and ascorbate that is lost in AA deficient patients.

Ascorbic acid is not only a powerful antioxidant in the cytosol, but is also a cofactor in collagen biosynthesis and an inhibitor of platelet activation, prostaglandin synthesis and the polyol (sorbitol) pathway. The latter is of particular importance in reducing microvascular permeability and non-enzymatic protein glycation.

Because free radicals are released from the autooxidation of glucose, hyperglycemia induces oxidative free radical stress. AA has been shown to be highly consumed in diabetes, presumably through free radical scavenging. If a continuous supply of AA is available, it indirectly maintains appropriate levels of other free radical scavengers, particularly intracellular GSH, thus complementing sulfonylurea-metformin GSH preserving action.

AA exhibits an important synergism with α-tocopherol (which is shared by two other components of this invention: lipoic acid, and ubiquinone) and is complementary to L-arginine in lessening endothelial dysfunction by normalizing constitutive NO production in patients with insulin resistance syndrome and/or type 2 diabetes. This action of AA improves impaired acetylcholine-induced vasodilation by a mechanism linked to NO formation. AA selectively restores impaired endothelium-dependent vasodilation even in patients with insulin-dependent diabetes mellitus In addition to causing oxidative stress, hyperglycemia—via glycation of proteins—generates Maillard products that cross-link. These advanced glycation products occur in vivo in diabetes mellitus as well as in aging. Activation of the polyol (sorbitol) pathway leads to such nonenzymatic protein glycation that causes thickening of basement membrane and proliferation of endothelium cells. AA lessens nonenzymatic glycation principally because of its aldose reductase activity and consequent inhibition of the polyol pathway.

Besides preventing endothelial dysfunction by scavenging free radicals, AA increases levels of the eNOS cofactor BH4 and thus the bioavailability of NO. The latter effect appears to be independent of the ability of AA to scavenge directly superoxide anions and other FR. BH4 is itself an antioxidant, which like tocopherol may be regenerated by AA. Likewise, GSH may affect constitutive NOS kinetics by recycling or preventing the autooxidation of BH4. Thus, eNOS activity depends on both BH4, the reduced state of essential protein thiols and the ready availability of AA. This further illustrates the interrelated pathophysiological nodes that this invention identifies and influences, the better to enhance and expand the effectiveness of metformin.

Tetrahydrobiopterin (and its Biosynthetic Precursors in this Invention: 7,8-Dihydroneopterin; 1'-hydroxy-2'-Oxopropyltetrahydropterin; L-Sepiapterin, 7,8-Dihydrobiopterin; Pyruvoyltetrahydropterin; Lactoyltetrahydropterin.)

Tetrahydrobiopterin (BH4) is one of the most potent naturally occurring reducing agents and is an essential cofactor for the enzymatic activity of eNOS. Suboptimal concentration of BH4, as occurs in diabetes, reduces formation of NO and "uncouples" eNOS leading to an eNOS-mediated reduction of oxygen, the formation of superoxide anions and of hydrogen peroxide.

Put differently, eNOS catalysis results in either the formation of NO or of superoxide depending on the presence or absence of BH4. Although eNOS releases NO, which regulates vascular tone under normal conditions, eNOS produces the superoxide anion and hydrogen peroxide when either its required cofactor BH4 or when L-arginine, is decreased. Thus, eNOS may become a direct source of reactive oxygen species under pathological conditions such as diabetes, when either or both may be lacking. Because NO reacts with the superoxide anion and hydrogen peroxide to form peroxynitrite, singlet oxygen and the hydroxyl radical, any simultaneous release of NO and reactive oxygen species in the presence of inadequate concentrations of BH4 (and/or L-arginine) is toxic. An increase in BH4 in cells reduces this eNOS dysfunction and protects the cells against related cell injury. The concomitant addition of L-arginine and BH4 has been shown to abolish superoxide generation by eNOS.

Recent findings suggest that accelerated catabolism of BH4 in arteries exposed to oxidative stress contributes to the pathogenesis of the endothelial dysfunction known to exist in the arteries of diabetics; unfortunately, elevated glucose prevents an increase in cellular levels of BH4. Fortunately, in animals and humans, experimental supplementation of BH4 has demonstrated beneficial effects on endothelial function. This benefit may exist because it appears that the beneficial effects of some antioxidants (e.g., vitamin C) on vascular function are mediated via increased intracellular concentration of BH4.

Insulin resistance decreases vascular relaxation secondary to impaired eNOS activity and increased oxidative breakdown of NO from the enhanced formation of superoxides (the latter resulting from a deficiency of BH4 in vascular endothelial cells). The consequent hypertension of insulin resistance is associated with an attenuated endothelium-dependent vasodilatation to acetylcholine. This is improved by concomitant oral treatment with BH4: Further evidence that endothelial function—for good or ill—in insulin resistance and Type II diabetes is modulated by the availability of BH4

Carnitine (L-carnitine and Congeners in this Invention: acetyl-L-carnitine; propionyl-L-carnitine; propionylcarnitine taurine amide; butyrylcarnitine taurine amide)

Carnitine levels are reduced in diabetes, and are further decreased by sulfonylurea treatment.

Carnitine (beta-hydroxy-gamma-N-trimethylaminobutyric acid) is required for transport of long-chain fatty acids into the inner mitochondrial compartment for beta-oxidation. Carnitine is required for the mitochondrial energy system to function efficiently. Its deficiency leads to reduced fatty acid oxidation and limited mitochondrial ATP (energy) production. This is of particular importance for the heart since it depends on fatty acids as its primary fuel. If the heart is denied adequate fatty acids transport into the mitochondria by carnitine to supply its energy need, glucose is used as the backup fuel; however, glucose may not provide sufficient energy for normal cardiac function, especially in progressive insulin resistance and type 2 diabetes. This can lead to severe cardiac arrhythmias, cardiac arrest and death. In addition, the excessive exposure of tissues to fatty acids, which occurs in carnitine deficiency, is one of the causes of progressive insulin resistance, and this problem is compounded when the existing carnitine deficiency reduces ATP propelled pancreatic production of insulin.

Widely distributed in foods from animals but not plants, carnitine is also synthesized endogenously in the liver and kidney from two essential amino acids, lysine and methionine. Human skeletal and cardiac muscles contain relatively high carnitine concentrations, which they receive from the plasma, since they are incapable of carnitine biosynthesis themselves.

As stated, carnitine is deficient in type 2 diabetes, and further depleted by sulfonylurea treatment. It is surprising that this important adverse effect—sulfonylurea— induced carnitine deficiency—is seldom referred to. This is especially true when one considers that a major disappointment of sulfonylurea therapy is that it fails to prevent the macrovascular complications of type 2 diabetes, presumably, in part because of its adverse effect on carnitine homoeostasis.

Sulfonylurea treatment inhibits the physiologic renal resorption of carnitine, and also adversely affects carnitine metabolism by inhibiting acetyltransferase activity in liver microsomes, thereby inducing the macrovascular complications associated with carnitine deficiency, which are the same as the macrovascular complications of type 2 diabetes: heart attacks, stroke and peripheral vascular disease. Additionally, the reperfusion injury that occurs after a macrovascular ischemic event is worse in carnitine deficient patients and is less severe in patients who have normal tissue levels at the time of the ischemic event. The clinical recovery after an ischemic event, like a heart attack, is improved if the patient is not carnitine deficient at the time of the myocardial infarction.

This results in a vicious cycle in which patients with coronary artery disease, either with prolonged periods of myocardial ischemia or with short-term mild myocardial ischemia, have a significant loss of cardiac carnitine with an overall net decrease in myocardial carnitine content, which further increases the heart's vulnerability to ischemia and further reduces its capacity to recover from infarction.

Serious results from heart attacks, the leading cause of death in type 2 diabetes, can be divided into cardiomyopathy, if the area of damage is sufficiently large that the heart can no longer function as a pump, and/or potentially fatal cardiac arrhythmias, if the pacemaker cells are damaged. Carnitine is beneficial in prevention and amelioration of both of these heart attack-induced pathologies; indeed, carnitine deficiency alone can actually cause cardiomyopathy in the absence of myocardial infarction.

Myocardial and peripheral ischemia in man are associated with the activation of circulating neutrophils and platelets. Carnitine inhibits the synthesis of platelet activating factor (PAF) from human neutrophils and platelets, thus exerting a protective effect in tissue ischemia and in other diseases associated with neutrophil and platelet activation, such as atherosclerosis.

Enhancement of hepatic fatty acid oxidation by carnitine has considerable clinical potential in patients with both insulin resistance and type 2 diabetes although this same activity also tends to enhance hepatic gluconeogenesis, limiting its usefulness to some extent. However, as an adjunct to metformin there is reciprocal complementarity: carnitine's stimulation of gluconeogenesis is negated by the biguanide, and metformin's ability to improve insulin sensitivity is enhanced by carnitine. That they each lead to reduced body weight in at-risk, obese patients is an added complement, making a combination of metformin and carnitine especially valuable.

Oral treatment with carnitine improves not only the function of cardiac muscle but also of retina and peripheral nerves It improves diabetic nerve conduction velocity (NCV) peripherally and in the retina. Carnitine improves diabetic neuropathy and retinopathy without influencing the polyol pathway, perhaps by modulating myoinositol and reducing the serum triglyceride level.

Implementation of mitochondrial fatty acid oxidation with ATP production by carnitine is of enormous physiologic importance, and its deficiency in pathologic states such as progressive insulin resistance and type 2 diabetes worsens the outlook. Carnitine is safe and, except for a tendency to increase hepatic gluconeogenesis, it has no side effects of note in these disease states.

Carnitine is absorbed by both active transport and passive diffusion in the duodenum and jejunum. Variable amounts are absorbed from the intestine, ranging from 15 to 87% of ingested carnitine, in part depending on the ongoing level of cellular (liver, kidney) synthesis of carnitine. Carnitine is not synthesized in either skeletal or cardiac muscle, which contain more than 90% of the total body carnitine; each being dependent entirely on carnitine uptake from the blood. This uptake occurs via an active transport system, which allows tissue concentrations to be 20- to 50-fold higher than in the plasma.

Carnitine reaches its plasma levels slowly, still rising two hours after oral administration. Absorption via the portal vein is followed by hepatic extraction and appearance in bile with resorption of a fraction, thus establishing an enterohepatic circulation.

Carnitine enters the cell from the plasma slowly; thus oral therapy does not cause rapid repletion of body stores of carnitine. Oral administration of carnitine requires continuous use to achieve and maintain its important physiological effects.

When L-carnitine is administered as an adjunct, it increases sulfonylurea-metformin effectiveness, efficiency, and safety in the prevention and treatment of progressive insulin resistance and type 2 diabetes, reduces the cardiovascular risks associated with these diseases and reduces adverse side effects which arise from the combined use of these therapeutic agents.

Choline (2-Hydroxy-N,N,N-trimethylethanaminium)

Choline provides an essential structural component of many biological membranes. It affects the mobilization of fat from the liver and is essential for the formation of the neurotransmitter acetylcholine. Of particular importance, as a component of this invention, choline maintains serum carnitine concentrations by conserving urinary carnitine, thus counteracting a significant adverse effect of sulfonylurea. It also reduces the homocysteine risk of metformin by transferring one of its methyl groups to homocysteine to form methionine, thereby lessening the threat of homocysteine-induced thrombosis in diabetes.

Choline is important in the diet to stimulate removal of excess fat from the liver (lipotropic), thereby reducing the indirect "obesity adverse effect" of sulfonylureas and complimenting the weight control advantage of metformin. Although choline can be made in the body, its synthesis is limited.

Oral administration of choline is effective reaching the blood circulation without losing its activity. The needs of the tissues for choline are met from both exogenous (dietary) and endogenous (metabolic) sources. Biosynthesis of choline occurs by transmethylation of ethanolamine with the methyl group of methionine, or by a series of reactions requiring vitamin $B_{12}$ and folate as cofactors.

Chromium

There is a dietary deficiency of Chromium (Cr) in more than one-half of the USA population.

Cr is a cofactor for insulin: it increases insulin binding to its receptor, thereby reducing cellular insulin resistance. Cr not only improves insulin binding, it also: increases the number of insulin receptors, improves insulin internalization by endocytosis from caveolae, increases β-cell sensitivity and increases insulin receptor enzymes resulting in an overall increase in insulin sensitivity.

Cr is known to be an essential nutrient for normal sugar and fat metabolism. Insufficient dietary Cr has been associated with the development of the insulin resistance syndrome and of type 2 diabetes, and with their associated cardiovascular diseases. This dietary shortfall has been exacerbated by the worldwide increase intake of refined foods that not only contain little Cr, but also simultaneously increase Cr excretion.

Cr supplementation improves the diabetic control afforded by exercise. Supplements of chromium nicotinate or picolinate complexes lower blood sugar, LDL cholesterol and increase lean body mass. Cr supplementation can reduce metformin requirements by more than one-half.

N-acetyl-L-Cysteine

N-acetylcysteine (NAC) is a GSH prodrug, an independent antioxidant, and promotes the synthesis of the glycosaminoglycan heparan sulfate.

stated above, the tripeptide GSH is insufficiently absorbed from oral dosage forms, and therefore any supplementation must be from prodrugs like N-acetyl-cysteine or α-lipoic acid, both of which are satisfactorily absorbed from the gastrointestinal tract.

NAC is a very good antioxidant itself with a notable effect in preventing endothelial dysfunction, and it reduces the paradoxical vasoconstriction effect of acetylcholine on VSMC that occurs when adjacent endothelial cell are damaged. Perhaps more important in this context is its role as an orally available source for GSH synthesis.

Cysteine is the essential sulfur-containing amino acid in GSH. NAC increases systemic GSH by supplying the necessary cysteine intracellularly. GSH and glutathione peroxidase levels are notably reduced in progressive insulin resistance and type 2 diabetes. The deficiencies and the associated peroxide-mediated damage to cell membranes may appear early in the progressive insulin resistance and type 2 diabetes, before the development of secondary complications. Additionally, GSH counterbalances the effects of ICAM-1, one of the most important intercellular adhesion molecules involved with the atherogenesis associated with insulin resistance syndrome and type 2 diabetes. GSH similarly reduces thrombin activation, which results from hyperglycemia.

GSH acts in concert with ascorbate to inhibit the reaction between superoxide and excessive NO, which produces the cell membrane damaging peroxynitrite. In addition, GSH stimulates superoxide dismutase (SOD) an activity that further reduces the toxic effects of the superoxide radical. And furthermore, GSH supplies the substrate for glutathione peroxidase, which quenches hydrogen peroxide and reduces its conversion to OH⁻ (a highly toxic radical). It also lessens RBC microviscosity, thus augmenting blood flow in the microvasculature. It's easy to see why it is reasonable to concede the title of the most important intracellular free radical defense to GSH.

Separate from its importance as a GSH prodrug, NAC, as a sulfur-containing amino acid, promotes the synthesis of heparan sulfate. The importance of synthesizing heparan sulfate to maintain the structural and anionic charge of the vascular endothelial basement membrane cannot be overemphasized; failure in this area, induced by hyperglycemia, is the root cause of the blindness of diabetic retinopathy and the mortality of diabetic nephropathy.

The antioxidant abilities of NAC and other elements of this invention, have the potential to delay the onset and delay the progression of "type 1.5 diabetes". In the latter, ROS destroy pancreatic β-cells. This β-cells destruction results in the addition of insulin-dependent (type 1) diabetes mellitus clinical findings to those already existing from type 2 diabetes. Activation of NFkappaB by ROS-induced release of mitochondrial cytochrome C seems to be the key cellular signal in initiating a cascade of events leading to β-cell death in this scenario. Thus, enhancement of pancreatic GSH (via oral administration of the prodrug NAC or α-lipoic acid)—a key intracellular regulator of NF-kappaB—affords protection against the insidious onset of "type 1.5 diabetes". In this context, supplementation with 500 mg/kg of NAC as a GSH precursor, has been shown to inhibit alloxan-induced NFkappaB activation, and subsequently reduce hyperglycemia. By inference, NFkappaB activation by ROS (via the mitochondria) may initiate a sequence of events eventually leading to type 1 diabetes, by way of "type 1.5 diabetes": In one study, inhibition of NF-kappaB activation by NAC has been shown to attenuate the severity of type 1 diabetes.

Folic Acid

Homocysteine (Hcy) is a notable contributor to hypertension and thromboangiogenesis. Folic acid administration reduces the circulating Hcy levels that are adversely elevated by metformin treatment.

Mitochondrial abnormalities have been identified in hepatocytes of patients with hyperhomocysteinemia, however, the mechanism by which homocysteine affects mitochondria is not entirely established. Homocysteine and $H_2O_2$, but not $H_2O_2$ alone, cause decreases in mitochondrial RNA levels and catalase. This provides evidence that homocysteine and $H_2O_2$ act synergistically to cause mitochondrial damage. There is some evidence that intracellular GSH plays a role in protecting mitochondria against the adverse effects elicited by this combination of homocysteine and $H_2O_2$. The importance of avoiding folic acid deficiency and secondary hyperhomocysteinemia and mitochondrial damage is evident.

Less well known is that homocysteine inhibits the expression of heparan sulfate, which may contribute to its thrombogenic property, which also potentially exacerbates the diminished heparan sulfate synthesis commonly observed in diabetes (See above.). A circular problem is therefore initiated in diabetes: homocysteine reduces heparan sulfate in the glomerulus, which leads to renal malfunction, which in turn leads to hyperhomocysteinemia, which aggravates the hypertension and thromboangiogenesis of diabetes, etc.

Hyperhomocysteinemia is associated with macrovascular disease in a significant proportion of patients with type 2 diabetes. Furthermore, this hyperhomocysteinemia is related to 5-year mortality rates independent of other major risk factors, and is a stronger (1.9-fold) risk factor for mortality in type 2 diabetic patients than in nondiabetic subjects.

Inadequate heparan sulfate in the microvascular basement membrane reduces the basement membrane's negative charge that is essential for its structural integrity; the latter results in the vascular leakage associated with the devastating microangiopathies of diabetes.

Folic acid is well absorbed and rapidly converted to tetrahydrofolic acid, the active coenzyme for intracellular metabolism. Tetrahydrofolate is required as a methyl donor for the conversion of homocysteine to methionine. Plasma levels of homocysteine are thus lowered by folic acid, directly reducing the potent vasoconstrictive, endothelial cytotoxicity, vascular basement membrane failure and thrombotic effects of homocysteine.

Diabetes significantly lowers folate in kidney, heart, brain, and muscle. The addition of metformin worsens this loss. For this reasons adjunct folate supplementation to combined treatment with sulfonylurea-metformin in progressive insulin resistance and type 2 diabetes is logical.

α-Lipoic Acid

α-Lipoic acid is an important adjunct in sulfonylurea-metformin treatment for insulin resistance syndrome and type 2 diabetes. It increases insulin sensitivity, prevents depletion of GSH, limits protein glycation and attenuates NFkappaB transcription.

α-Lipoic acid improves insulin-responsive glucose utilization, demonstrating a positive effect on insulin-stimulated glucose uptake, and it is a potent antioxidant in both fat- and water-soluble media. Furthermore, its antioxidant activity extends to both the oxidized and the reduced form. α-Lipoic acid regenerates AA from dehydroascorbic acid and indirectly regenerates α-tocopherol. It increases intracellular GSH and limits protein glycation. It has the potential favorably to modify diabetes and reduce diabetes-induced complications, particularly diabetic neuropathy.

Hyperglycemia induces neuronal dysfunction via at least three secondary biochemical disturbances—the sorbitol (polyol) pathway, the non-enzymatic glycation of proteins and oxidative stress—and there are clear interactions between all three. Because of these interactions, interference with one of these biochemical transducers worsens or attenuates the effects of the others. Pharmacological intervention should consist of a combined attack on all these sources of disturbance. α-Lipoic acid has the potential to correct effects arising from multiple pathways of disorder in experimental diabetic neuropathy.

Depletion of cellular antioxidant defense mechanisms in the face of increased generation of oxygen free radicals by advanced glycation end products (AGEs) play a major role in the pathogenesis of diabetic vascular complications. The endothelial migration of monocytes is one of the first steps in atherogenesis and monocyte-endothelial interaction itself is linked to the expression of adhesion molecules like vascular cell adhesion molecule-1 (VCAM-1). Stimulation of VCAM-1 by AGEs has been demonstrated. Supplementation of the cellular antioxidative defense with the natural occurring antioxidant α-lipoic acid before AGE albumin induction, prevents the AGE albumin-dependent depletion of reduced GSH and AA. α-lipoic acid seems to reduce AGE albumin-induced NF-kappaB mediated transcription and the expression of relevant endothelial genes in diabetes. Among others these include, tissue factors for VCAM-1 and for endothelin-1. Thus, in vitro supplementation of cellular antioxidative defense mechanisms by extracellularly administered α-lipoic acid reduce AGE albumin-induced endothelial dysfunction.

α-Lipoic acid attenuates NFkappaB, a key cellular signal that initiates a cascade of events leading to β-cell death. This, plus α-lipoate's enhancement of pancreatic GSH, affords protection against progression from type 2 diabetes to "type 1.5 diabetes".

When α-Lipoic acid is administered it increases the effectiveness, efficiency, and safety of sulfonylurea-metformin combinations in the prevention and treatment of insulin resistance and diabetes mellitus and expands the scope of sulfonylurea-metformin treatment to include macrovascular diabetic complications. Sulfonylurea-metformin pharmacokinetics do not appear to be altered by lipoic acid in any clinically meaningful extent. Plasma insulin and glucose concentrations did not indicate any interaction between α-lipoic acid and sulfonylurea, or of α-lipoic acid and acarbose. Coadministration of single doses of α-lipoic acid and sulfonylurea-metformin appear to be safe and not cause drug-drug interactions Magnesium Magnesium ($Mg^{2+}$) used as an adjunct to combined sulfonylurea-metformin use should improve hepatic and peripheral insulin sensitivity (where sulfonylurea has no apparent beneficial effect and metformin has only a modest effect), avoid defective tyrosine-kinase activities at the insulin receptor, optimize cytoplasmic free $Ca^{2+}$ levels, reestablish cell membrane polarization after sulfonylurea action, and enhance the sulfonylurea insulin secretagogue effect: each of these adds to the therapeutic effectiveness of sulfonylurea-metformin.

Sulfonylurea receptors have a unique function in many areas of membrane physiology. They are responsive to modulation by inhibition and by stimulation by magnesium-nucleotides. This underlines the importance of $Mg^{2+}$ in determining the reactiveness of sulfonylurea on ion channels. There is laboratory evidence that the effect of sulfonylurea is optimized when adequate levels of intracellular $Mg^{2+}$ are present.

Oral magnesium hydroxide enhances the absorption of sulfonylurea. The possibility that $Mg^{2+}$, delivered in an oral dosage form, could decrease the required dose of sulfonylurea is encouraging, in that it could reduce the gastrointestinal intolerance experienced by some patients.

The American Diabetes Association recommends that all patients with normal renal function who have hypomagnesemia and diabetes mellitus receive $Mg^{2+}$ supplementation. This represents a majority of patients with progressive insulin resistance or type 2 diabetes. $Mg^{2+}$ deficiencies are widespread in the progressive insulin resistance and type 2 diabetes. Patients receiving sulfonylurea exhibit little change in urinary excretion of $Mg^{2+}$ yet they show a significant rise in serum $Mg^{2+}$. Metformin has been described as one of the mechanisms involved in the induction of hypomagnesemia although not all studies support this view. As an example: Poorly controlled type 2 diabetic patients with hypomagnesemia, hypermagnesuria, and hypercalciuria were treated with metformin. Glycemic control was improved, as assessed by glucose and hemoglobin A1. A reduction in $Mg^{2+}$ renal excretion resulted from the metformin treatment, but patients remained hypomagnesemic and hypercalciuric.

While the combined effect of sulfonylurea and metformin on magnesium levels is unclear, their pharmacodynamic complementarity for patients with progressive insulin resistance or type 2 diabetes is fortunate, since both hyperinsulinemia and hyperglycemia can result in hypomagnesemia, which in turn increases insulin resistance—another vicious cycle.

Hypomagnesemia occurs in 25–38% of patients with type 2 diabetes. Current dietary amounts of $Mg^{2+}$ are marginal. The average dietary intake of 450 to 485 mg per day of $Mg^{2+}$ in the USA at the turn of the century has now decreased to about one-half of this. There now exists a general population dietary $Mg^{2+}$ shortfall of 90 to 180 mg per day. Unfortunately for patients with insulin resistance and type 2 diabetes, circulating insulin (and perhaps proinsulin) induce an increase in the renal excretion of $Mg^{2+}$. This might partly explain the $Mg^{2+}$ depletion observed in various hyperinsulinemic states.

A $Mg^{2+}$ deficient state (and a rise in cellular free $Ca^{2+}$) appears to cause insulin resistance, with the plasma $Mg^{2+}$ level inversely related to insulin sensitivity. Insulin-resistant states generally are characterized by the accumulation of cytosolic free $Ca^{2+}$ and the depletion of free $Mg^{2+}$. $Mg^{2+}$ supplementation should improve both insulin sensitivity and insulin secretion in patients with type 2 diabetes.

Decreased cellular $Mg^{2+}$ concentrations represent a risk factor in the pathogenesis of both microvascular and macrovascular complications of diabetes. Low serum and dietary $Mg^{2+}$ may be related to the etiologies of CVHD, hypertension, and atherosclerosis as well as progressive insulin resistance and type 2 diabetes. One of the most serious complications of diabetes, cardiac irregularity, including ventricular ectopic beats, is associated with decreased intracellular $Mg^{2+}$.

Elevated levels of serum glycosaminoglycans (GAG), associated with hypomagnesemia were observed in patients with coronary artery disease and thrombotic stroke. Serum lipid profiles are normal in the majority of these patients, indicating that elevated serum GAG may be an even more reliable indicator of atherosclerosis than elevated serum total cholesterol or LDL cholesterol. The implication of this observation is that GAG escape from the basement membrane in hypomagnesemia, thereby lessening its normal anionic charge and antithrombotic character, and that $Mg^{2+}$ deficiency may be one of the factors involved in the increased serum level of GAG.

Intracellular $Mg^{2+}$ levels may mediate the effects of reduced GSH and α-tocopherol on glucose metabolism. α-tocopherol has been demonstrated to improve insulin action. Recent evidence also suggests that α-tocopherol enhances GSH levels and may play a protective role in $Mg^{2+}$ deficiency-induced cardiac lesions. This clinical link between α-tocopherol, cellular $Mg^{2+}$, GSH, and tissue glucose metabolism certainly illustrates the importance of $Mg^{2+}$, but it more importantly illustrates the synergistic and synergetic relationships that can (and must) be addressed by approaching insulin resistance and type 2 diabetes as nonlinear complexities, as is done by this invention.

In addition to complementary effects of $Mg^{2+}$ with α-tocopherol and GSH in diabetes, similar synergisms for $Mg^{2+}$ have been defined with taurine, carnitine and vanadium, and with sulfonylurea-metformin.

Intracellular $Mg^{2+}$ concentration modulates insulin actions that offset $Ca^{2+}$-related, excitation-contraction coupling. $Mg^{2+}$ functions both intracellularly and extracellularly to optimize the cytoplasmic free $Ca^{2+}$ level. Excess cytoplasmic free $Ca^{2+}$ has the deleterious effect of leading to an increase in ET-1 with its associated decrease in blood flow and increase in apoptosis.

The inadequate intracellular $Mg^{2+}$ concentration often found in progressive insulin resistance and type 2 diabetes results in defective tyrosine-kinase activities at the insulin receptor level and exaggerated intracellular $Ca^{2+}$ concentration. Daily $Mg^{2+}$ administration to type 2 diabetes patients restores intracellular $Mg^{2+}$ concentration and can contribute to improved insulin-mediated glucose uptake.

In some studies, the correction of $Mg^{2+}$ deficiency exerts additional antihypertensive, anti-atherosclerotic, anti-arrhythmic and antithrombotic effects, addressing the failure of sulfonylurea-metformin in preventing macrovascular diabetic complications, while complementing them in reducing microvascular diabetic complications.

$Mg^{2+}$ is an important component in formulations designed as adjunctive to combined sulfonylurea-metformin therapy.

The magnesium is preferably in the form of magnesium, magnesium L-arginate, magnesium L-arginine ascorbate and bis-ascorbate, magnesium α-lipoate, magnesium α-lipoate ascorbate or bis-ascorbate, magnesium taurate, magnesium taurine ascorbate or bis-ascorbate, magnesium L-acetylcysteine, magnesium L-carnitate, magnesium L-carnitine ascorbate or bis-ascorbate, magnesium ascorbate, or magnesium bis-ascorbate.

Melatonin

Melatonin is an indole produced in the pineal gland and the retina. Its importance in orchestrating diurnal rhythms is well known. Less known is its potent antioxidant action similar to SOD. Some studies have shown that melatonin protects against oxidative stress and the severity of diabetes induced by STZ. Two activities are becoming apparent: 1) the powerful antioxidant action of this indole and, 2) the importance of oxidative stress in the maintenance of hyperglycemia and protein glycation. (See above.) Melatonin reduces hyperglycemia, protein glycation and lipid peroxidation—all diabetic complications in which oxidative stress, either in a high or in a low degree, is present.

TNF-α has an important role in the development of insulin resistance, and type 2 diabetes and its progressive vascular complications. It can be favorably modified by melatonin. Cytokine production, including TNF-α, in human whole blood exhibits diurnal rhythmicity. Peak production of the pro-inflammatory cytokines IFN-gamma, TNF-alpha, IL-1 and IL-12 occurs during the night and early morning at a time when plasma cortisol is lowest. Melatonin levels are highest during these hours and tend to inhibit this cytokine surge. The altered nightly quantity (reduced) or pattern of melatonin secretion in the elderly could fail to reduce the cytokine surge adequately and be detrimental in patients with progressive insulin resistance or type 2 diabetes. This may foster well-known, diabetic microvascular and macrovascular complications.

Melatonin also reduces the visceral fat that is associated with progressive insulin resistance and type 2 diabetes. Thus its supplementation provides an important adjunct to enhance the weight loss potential of metformin.

Visceral fat and plasma insulin levels increase with aging, and are associated with progressive insulin resistance and type 2 diabetes. Since melatonin favorably modulates visceral fat and the nighttime cytokine surge, melatonin supplementation may potentially provide an important adjunct to combined sulfonylurea-metformin therapy, especially in light of the propensity of sulfonylurea to increase weight gain.

The role of melatonin as an immunomodulator is now established; it exerts protective effects in inflammation, extending beyond its antioxidant action. Melatonin reduces the inducible isoform of nitric oxide synthase (iNOS), an important contributor to the pathophysiology of inflammation, including the macrovascular complications of diabetes and pancreatic β-cell destruction. Melatonin reduces iNOS steady-state mRNA levels and iNOS protein. This inhibition of iNOS expression is associated with inhibition of activation of the transcription factor nuclear factor kappa B (NFkappaB), which has been associated with pancreatic β-cell apoptosis in type 1 diabetes.(See above.) Additionally, melatonin decreases the production of nitrite/nitrate (the breakdown products of NO) in macrophages stimulated with bacterial lipopolysaccharide, reducing inflammation. These effects may be important in inhibiting the progression from type 2 diabetes to "type 1.5 diabetes", wherein there is an added immunologically driven β-cell destruction superimposed on type 2 diabetes.

A preponderance of evidence indicates that melatonin production declines after age 45 parallel with a statistically increasing occurrence of type 2 diabetes. It is reasonable to believe that the age-related loss of availability of melatonin and a subsequent reduction in capacity to reduce lipid peroxidation and AGEs, could be detrimental in type 2 diabetes. Supplemental melatonin as an adjunct to the clinical use of combination sulfonylurea-metformin treatment in progressive insulin resistance and type 2 diabetes is physiologically appropriate, and possibly should be made not only at night, but also during the day.

Nicotinate/Nicotinamide

Nicotinic acid (and its derivatives) and metformin are both useful for reducing hypertriglyceridemia, thus having complementary potential in treating the dyslipidemia of progressive insulin resistance and type 2 diabetes.

In addition, nicotinic acid reduces the fibrinogen concentration in plasma and stimulates fibrinolysis.

Nicotinamide has value in preventing β-cells destruction in type 1 diabetes. That there are beneficial effects in type 2 diabetes is not yet established, but prevention of progression from type 2 diabetes to "type 1.5 diabetes" seems likely, thus complementing sulfonylurea. Interleukin-1 beta (IL-1 beta) is known to inhibit glucose-induced insulin release by pancreatic islets. When islets are simultaneously exposed to IL-1 beta and increasing concentrations of nicotinamide, a dose-dependent recovery of glucose-induced insulin secretion can be observed, with the maximum effect at 25 mmol/L nicotinamide Type 1 diabetes is caused by an immune-mediated destruction of the insulin-producing β-cells. β-cells are destroyed by induction of oxygen-derived free radicals and induced nitric oxide. This results in perturbation of the mitochondrial respiratory system and frequent DNA strand breaks. As a result of β-cells destruction, islet cell antibodies can be demonstrated in the circulation. These antibodies can be detected up to eight years prior to overt type 1 diabetes and are also seen in some progressing type 2 diabetics (thus the name "type 1.5 diabetes"). Nicotinamide, a vitamin $B_3$ derivative, interferes with the immune-mediated β-cell destruction by reducing the content of free radicals and NO, thereby reducing their deleterious effects.

Nicotinamide increases the intracellular nicotinamide adenine dinucleotide (NAD) pool, thus increasing the energy supply of the cell as well as activating cNOS and the myriad beneficial vascular effects of constitutive NO/cGMP, which have been discussed above.

Nicotinamide protects β-cell from desensitization to glucose that occurs after prolonged exposure to hyperglycemia.

Unfavorable Theological properties of blood, and abnormal red cell deformability, in diabetes are factors in its frequent microvascular complications. The improvements in blood rheology and in red cell deformability by α-tocopherol nicotinate, can be mainly attributed to reducing lipid peroxidation stress on the membrane of red blood cells. Treatment with α-tocopherol nicotinate may have complementary effects in slowing the microangiopathy of type 2 diabetes.

Pyridoxine

Nonenzymatic protein glycation (Amadori→Maillard reactions) leads to heterogeneous, toxic and antigenic AGEs and to reactive precursors that are implicated in the pathogenesis of diabetes. Pyridoxamine and thiamine pyrophosphate potently inhibit AGE formation, suggesting that these two compounds may have clinical potential in preventing vascular complications in type 2 diabetes and in insulin resistance.

Increased dietary intakes of pyridoxine (and of folate and vitamin $B_{12}$) have been associated with reduced serum homocysteine concentrations in persons at high risk of cardiovascular and cerebrovascular disease, and to those diabetic macrovascular complications not reduced even by intensive sulfonylurea or metformin treatment. iNOS within activated macrophages contributes to the inflammation that characterizes early atherogenesis and may, in part, account for the adverse vascular effects of hyperhomocysteinemia. The incorporation of pyridoxine (and folic acid) lessens the conversion of L-arginine to toxic levels of homocysteine-induced NO (from iNOS within activated macrophages) and in such a fashion, fueling the ubiquitous 'methionine cycle-homocysteine cycle'. This adds an element of safety to the invention by addressing a problem that the nonspecific, "shotgun" supplementation of "multivitamins" usually overlooks.

Selenium

Selenium (Se) has insulin-mimetic actions relating to its involvement with the activity of MAPK and S6 kinases.

Se is also the cofactor for glutathione peroxidase, enabling the scavenging of hydrogen peroxide and avoiding its progression to the hydroxyl radical. It has also been shown to favorably influence the coagulopathy associated with endothelial dysfunction and to improve RBC microviscosity. Reduced Se concentrations in RBCs contribute to impaired hemorheology in diabetic patients.

Se, and more efficiently Se plus Vitamin E, supplementation in diabetes may play a role in controlling oxidative status and unfavorable lipid metabolism in the liver, thereby maintaining favorable fatty acid distribution in the major tissues affected by diabetic complications.

Taurine (2-aminoethanesulfonic acid)

Sulfonylurea-metformin's combined clinical efficacy is reflective of reduced hepatic glucose output and increased insulin secretion; these actions are complemented by peripheral insulin sensitizers like taurine, the small, sulfur containing, amino acid which is the predominant free intracellular amino acid in most mammals.

Cysteine (a taurine precursor) is formed from methionine in a reaction catalyzed by cystathionase, which is very low in man. For this reason taurine is classified as a conditionally essential amino acid.

The first established physiologic function of taurine is bile acid conjugation in the liver resulting in water-soluble bile salts, which are essential for fat absorption from the small intestine. However, while the exact mechanism is not clear, taurine also inhibits lipid peroxidation and decreases blood triglycerides and LDL-cholesterol levels in diabetes.

A deficient dietary level of taurine is associated with a variety of pathologies, including type 2 diabetes. Since 1981 taurine has been added to infant formulas and parental nutrition solutions in countries around the world and was approved by the FDA for this purpose in 1984.

The insulin secretion action of sulfonylurea is optimized by the action of taurine in maintaining intracellular $Ca^{2+}$ homeostasis and in maintaining the integrity of the pancreatic β-cells within which it is present in large amounts.

Taurine extends the effectiveness of sulfonylurea-metformin therapy by increasing peripheral insulin sensitivity, reducing hypercholesterolemia, inhibiting peroxidation of cell membrane components and modulating pericyte and other cell volume instabilities of type 2 diabetes. Its ACE inhibitor-like action adds an important dimension in modulating the characteristic hypertension of progressive insulin resistance and type 2 diabetes. The cardiac failure seen in later stages of these diseases may benefit from the mild cardiac glycoside-like effect of taurine, in addition to blocking the production of angiotensin II. Finally, it protects against glutamate excitotoxicity, inhibiting diabetic neuropathy.

Taurine can prolong the effectiveness of treatment with sulfonylurea-metformin combinations by protecting the pancreatic β-cells from lipid peroxidation, thereby reducing the resulting β-cell dysfunctional apoptosis that can lead to "type 1.5 diabetes".

Taurine stabilizes cellular functions when challenged with external or internal stressors such as perturbations in $Ca^{2+}$, free radicals or osmolality fluctuations.

Intracellular taurine declines with advancing age and in type 2 diabetes. This compounded decrease during both senescence and type 2 diabetes exacerbates age-related declines in antioxidant defense systems, $Ca^{2+}$ regulation and membrane integrity. The actions of sulfonylurea in $K^+$ channel blockade, membrane depolarization and $Ca^{2+}$ influx, depend upon the subsequent recovery of $Ca^{2+}$ homeostasis and membrane repolarization. Taurine contributes to this recovery without which sulfonylurea loses its effect on insulin secretion. The intracellular $Ca^{2+}$ membrane stabilization scenario is complex; taurine, carnitine and $Mg^{2+}$ are all major players. In summary: Taurine moves cytosolic $Ca^{2+}$ into the mitochondria where it is involved in the mitochondrial production of ATP, providing carnitine has moved sufficient long chain fatty acid into the mitochondria to fuel the manufacturing of ATP. ATP then moves out of the mitochondria to supply energy to pump cytosolic $Ca^{2+}$ out of the cell—the ion transfer being catalyzed by $Mg^{2+}$ co-factored ATPase. At this point the membrane has been repolarized and is again receptive to sulfonylurea stimulation. However, taurine, carnitine and $Mg^{2+}$ are all characteristically deficient in type 2 diabetes. This emphasizes the importance of the use of formulations described in this invention as adjuncts to sulfonylurea-metformin therapy.

Taurine is an important intracellular osmolyte, maintaining optimum cell volume and adjusting the water content of intracellular spaces. In some highly specialized tissues such as brain, kidney, muscle, pericytes and photoreceptors, uncontrolled changes in intracellular water can lead to rapid disruption of the cellular architecture and loss of cell function. In hyperglycemia, especially with the polyol pathway activated, osmotic imbalance leads to membrane disorganization and cellular dysfunction or death, all of which are aggravated by taurine deficiency. A number of the complications of diabetes are associated with or attributed to osmotic disruption of the cytoarchitecture. These may be lessened if there is adequate intracellular taurine and are worsened if there is a deficiency of taurine, as there often is in diabetes.

Taurine appears to reduce cellular insulin resistance and may reduce the accumulation of AGEs within the kidney.

Taurine, as an osmoregulator, should ameliorate diabetic neuropathy and nephropathy, clinically reducing total proteinuria and albuminuria. It inhibits activation of protein kinase C(PKC)-signaled increases in the major cytokine, transforming growth factor beta (TGF-β) that occurs in response to high glucose levels. An increase in TGF-β is implicated in the pathogenesis of glomerulosclerosis in diabetes.

Taurine modulates cell membrane stabilization and levels of cellular $Ca^{2+}$. This modulation of $Ca^{2+}$ signaling further complements the similar action of $Mg^{2+}$. Also, similar to $Mg^{2+}$, taurine stabilizes platelet membranes and reduces platelet aggregation.

Taurine is an important intracellular hydroxyl radical scavenger and participates in systems that include the antioxidant enzymes (superoxide dismutase, catalase, and glutathione peroxidase) and the nutrient-derived antioxidant small molecules (vitamin E, AA, carotenes, flavonoids, GSH and uric acid).

Thiamine

Biguanide-induced lactic acidosis is due to an interference with the pyruvate dehydrogenase complex, thereby altering the normal pyruvate oxidative pathway such that an excessive amount of pyruvate is diverted to lactic acid. Thiamine pyrophosphate is a cofactor in the pyruvate dehydrogenase complex and promotes the aerobic metabolism of pyruvate. Treatment with thiamine can be effective in reducing biguanide-induced lactic acidosis.

Thiamine is also very important in the synthesis of insulin, such that its deficiency reduces insulin secretion. Sulfonylurea cannot increase the biosynthesis of insulin in the face of thiamine deficiency. As a result, blood glucose is elevated and insulin is reduced in thiamine deficiency and when this deficiency is corrected, blood glucose levels are lowered.

The glycation of membrane bound proteins associated with the production of AGEs, may be reduced in diabetics given thiamine. This effect is increased further when pyridoxamine is used concurrently with thiamine.

Tocotrienol (Tocopherol Analog) and α-Tocopherol

Approximately 80% of all patients with diabetes die of cardiovascular disease. Treatment with sulfonylurea-metformin has been ineffective in altering this dismal prognosis. Progressive insulin resistance, the fundamental defect of type 2 diabetes leads to hyperinsulinemia, which is associated with hypertension, atherogenic dyslipidemia, left ventricular hypertrophy, impaired fibrinolysis, visceral obesity, and a sedentary lifestyle. Although all these conditions are associated with atherosclerosis and adverse cardiovascular events, the therapeutic effect of sulfonylurea and/or metformin treatment in patients with diabetes focuses solely on normalizing glucose levels and may even increase hyperinsulinemia, increasing the risk of cardiovascular events. Combined sulfonylurea-metformin therapy should include adjuncts such as tocotrienol or tocopherol, and other limited but clearly defined components, included in the formulations of this invention to inhibit diabetic macrovascular disease.

Tocotrienol is a natural farnesylated analogue of tocopherol, which alters the way in which it is anchored to protein, providing additional functional effectiveness to its influence upon lipid metabolism. In addition to actions shared with tocopherol, tocotrienol decreases hepatic cholesterol production and reduces plasma cholesterol levels in animals.

Tocotrienol influences the mevalonate pathway in mammalian cells by post-transcriptional suppression of HMG-CoA reductase, and modulates the intracellular mechanisms that control the degradation of this reductase protein—an activity that mirrors the actions of the putative non-sterol, isoprenoid regulators derived from mevalonate. Thus, tocotrienol has effects on various lipid parameters different from those of α-tocopherol, while having similar effects otherwise.

D,α-tocopherol inhibits the hyperglycemia-induced activation and free fatty acid-induced activation of the diacylglycerol-phosphokinase C (DAG-PKC) pathway. This pathway is one of the most destructive mechanisms involved with vascular endothelial damage and is at the root of many long-term complications of insulin resistance and diabetes, particularly nephropathy and retinopathy.

Hyperglycemia is the major causal factor in the development of diabetic microvascular complications and can mediate the adverse effects of those complications through multiple pathways. One, is the activation of protein kinase C (PKC) by hyperglycemia-induced increases in diacylglycerol (DAG) level, partly due to de novo synthesis. The activation of PKC regulates various vascular functions by modulating enzymatic activities such as cytosolic phospholipase A2 and $Na^+$, $K^+$-ATPase, and gene expressions including extracellular matrix components and contractile proteins. Some of the resulting vascular abnormalities include changes in retinal and renal blood flow, contractility, permeability, proliferation, and basement membrane disturbances. Administration of vitamin E, which decreases DAG level through the activation of DAG kinase, prevents hemodynamic changes in retina and renal glomeruli of diabetic rats. In addition, the inhibition of PKC can normalize the changes in gene expression of cytokines, caldesmon, and hemodynamics.

Tocopherol also has an antiplatelet effect. It significantly inhibits fibrinogen-induced platelet aggregation, perhaps through interference with fibrinogen binding at its receptor.

Supplementation with $\alpha$-tocopherol reduces lipids and lipid peroxides in diabetics and may be beneficial reducing LDL oxidizability. It also can have an effect on reducing AGEs.

Tocopherol is the main defense against the peroxidation cascade within the lipid layer of cell membranes. The latter is the principal cause of the loss of cell membrane integrity in many pathologic states of vascular and neuronal cells, including diabetes. Tocopherol preserves SOD, involved in free radical hydrogen peroxide defense.

In animals supplemental $\alpha$-tocopherol inhibits calcium-induced cytosolic enzyme efflux.

Increased oxidative stress, hypofibrinolysis and insulin resistance are present in obese type 2 diabetes patients. High doses of vitamin E (600 mg/day) used alone, may further worsen insulin efficiency and increase fibrinolysis in these patients. This finding supports the complementary, multicomponent design of this invention, as opposed to the widespread practice of using high doses of single components without regard either to their useful or to their deleterious interaction with other biofactors. The other components of this invention, which complement tocopherol in reducing oxidative stress are lipoic acid, N-acetyl-cysteine, ascorbate, taurine, Se, $Mg^{2+}$, and taurine (See above.).

When tocotrienol or D,$\alpha$-tocopherol are administered they increase the effectiveness, efficiency, and safety of combinations of sulfonylurea-metformin in the prevention and treatment of insulin resistance and diabetes mellitus and addresses their shortcomings in diabetic macrovascular disease.

Ubiquinone (Coenzyme Q10)

Ubiquinone acts as an electron carrier within the mitochondrial respiratory chain that leads to ATP (energy) generation. It also is an effective scavenger of free radicals.

Since the oxidative process within the mitochondria is only 95% efficient, mitochondrial metabolism is a significant contributor of unmodified reactive oxygen species within the mitochondria. Ubiquinone not only is of pivotal importance in mitochondrial energy production, but it cleans up the free radicals generated by the process. In this fashion it prevents mitochondrial GSH depletion and reduces oxidant-induced losses of mitochondrial functions. This lowers oxidative stresses within the mitochondria, which otherwise could promote extra-mitochondrial activation of the NFkappaB apoptotic cascade.

Outside the mitochondria, ubiquinone prevents lipid peroxidation of the plasma and liposomal membranes, sparing GSH and tocopherol in these domains. Unlike tocopherol it is not recycled by ascorbate.

Ubiquinone is significantly lower in diabetics. Diabetic patients controlled by diet may have a deficiency of ubiquinone, and additionally, ubiquinone may be inhibited by sulfonylureas and/or metformin. A deficiency of ubiquinone in the pancreas could impair bioenergetics—the generation of ATP—and the biosynthesis of insulin, perhaps accounting in part to the loss of effect insulin secretory effect that occurs with long-term sulfonylurea use.

In one randomized, double blind trial 30 patients (with essential hypertension and coronary artery disease receiving antihypertensive medication) the effects of oral coenzyme Q10 (60 mg twice daily for 8 weeks) were evaluated. The systolic and diastolic blood pressure, fasting and 2-h plasma insulin, glucose, triglycerides, lipid peroxides, malondialdehyde and diene conjugates were all reduced, and HDL-cholesterol was increased. These findings suggest that oral treatment with coenzyme Q10 can be effective in decreasing blood pressure and improving insulin response.

Vanadium

Most patients with type 2 diabetes mellitus require pharmacotherapy, initially as monotherapy, subsequently in combination. Exogenous insulin is ultimately required in a substantial proportion, reflecting the progressive natural history of the disease. As noted earlier, both the sulphonylureas and the biguanides have been employed for over 4 decades as oral antidiabetic agents, but they have a limited capacity to provide long-term glycemic control.

Vanadium increases both hepatic and peripheral insulin sensitivity, thus expanding the activity of combinations of sulfonylurea-metformin. It also activates glycogenesis and thereby decreases hyperglycemia by complementing metformin's inhibition of glycogenolysis. Furthermore, it has been reported to activate ATP-sensitive potassium (K(ATP)) channels in the absence of nucleotides. K(ATP) channels comprise Kir6.2 and sulfonylurea receptor subunits (SUR1 in pancreatic $\beta$-cells, SUR2A in cardiac and skeletal muscle, and SUR2B in smooth muscle).

Vanadium has therapeutic potential in both type 1 and type 2 diabetes in doses ranging from 0.083 mmol/d to 0.42 mmol/d. Although vanadium has significant biological potential, it has a poor (narrow) therapeutic index. Organic forms of vanadium, as opposed to the inorganic sulfate salt, may be safer, more absorbable, and may be able to deliver a therapeutic effect up to 50% greater than the inorganic forms. Vanadium has been administered to pregnant women diagnosed with pregnancy-induced diabetes without adverse effects upon either the mother or fetus.

Vanadium is present in a variety of foods that we commonly eat. The daily dietary intake in humans varies from 10 micrograms to 2 mg of elemental vanadium, depending on the sources available in various regions. The 100 mg/day often used in treating type 2 diabetes is clearly greater than physiological, probably accounting for what is described as a narrow therapeutic index. Utilizing vanadium as one element in multicomponent formulations, as defined in this invention, will permit the dosage to be minimized and safety increased.

Vanadate and pervanadate (pV) are protein tyrosine phosphatase (PTP) inhibitors that mimic insulin to stimulate glucose transport. Vanadate and pV are able to stimulate glucose transport and GLUT4 translocation by mechanisms independent of PI 3-kinase and PKC. Similar to insulin, stimulation of glucose transport by vanadate requires the presence of an intact actin network.

Vanadate ($V^{5+}$), an oxidized form of vanadium, or vanadyl ($V^{4+}$) promote both hepatic and peripheral insulin action by three mechanisms: 1) direct insulin-mimesis; 2) enhancement of insulin sensitivity and 3) prolongation of the insulin biological response. The insulin-mimetic action of these forms of vanadium persists after withdrawal of treatment. Vanadium treatment of non-diabetic animals lowers plasma insulin levels by reducing insulin demand, and these animals remain normoglycemic. Chronic treatment with vanadium has also been shown to result in sustained antidiabetic effects in STZ-diabetic animals long after treatment has ceased. Thus, 13 weeks after withdrawal from vanadium administration, treated animals have normalized glucose levels and normal weight gain, and improved basal insulin levels. In addition, near-normal glucose tolerance is found despite an insignificant insulin response. Since vanadium accumulates in several tissue sites when pharmacological doses are administered (e.g., bone, kidney), it is possible that stored vanadium may be important in maintaining near-normal glucose tolerance, at least in the short-term following withdrawal from treatment.

In humans, after 3 weeks of vanadyl sulfate (100 mg/day), both hepatic and peripheral insulin sensitivity appear to improve. in insulin-resistant type 2 diabetes patients. These effects are sustained for up to 2 weeks after discontinuation of vanadyl sulfate.

There are some distinct signal-transduction pathways for vanadate and for insulin in the activation of glycogen synthase and glycogenesis. Although both vanadate and insulin increase glycogenesis and glycogen synthase, there are differences as well as similarities. In several aspects, vanadate and insulin resemble each other: 1) in their activation of glycogen synthase; 2) each requires nonarrested protein phosphatase 1 activity; 3) each is equally suppressed by conditions that elevate cAMP-levels' and 4) each depends on the activation of phosphatidylinositol-3 kinase. The differences between them are equally specific: 1) vanadate promotes glycogenesis through the activation of a cytosolic protein tyrosine kinase, in an insulin-receptor-independent manner; 2) vanadate elevates glucose-6-phosphate (G-6-P) to a higher level than insulin; 3) vanadate-activated glycogenesis is accompanied by an increase in the cellular content of immunoreactive glycogen synthase, an effect less noticeable with insulin; 4) adipose glucose-6-phosphatase is inhibited by vanadate but not by insulin. Thus, insulin and vanadate both activate glycogenesis through a phosphatidylinositol-3 kinase and dephosphorylation-dependent mechanism. Vanadate, however, uses a receptor-independent pathway and is superior to insulin in elevating the level of G-6-P, a key metabolite for activating glycogen synthase. This is attributed to the combined effect of vanadate in enhancing glucose entry and in inhibiting dephosphorylation of endogenously formed G-6-P. The latter effect is not exerted by insulin.

Vanadium has several mechanisms of action in progressive insulin resistance and type 2 diabetes:
1. Increased insulin sensitivity
2. Activates glycogenesis
3. Enzyme effects:
   PTPase inhibition
   PTK activation
   PI3K activation
   Glycogen synthase activation
   Improves activation of S6 kinase by insulin
4. Preserves pancreatic β-cells
5. Mimics insulin effect on calmodulin in liver and adipose tissue
6. Accelerates the metabolic reaction from sorbitol pathway to glycolysis
7. Decreases diabetic hyperphagia
8. Down-regulates small intestine glucose carriers
9. Inhibits NO production by macrophages Tolerance does not appear to develop with long term oral administration of vanadium, but the safety of chronic vanadium treatment beyond five months is not yet established. This may have an impact on the therapeutic use of vanadium. To reduce this possibility of chronic use toxicity, the invention describes a pulsing of vanadium administration and/or once a day bedtime use to take advantage of the prolonged vanadium insulin-mimetic effect following withdrawal of treatment.

Zinc $Zn^{2+}$ plays a clear role in the synthesis, storage and secretion of insulin as well as preserving the conformational integrity of insulin in the hexameric form The relationship between diabetes, insulin and $Zn^{2+}$ is complex. Functioning as an insulin cofactor, $Zn^{2+}$ prevents hyperglycemia by increasing insulin activity at its receptor site. Diabetics tend to have low plasma $Zn^{2+}$ concentrations and decreased total body $Zn^{2+}$. Hyperglycemia, rather than any primary lesion related to diabetes, is responsible for increased urinary loss and a decrease in total body $Zn^{2+}$, which in turn is in part responsible for hyperglycemia. Dietary $Zn^{2+}$ is potentially inadequate in any given geographic region; a low groundwater content of $Zn^{2+}$ may contribute to population deficiencies.

In comparison to healthy control subjects, a significantly lower Cu, Zn-superoxide dismutase activity is found in both lymphocytes and polymorphonuclear cells of type 1 diabetes and type 2 diabetes patients. A $Zn^{2+}$ deficiency can, therefore, reduce immunoefficiency or aggravate an existing immune deficiency, and contribute to the slow wound healing seen in diabetics.

Adequate $Zn^{2+}$ is necessary for angiotensin converting enzyme inhibitors (ACE). All ACE inhibitors bind to $Zn^{2+}$ ions. ACE inhibitors have clinically beneficial effects; not only for patients with hypertension or congestive heart failure, but also for the prevention of the progression of renal dysfunction induced by diabetes mellitus.

The zinc is preferably in the form of zinc halide, zinc sulfate, zinc L-carnitate, zinc L-carnitate ascorbate or bis-ascorbate, zinc taurate, zinc taurine ascorbate or bis-ascorbate, zinc L-arginate, zinc L-arginine ascorbate or bis-ascorbate, zinc L-carnitate, zinc L-carnitine ascorbate or bis-ascorbate, zinc phosphate, zinc acetate, zinc ascorbate, or zinc bis-ascorbate.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. Treatment of the disease or condition may require periodic administration of unit dosage forms, for example: one or two unit dosage forms two or more times a day, one or two with each meal, one or two every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition, which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

"Vasoconstriction" is the reduction of the cross section of a blood vessel lumen, inhibiting the free flow of blood through the vessel. Vasoconstriction can arise from vasospasm, deposits on or in the lumen wall or from the thickening of the wall material due to excessive growth or proliferation of one or more of the wall layers.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Compositions, Formulations and Dosages

The amounts of the twenty-one primary components of the pharmaceutical preparation of this invention can vary, although in preferred preparations the components are present in amounts lying within certain ranges as follows:

TABLE 1

| | Dosages in Milligrams | |
|---|---|---|
| | Preferred | Most Preferred |
| L-Arginine | 75 to 6250 | 250 to 2500 |
| Ascorbate | 75 to 3125 | 250 to 1250 |
| Tetrahydrobiopterin | 24 to 3000 | 80 to 1200 |
| L-Carnitine | 90 to 2500 | 300 to 1000 |
| Choline | 15 to 250 | 50 to 100 |
| Chromium | 0.01 to 0.63 | 0.03 to 0.25 |
| Folate | 0.03 to 2.0 | 0.10 to 0.80 |
| Lipoate | 30 to 1500 | 100 to 600 |
| Magnesium | 30 to 1000 | 100 to 400 |
| Melatonin | 0.15 to 7.5 | 0.5 to 3 |
| N-acetyl-L-cysteine | 78 to 3900 | 200 to 1200 |
| Nicotinate | 3 to 375 | 10 to 150 |
| Pyridoxine | 0.3 to 15 | 1.0 to 6.0 |
| Selenium | 0.02 to 0.75 | 0.05 to 0.3 |
| Taurine | 75 to 3125 | 250 to 1250 |
| Thiamine | 0.45 to 37.5 | 1.5 to 15 |
| Tocopherol, D, α | 15 to 1600 | 50 to 800 |
| Tocotrienol | 15 to 2000 | 50 to 800 |
| Ubiquinone | 4.5 to 225 | 15 to 90 |
| Vanadium | 7.5 to 375 | 25 to 150 |
| Vitamin B12 | 0.001 to .010 | 0.002 to .004 |
| Zinc | 1.5 to 80 | 5 to 32 |

A slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bio-erodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the dosage form is a substantially-homogeneous single layer tablet that releases all of its components into the stomach upon ingestion. An example of such a tablet is shown in Examples I, II and III.

EXAMPLE I

Adjunct to Metformin Treatment

A single layer tablet, substantially homogenous in composition, which will disintegrate upon ingestion to provide simultaneous accessibility to all components, is prepared with the following composition:

| SINGLE LAYER UNIT DOSEAGE FORM FOR: METFORMIN ADJUNCT | | tabs/day 4.00 | |
|---|---|---|---|
| TABLET WEIGHT 684 | | mg/day 2734 | |
| FOR IMMEDIATE RELEASE IN THE STOMACH | | 100% % of formula | milligram |
| Mg(C6H7O6)2 | Magnesium L-Ascorbate | 9.78% | 267.35 |
| (C2H7NO3S)2Mg | Magnesium Taurate | 20.08% | 548.95 |
| C5H9NO3S | N-Acetyl-L-Cysteine | 18.29% | 500.00 |
| C9H15N5O3 | Tetrahydrobiopterin | 9.14% | 250.00 |
| C62H51O4 | Ubiquinone | 5.49% | 150.00 |
| C29H50O2 | D,a-Tocopherol | 11.41% | 312.00 |
| C19H19N7O6 excipients | Folic acid | 0.004% | 0.10 |
| Mg(C18H35O2)2 | Magnesium Stearate | 0.76% | 20.85 |
| . . . | Starch | 25.05% | 685.00 |

EXAMPLE II

Adjunct to Sulfonylurea Treatment

A single layer tablet, substantially homogenous in composition, which will disintegrate upon ingestion to provide simultaneous accessibility to all components, is prepared with the following composition:

| SINGLE LAYER UNIT DOSEAGE FORM FOR: SULFONYLUREA ADJUNCT | | tabs/day 4.00 | |
|---|---|---|---|
| TABLET WEIGHT 855 | | mg/day 3420 | |
| FOR IMMEDIATE RELEASE IN THE STOMACH | | 100% % of formula | milligrams |
| (C7H15NO3)2Mg | Magnesium L-Carnitine | 23.59% | 806.54 |
| Mg(C6H7O6)2 | Magnesium L-Ascorbate | 7.82% | 267.35 |
| Mg(C6H13N4O2)2 | Magnesium L-Arginate | 23.47% | 802.62 |
| Zn(C8H12O2S2)2 | Zinc Lipoate | 10.18% | 348.01 |
| C29H50O2 excipients | D,a-Tocopherol | 9.12% | 312.00 |
| Mg(C18H35O2)2 | Magnesium Stearate | 0.76% | 26.07 |
| . . . | Starch | 25.06% | 857.00 |

EXAMPLE III

Adjunct to Combined Metformin-Sulfonylurea Treatment

A single layer tablet, substantially homogenous in composition, which will disintegrate upon ingestion to provide simultaneous accessibility to all components, is prepared with the following composition:

| SINGLE LAYER UNIT DOSEAGE FORM FOR: | | tabs/day 4.00 | |
|---|---|---|---|
| METFORMIN-SULFONYLUREA ADJUNCT | | | |
| TABLET WEIGHT 783 | | mg/day 3132 | |
| FOR IMMEDIATE RELEASE IN THE STOMACH | | 100% % of formula | milligram |
| (C7H15NO3)2Mg | Magnesium L-Carnitine | 17.17% | 537.69 |
| Mg(C6H7O6)2 | Magnesium L-Ascorbate | 8.54% | 267.35 |
| (C2H7NO3S)2Mg | Magnesium Taurate | 17.53% | 548.95 |
| Zn(C8H12O2S2)2 | Zinc Lipoate | 7.41% | 232.00 |
| C9H15N5O3 | Tetrahydrobiopterin | 7.98% | 250.00 |
| C62H51O4 | Ubiquinone | 4.79% | 150.00 |
| C29H50O2 | D,a-Tocopherol | 9.96% | 312.00 |
| C19H19N7O6 | Folic acid | 0.006% | 0.20 |
| excipients | | | |
| Mg(C18H35O2)$^2$ | Magnesium Stearate | 0.77% | 23.98 |
| . . . | Starch | 25.86% | 810.00 |

In certain other embodiments of the invention, the dosage form is protected by an acid-resistant coating for release only in the intestine, and optionally in a sustained-release manner over a period of time.

another embodiment of the invention, the dosage form is a combination tablet in which the components are divided into two portions: one that is fully released into the stomach upon ingestion, and the other protected by an acid-resistant coating for release only in the intestine, and optionally in a sustained-release manner over a period of time.

The controlled release layer comprises about 50% by weight of the tablet and has an acid-resistant coating separating it from the immediate release layer. The immediate release layer comprises about 50% by weight of the tablet and has a coating that dissolves in an aqueous environment.

Ingredients for each layer are fed into appropriate hoppers of a two-layer, rotary tablet press, and compressed into two-layer tablets. The magnesium stearate present in both layers provides lubrication of the tablet press and serves as a minimal source of magnesium in the formulation. Se and folic acid are each added as a spray.

Upon oral ingestion of the tablet, agents of the immediate release layer dissolve rapidly in the stomach and are available for immediate absorption in the gastrointestinal tract. The polymer matrix of the controlled release layer, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. Since the agents have been selected with a view toward their water solubilities, the rate of diffusion of each agent is reasonably constant for the useful life of the matrix (approximately four hours), by which time the incorporated agents are finally depleted and the matrix disintegrates.

The dosage forms of this invention can be formulated for administration at rates of two or more unit dosage forms per dose. Unit dosage forms to be taken two units, three to four times per day are preferred.

Methods of Administration and Types of Utility

The compositions and dosage forms of the invention are useful for increasing the effectiveness, efficiency and safety of combined sulfonylurea-metformin pharmaceuticals and combined sulfonylurea-like/metformin pharmaceutical agents, in the prevention and treatment of insulin resistance and diabetes mellitus, alone or in combination, as a nutrient for humans. The carefully chosen active ingredients of the invention act in a well-defined and complementary biochemical partnership with sulfonylurea-metformin to avoid the development of, or ameliorate, progressive insulin resistance, to retard its progression to diabetes mellitus and to ensure an improvement in glucose tolerance, hypertension and obesity associated with type 2 diabetes, or a reduction in the morbidity rate; and that diabetic microvascular complications (nephropathy, retinopathy, neuropathy, etc.) as well as diabetic macrovascular complications (atherosclerosis, heart attack, stroke, peripheral vascular disease, etc.) are lessened.

The invention will achieve these therapeutic objectives by:

Enhancing combined sulfonylurea-metformin effectiveness by:
1. prolonging the duration of sulfonylurea-metformin's clinical usefulness;
2. reducing sulfonylurea-metformin dosage required by increasing its efficiency;
3. reducing diabetic microvascular complications;
4. increasing insulin secretion;
5. decreasing insulin resistance at its receptor;
6. reducing hyperglycemia;
7. decreasing lipid peroxidation secondary to free radical formation of hyperglycemia;
8. preventing formation of advanced glycation end products;
9. modulating calcium signaling and β-cell membrane polarization and repolarization;
10. preventing endothelial cell dysfunction;
11. improving lipid profiles;
12. inhibiting platelet aggregation;
13. reducing norepinephrine release from cardiac sympathetic nerves.

Expanding combined sulfonylurea-metformin areas of effect by:
1. reducing diabetic macrovascular complications;
2. reducing premature apoptosis of pancreatic b-cell;
3. reducing dysfunctional vasoconstriction;
4. increasing hepatic and peripheral insulin sensitivity;
5. decreasing insulin post-receptor disturbances;
6. increasing the number of insulin receptors and the duration of action of insulin;
7. maintaining pancreatic islet B-cell sensitivity to glucose;
8. optimizing the b-cell cytoplasmic free Ca2+level;
9. inhibiting the polyol pathway and consequent sorbitol effects;
10. reducing LDL oxidation;
11. reducing the free radical effect at the caveolae and mitochondrial permeability transition pore complex;
12. decreasing vascular adhesion factors and maintaining membrane proteoglycans;
13. reducing PAI-1 inhibitor and improving fibrinolysis.

Reducing combined sulfonylurea-metformin adverse effects by:
1. reducing sulfonylurea-metformin gastrointestinal intolerance;

2. reducing sulfonylurea induced weight gain and inadequate fatty acid oxidation;
3. reducing sulfonylurea risk of hypoglycemia;
4. reducing the sulfonylurea hypofibrinolytic effect;
5. reducing coronary vasoconstriction secondary to sulfonylurea reduced ATP-sensitive, K+ channel blockade;
6. avoiding biguanide induced hyperhomocysteinemia;
7. avoiding biguanide lactic acidosis.

Formulations designed for different aspects of progressive insulin resistance and type 2 diabetes processes are illustrated in the specifications and defined in the section on claims. Formulations will be used in appropriate sequencing, or pulsing to maximize effectiveness while avoiding toxicity. This is defined in the claims section.

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

REFERENCE LIST (1) Aarsand A K, Carlsen S M. Folate administration reduces circulating homocysteine levels in NIDDM patients on long-term metformin treatment. J Intern Med 1998; 244(2):169–174.
(2) Barbagallo M, Dominguez L J, Tagliamonte M R, Resnick L M, Paolisso G. Effects of vitamin E and glutathione on glucose metabolism: role of magnesium. Hypertension 1999; 34(4 Pt 2):1002–6.
(3) Bierhaus A, Chevion S, Chevion M, Hofmann M, Quehenberger P, Illmer T et al. Advanced glycation end product-induced activation of NF-kappaB is suppressed by alpha-lipoic acid in cultured endothelial cells. Diabetes 1997; 46(9):1481–90.
(4) DeFronzo R A. Pharmacologic therapy for type 2 diabetes mellitus. Ann Intern Med 1999; 131(4):281–303.
(5) Estrada D E, Ewart H S, Tsakiridis T, Volchuk A, Ramlal T, Tritschler H et al. Stimulation of glucose uptake by the natural coenzyme alpha-lipoic acid/thioctic acid: participation of elements of the insulin signaling pathway. Diabetes 1996; 45(12):1798–804.
(6) Heitzer T, Krohn K, Albers S, Meinertz T. Tetrahydrobiopterin improves endothelium-dependent vasodilation by increasing nitric oxide activity in patients with Type II diabetes mellitus. Diabetologia 2000; 43(11): 1435–1438.
(7) Huang A, Vita J A, Venema R C, Keaney J F, Jr. Ascorbic acid enhances endothelial nitric-oxide synthase activity by increasing intracellular tetrahydrobiopterin. J Biol Chem 2000; 275(23):17399–17406.
(8) Johnston C S, Solomon R E, Corte C. Vitamin C depletion is associated with alterations in blood histamine and plasma free carnitine in adults. J Am Coll Nutr 1996; 15(6):586–591.
(9) Ma J, Folsom A R, Melnick S L, Eckfeldt J H, Sharrett A R, Nabulsi A A et al. Associations of serum and dietary magnesium with cardiovascular disease, hypertension, diabetes, insulin, and carotid arterial wall thickness: the ARIC study. Atherosclerosis Risk in Communities Study. J Clin Epidemiol 1995; 48(7): 927–40.
(10) Matsuda M, Mandarino L, DeFronzo R A. Synergistic interaction of magnesium and vanadate on glucose metabolism in diabetic rats. Metabolism 1999; 48(6): 725–31.
(11) Paolisso G, Tagliamonte M R, Barbieri M, Zito G A, Gambardella A, Varricchio G et al. Chronic vitamin E administration improves brachial reactivity and increases intracellular magnesium concentration in type II diabetic patients. J Clin Endocrinol Metab 2000; 85(1):109–115.
(12) Paulson D J, Shug A L, Zhao J. Protection of the ischemic diabetic heart by L-propionylcarnitine therapy. Mol Cell Biochem 1992; 116(1–2):131–137.
(13) Reaven G M. Pathophysiology of insulin resistance in human disease. Physiol Rev 1995; 75(3):473–86.

What is claimed is:

1. A unit dosage form as an adjunct to biguanide or sulfonylurea therapy for supporting mitochondrial metabolism as a method for the management and clinical amelioration of insulin resistance and type 2 diabetes and conditions giving rise thereto, said unit dosage form comprising as active ingredients:
   (a) L-carnitine,
   (b) ascorbic acid,
   (c) choline,
   (d) taurine,
   (e) folic acid, and
   (f) magnesium.

2. A unit dosage form in accordance with claim 1 in which said active ingredients are formulated as a substantially homogeneous tablet or capsule that releases all of said active ingredients into the stomach upon ingestion for contact with gastric fluid.

3. A unit dosage form in accordance with claim 2 in which:
   (a) said L-carnitine is in an amount ranging from about 90 mg to about 2500 mg, and
   (b) said ascorbic acid is in an amount ranging from about 75 mg to about 3000 mg,
   (c) said choline is in an amount ranging from about 15 mg to about 250 mg,
   (d) said taurine is in an amount ranging from about 75 mg to about 3000 mg,
   (e) said magnesium is in an amount ranging from about 30 mg to about 1000 mg, and
   (f) said folic acid is in an amount ranging from about 0.03 mg to about 2 mg.

4. A unit dosage form as an adjunct to biguanide or sulfonylurea therapy specifically for nocturnal use as a method for the management and clinical amelioration of insulin resistance and type 2 diabetes and conditions giving rise thereto, said unit dosage form comprising as active ingredients:
   (a) melatonin,
   (b) L-carnitine,
   (c) ubiquinone,
   (d) folic acid,
   (e) magnesium, and
   (f) L-arginine.

5. A unit dosage form in accordance with claim 4 in which said active ingredients are formulated as a substantially homogeneous tablet or capsule that releases all of said active ingredients into the stomach upon ingestion for contact with gastric fluid.

6. A unit dosage form in accordance with claim 5 in which:

(a) said melatonin is in an amount ranging from about 0.15 mg to about 7.5 mg, (b) said L-carnitine is in an amount ranging from about 90 mg to about 2500 mg, (c) said ubiquinone is in an amount ranging from about 4.5 mg to about 225 mg, (d) said folic acid is in an amount ranging from about 0.03 mg to about 2 mg, (e) said magnesium is in an amount ranging from about 30 mg to about 1000 mg, and (f) said L-arginine is in an amount ranging from about 75 mg to about 3100 mg.

7. A unit dosage form for use as an adjunct to biguanide or sulfonylurea therapy alternative to insulin for use as a method for the management and clinical amelioration of insulin resistance and type 2 diabetes and conditions giving rise thereto, said unit dosage form comprising as active ingredients:

(a) vanadium, (b) L-arginine, (c) chromium, and (d) zinc.

8. A unit dosage form in accordance with claim 7 in which said active ingredients are formulated as a substantially homogeneous tablet or capsule that releases all of said active ingredients into the stomach upon ingestion for contact with gastric fluid.

9. A unit dosage form in accordance with claim 8 in which:

(a) said vanadium is in an amount ranging from about 7.5 mg to about 375 mg, (b) said L-arginine is in an amount ranging from about 75 mg to about 3100 mg, (c) said chromium is in an amount ranging from about 0.01 mg to about 0.63 mg, and (d) said zinc is in an amount ranging from about 1.5 mg to about 100 mg.

10. A unit dosage form in accordance with claim 1 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| L, carnitine | 40–60% | balance |
| ascorbic acid | 40–60% | balance |
| choline | 100% |  |
| folic acid | 100% |  |
| taurine | 40–60% | balance |
| magnesium | 40–60% | balance |

11. A unit dosage form in accordance with claim 4 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| melatonin | 40–60% | balance |
| L-carnitine | 40–60% | balance |
| zinc | 40%–60% | balance |
| folic acid | 100% |  |
| magnesium | 40–60% | balance |
| ubiquinone | 100% |  |

12. A unit dosage form in accordance with claim 7 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| vanadium | 40–60% | balance |
| L-arginine | 40–60% | balance |
| chromium | 40%–60% | balance |
| zinc | 40%–60% | balance |

13. A unit dosage form in accordance with claim 4 or 7 in which said L-arginine is in the form of a member selected from the group consisting of L arginine ascorbate, bis-L arginine ascorbate, L arginine salt of a metal ion selected from the group consisting of $Mg^{2+}$ and $Zn^{2+}$, bis-L arginine salt of a metal ion selected from the group consisting of $Mg^{2+}$ and $Zn^{2+}$, and a complex of L arginine or bis-L arginine, a metal ion selected from the group consisting of $Mg^{2+}$ and $Zn^{2+}$, and an anion selected from the group consisting of hydroxide, halide, acetate, and ascorbate.

14. A unit dosage form in accordance with claim 1 or 4 in which said L-carnitine is in the form of a member selected from the group consisting of L carnitine ascorbate, bis-L carnitine ascorbate, L carnitine salt of a metal ion selected from the group consisting of $Mg^{2+}$ and $Zn^{2+}$, bis-L carnitine salt of a metal ion selected from the group consisting of $Mg^{2+}$ and $Zn^{2+}$, and a complex of L carnitine or bis-L carnitine, a metal ion selected from the group consisting of $Mg^{2+}$ and $Zn^{2+}$, and an anion selected from the group consisting of hydroxide, halide, acetate, and ascorbate.

15. A unit dosage form in accordance with claim 1 in which said L-taurine is in the form of a member selected from the group consisting of L taurine ascorbate, bis-L taurine ascorbate, L taurine salt of a metal ion selected from the group consisting of $Mg^{2+}$ and $Zn^{2+}$, bis-L taurine salt of a metal ion selected from the group consisting of $Mg^{2+}$ and $Zn^{2+}$, and a complex of L taurine or bis-L taurine, a metal ion selected from the group consisting of $Mg^{2+}$ and $Zn^{2+}$, and an anion selected from the group consisting of hydroxide, halide, acetate, and ascorbate.

16. A unit dosage form in accordance with claim 1 or 4 in which said magnesium is in the form of a member selected from the group consisting of magnesium, magnesium L-arginate, magnesium L-arginine ascorbate and bis-ascorbate, magnesium α-lipoate, magnesium α-lipoate ascorbate and bis-ascorbate, magnesium taurate, magnesium taurine ascorbate and bis-ascorbate, magnesium L-acetylcysteine, magnesium L-carnitate, magnesium L-carnitine ascorbate and bis-ascorbate, magnesium ascorbate and magnesium bis-ascorbate.

17. A unit dosage form in accordance with claim 7 in which said zinc is in the form of a member selected from the group consisting of zinc halide, zinc sulfate, zinc L-carnitate, zinc L-carnitate ascorbate and bis-ascorbate, zinc taurate, zinc taurine ascorbate and bis-ascorbate, zinc L-arginate, zinc L-arginine ascorbate and bis-ascorbate, zinc L-carnitate, zinc L-carnitine ascorbate and bis-ascorbate, zinc phosphate, zinc acetate, zinc ascorbate, and zinc bis-ascorbate.

18. A unit dosage form in accordance with claim 7 in which said vanadium is in the form of a member selected from the group consisting of vanadate, peroxovanadate, vanadyl sulfate salts, and bis(maltolato)oxovanadium(IV).

19. A unit dosage form in accordance with claim 7 in which said chromium is in the form of a member selected from the group consisting of chromium dinicotinate, and chromium tripicolinate.

20. A method for treating a patient who is undergoing biguanide therapy for the management, and clinical amelioration of insulin resistance and type 2 diabetes and conditions giving rise thereto, to reduce undesirable physiological side effects, and enhance the therapeutic effectiveness, of said biguanide therapy, said method comprising administering to said patient a unit dosage form comprising as active ingredients:
(a) L-carnitine,
(b) ascorbic acid,
(c) choline,
(d) taurine,
(e) folic acid, and
(f) magnesium.

21. A method in accordance with claim 20 in which said active ingredients are formulated as a substantially homogeneous tablet or capsule that releases all of said active ingredients into the stomach upon ingestion for contact with gastric fluid.

22. A method in accordance with claim 21 in which:
(a) said L-carnitine is in an amount ranging from about 90 mg to about 2500 mg, and
(b) said ascorbic acid is in an amount ranging from about 75 mg to about 3000 mg,
(c) said choline is in an amount ranging from about 15 mg to about 250 mg,
(d) said taurine is in an amount ranging from about 75 mg to about 3000 mg,
(e) said magnesium is in an amount ranging from about 30 mg to about 1000 mg, and
(f) said folic acid is in an amount ranging from about 0.03 mg to about 2 mg.

23. A method for treating a patient who is undergoing nocturnal biguanide therapy for the preservation of plasma and mitochondrial membrane integrity for the management, and clinical amelioration of insulin resistance and type 2 diabetes and conditions giving rise thereto, to reduce undesirable physiological side effects, and enhance the therapeutic effectiveness, of said biguanide therapy, said method comprising administering to said patient a unit dosage form comprising as active ingredients:
(a) melatonin,
(b) L-Carnitine,
(c) ubiquinone,
(d) folic acid,
(e) magnesium, and
(f) L-arginine.

24. A method in accordance with claim 23 in which said active ingredients are formulated as a substantially homogeneous tablet or capsule that releases all of said active ingredients into the stomach upon ingestion for contact with gastric fluid.

25. A method in accordance with claim 24 in which:
(a) said melatonin is in an amount ranging from about 0.15 mg to about 7.5 mg,
(b) said L-carnitine is in an amount ranging from about 90 mg to about 2500 mg,
(c) said ubiquinone is in an amount ranging from about 4.5 mg to about 225 mg,
(d) said folic acid is in an amount ranging from about 0.03 mg to about 2 mg,
(e) said magnesium is in an amount ranging from about 30 mg to about 1000 mg, and
(f) said L-arginine is in an amount ranging from about 75 mg to about 3100 mg.

26. A method for treating a patient who is undergoing biguanide therapy as an alternative to insulin for the management, and clinical amelioration of insulin resistance and type 2 diabetes and conditions giving rise thereto, to reduce undesirable physiological side effects, and enhance the therapeutic effectiveness, of said biguanide therapy, said method comprising administering to said patient a unit dosage form comprising as active ingredients:
(a) vanadium,
(b) L-arginine,
(c) chromium, and
(d) zinc.

27. A method in accordance with claim 26 in which said active ingredients are formulated as a substantially homogeneous tablet or capsule that releases all of said active ingredients into the stomach upon ingestion for contact with gastric fluid.

28. A method in accordance with claim 27 in which:
(a) said vanadium is in an amount ranging from about 7.5 mg to about 375 mg,
(b) said L-arginine is in an amount ranging from about 75 mg to about 3100 mg,
(c) said chromium is in an amount ranging from about 0.01 mg to about 0.63 mg, and
(d) said zinc is in an amount ranging from about 1.5 mg to about 100 mg.

29. A method in accordance with claim 20 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| L, carnitine | 40–60% | balance |
| ascorbic acid | 40–60% | balance |
| choline | 100% |  |
| folic acid | 100% |  |
| taurine | 40–60% | balance |
| magnesium | 40–60% | balance |

30. A method in accordance with claim 23 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| melatonin | 40–60% | balance |
| L-carnitine | 40–60% | balance |
| zinc | 40%–60% | balance |
| folic acid | 100% |  |
| magnesium | 40–60% | balance |
| ubiquinone | 100% |  |

31. A method in accordance with claim 26 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| vanadium | 40–60% | balance |
| L-arginine | 40–60% | balance |
| chromium | 40%–60% | balance |
| zinc | 40%–60% | balance |

32. A method in accordance with claims 23, or 26 in which said L-arginine is in the form of a member selected from the group consisting of L arginine ascorbate, bis-L arginine ascorbate, L arginine salt of a metal ion selected from the group consisting of $Mg^{2+}$ and $Zn^{2+}$, bis-L arginine salt of a metal ion selected from the group consisting of $Mg^{2+}$ and $Zn^{2+}$, and a complex of L arginine or bis-L arginine, a metal ion selected from the group consisting of $Mg^{2+}$ and $Zn^{2+}$, and an anion selected from the group consisting of hydroxide, halide, acetate, and ascorbate.

33. A method in accordance with claim 20 or 23 in which said L-carnitine is in the form of a member selected from the group consisting of L carnitine ascorbate, bis-L carnitine ascorbate, L carnitine salt of a metal ion selected from the group consisting of $Mg^{2+}$ and $Zn^{2+}$, bis-L carnitine salt of a metal ion selected from the group consisting of $Mg^{2+}$ and $Zn^{2+}$, and a complex of L carnitine or bis-L carnitine, a metal ion selected from the group consisting of $Mg^{2+}$ and $Zn^{2+}$, and an anion selected from the group consisting of hydroxide, halide, acetate, and ascorbate.

34. A method in accordance with claim 20 in which said L-taurine is in the form of a member selected from the group consisting of L taurine ascorbate, bis-L taurine ascorbate, L taurine salt of a metal ion selected from the group consisting of $Mg^{2+}$ and $Zn^{2+}$, bis-L taurine salt of a metal ion selected from the group consisting of $Mg^{2+}$ and $Zn^{2+}$, and a complex of L taurine or bis-L taurine, a metal ion selected from the group consisting of $Mg^{2+}$ and $Zn^{2+}$, and an anion selected from the group consisting of hydroxide, halide, acetate, and ascorbate.

35. A method in accordance with claim 20 or 23 in which said magnesium is in the form of a member selected from the group consisting of magnesium, magnesium L-arginate, magnesium L-arginine ascorbate and bis-ascorbate, magnesium α-lipoate, magnesium α-lipoate ascorbate and bis-ascorbate, magnesium taurate, magnesium taurine ascorbate and bis-ascorbate, magnesium L-acetylcysteine, magnesium L-carnitate, magnesium L-carnitine ascorbate and bis-ascorbate, magnesium ascorbate and magnesium bis-ascorbate.

36. A method in accordance with claim 26 in which said zinc is in the form of a member selected from the group consisting of zinc halide, zinc sulfate, zinc L-carnitate, zinc L-carnitate ascorbate and bis-ascorbate, zinc taurate, zinc taurine ascorbate and bis-ascorbate, zinc L-arginate, zinc L-arginine ascorbate and bis-ascorbate, zinc L-carnitate, zinc L-carnitine ascorbate and bis-ascorbate, zinc phosphate, zinc acetate, zinc ascorbate, and zinc bis-ascorbate.

37. A method in accordance with claim 26 in which said vanadium is in the form of a member selected from the group consisting of vanadate, peroxovanadate, vanadyl sulfate salts, and bis(maltolato)oxovanadium(IV).

38. A method in accordance with claim 30 in which said D,α tocopherol is present in the form of a member selected from the group consisting of D,α tocopherol succinate, D,α-tocopherol nicotinate, D,α-tocopherol picolinate, D,α tocopherol acetate, and tocotrienol.

39. A method in accordance with claim 38 in which said tocotrienol is present in the form of a member selected from the group consisting of tocotrienol succinate, tocotrienol nicotinate, tocotrienol picolinate, and tocotrienol acetate.

40. A method in accordance with claim 26 in which said chromium is in the form of a member selected from the group consisting of chromium dinicotinate, and chromium tripicolinate.

41. A method for treating a patient who is undergoing sulfonylurea therapy for the management, and clinical amelioration of insulin resistance and type 2 diabetes and conditions giving rise thereto, to reduce undesirable physiological side effects, and enhance the therapeutic effectiveness, of said sulfonylurea therapy, said method comprising administering to said patient a unit dosage form comprising as active ingredients:
   (a) L-carnitine,
   (b) Ascorbic acid,
   (c) Choline,
   (d) Taurine,
   (e) Folic Acid, and
   (f) Magnesium.

42. A method in accordance with claim 41 in which said active ingredients are formulated as a substantially homogeneous tablet or capsule that releases all of said active ingredients into the stomach upon ingestion for contact with gastric fluid.

43. A method in accordance with claim 42 in which:
   (a) said L-carnitine is in an amount ranging from about 90 mg to about 2500 mg, and
   (b) said ascorbic acid is in an amount ranging from about 75 mg to about 3000 mg,
   (c) said choline is in an amount ranging from about 15 mg to about 250 mg,
   (d) said taurine is in an amount ranging from about 75 mg to about 3000 mg,
   (e) said magnesium is in an amount ranging from about 30 mg to about 1000 mg, and
   (f) said folic acid is in an amount ranging from about 0.03 mg to about 2 mg.

44. A method for treating a patient who is undergoing nocturnal sulfonylurea therapy for the preservation of plasma and mitochondrial membrane integrity for the management, and clinical amelioration of insulin resistance and type 2 diabetes and conditions giving rise thereto, to reduce undesirable physiological side effects, and enhance the therapeutic effectiveness, of said sulfonylurea therapy, said method comprising administering to said patient a unit dosage form comprising as active ingredients:

(a) melatonin,
(b) L-Carnitine,
(c) ubiquinone,
(d) folic acid,
(e) magnesium, and
(f) L-arginine.

45. A method in accordance with claim 44 in which said active ingredients are formulated as a substantially homogeneous tablet or capsule that releases all of said active ingredients into the stomach upon ingestion for contact with gastric fluid.

46. A method in accordance with claim 45 in which:
(a) said melatonin is in an amount ranging from about 0.15 mg to about 7.5 mg,
(b) said L-carnitine is in an amount ranging from about 90 mg to about 2500 mg,
(c) said ubiquinone is in an amount ranging from about 4.5 mg to about 225 mg,
(d) said folic acid is in an amount ranging from about 0.03 mg to about 2 mg,
(e) said magnesium is in an amount ranging from about 30 mg to about 1000 mg, and
(f) said L-arginine is in an amount ranging from about 75 mg to about 3100 mg.

47. A method for treating a patient who is undergoing sulfonylurea therapy as an alternative to insulin for the management, and clinical amelioration of insulin resistance and type 2 diabetes and conditions giving rise thereto, to reduce undesirable physiological side effects, and enhance the therapeutic effectiveness, of said sulfonylurea therapy, said method comprising administering to said patient a unit dosage form comprising as active ingredients:
(a) vanadium,
(b) L-arginine,
(c) chromium, and
(d) zinc.

48. A method in accordance with claim 47 in which said active ingredients are formulated as a substantially homogeneous tablet or capsule that releases all of said active ingredients into the stomach upon ingestion for contact with gastric fluid.

49. A method in accordance with claim 48 in which:
(a) said vanadium is in an amount ranging from about 7.5 mg to about 375 mg,
(b) said L-arginine is in an amount ranging from about 75 mg to about 3100 mg,
(c) said chromium is in an amount ranging from about 0.01 mg to about 0.63 mg, and
(d) said zinc is in an amount ranging from about 1.5 mg to about 100 mg.

50. A method in accordance with claim 41 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| L, carnitine | 40–60% | balance |
| ascorbic acid | 40–60% | balance |
| choline | 100% |  |
| folic acid | 100% |  |
| taurine | 40–60% | balance |
| magnesium | 40–60% | balance |

51. A method in accordance with claim 44 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| melatonin | 40–60% | balance |
| L-carnitine | 40–60% | balance |
| zinc | 40%–60% | balance |
| folic acid | 100% |  |
| magnesium | 40–60% | balance |
| ubiquinone | 100% |  |

52. A method in accordance with claim 47 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| vanadium | 40–60% | balance |
| L-arginine | 40–60% | balance |
| chromium | 40%–60% | balance |
| zinc | 40%–60% | balance |

53. A method in accordance with claim 44, or 47 in which said L-arginine is in the form of a member selected from the group consisting of L arginine ascorbate, bis-L arginine ascorbate, L arginine salt of a metal ion selected from the group consisting of $Mg^{2+}$ and $Zn^{2+}$, bis-L arginine salt of a metal ion selected from the group consisting of $Mg^{2+}$ and $Zn^{2+}$, and a complex of L arginine or bis-L arginine, a metal ion selected from the group consisting of $Mg^{2+}$ and $Zn^{2+}$, and an anion selected from the group consisting of hydroxide, halide, acetate, and ascorbate.

54. A method in accordance with claim 41 or 44 in which said L-carnitine is in the form of a member selected from the group consisting of L carnitine ascorbate, bis-L carnitine ascorbate, L carnitine salt of a metal ion selected from the group consisting of $Mg^{2+}$ and $Zn^{2+}$, bis-L carnitine salt of a metal ion selected from the group consisting of $Mg^{2+}$ and $Zn^{2+}$, and a complex of L carnitine or bis-L carnitine, a metal ion selected from the group consisting of $Mg^{2+}$ and $Zn^{2+}$, and an anion selected from the group consisting of hydroxide, halide, acetate, and ascorbate.

55. A method in accordance with claim 41 in which said L-taurine is in the form of a member selected from the group consisting of L taurine ascorbate, bis-L taurine ascorbate, L taurine salt of a metal ion selected from the group consisting of $Mg^{2+}$ and $Zn^{2+}$, bis-L taurine salt of a metal ion selected from the group consisting of $Mg^{2+}$ and $Zn^{2+}$, and a complex of L taurine or bis-L taurine, a metal ion selected from the group consisting of $Mg^{2+}$ and $Zn^{2+}$, and an anion selected from the group consisting of hydroxide, halide, acetate, and ascorbate.

56. A method in accordance with claim 41 or 44 in which said magnesium is in the form of a member selected from the group consisting of magnesium, magnesium L-arginate, magnesium L-arginine ascorbate and bis-ascorbate, magnesium α-lipoate, magnesium α-lipoate ascorbate and bis-ascorbate, magnesium taurate, magnesium taurine ascorbate and bis-ascorbate, magnesium L-acetylcysteine, magnesium L-carnitate, magnesium L-carnitine ascorbate and bis-ascorbate, magnesium ascorbate and magnesium bis-ascorbate.

57. A method in accordance with claim 47 in which said zinc is in the form of a member selected from the group consisting of zinc halide, zinc sulfate, zinc L-carnitate, zinc L-carnitate ascorbate and bis-ascorbate, zinc taurate, zinc taurine ascorbate and bis-ascorbate, zinc L-arginate, zinc L-arginine ascorbate and bis-ascorbate, zinc L-carnitate, zinc L-carnitine ascorbate and bis-ascorbate, zinc phosphate, zinc acetate, zinc ascorbate, and zinc bis-ascorbate.

58. A method in accordance with claim 47 in which said vanadium is in the form of a member selected from the group consisting of vanadate, peroxovanadate, vanadyl sulfate salts, and bis(maltolato)oxovanadium(IV).

59. A method in accordance with claim 26 in which said chromium is in the form of a member selected from the group consisting of chromium dinicotinate, and chromium tripicolinate.

60. A method for treating a patient who is undergoing combined biguanide and combined biguanide and sulfonylurea therapy for the management, and clinical amelioration of insulin resistance and type 2 diabetes and conditions giving rise thereto, to reduce undesirable physiological side effects, and enhance the therapeutic effectiveness, of said combined biguanide and sulfonylurea therapy, said method comprising administering to said patient a unit dosage form comprising as active ingredients:
    (a) L-carnitine,
    (b) ascorbic acid,
    (c) choline,
    (e) taurine,
    (f) folic acid, and
    (g) magnesium.

61. A method in accordance with claim 60 in which said active ingredients are formulated as a substantially homogeneous tablet or capsule that releases all of said active ingredients into the stomach upon ingestion for contact with gastric fluid.

62. A method in accordance with claim (61 in which:
    (a) said L-carnitine is in an amount ranging from about 90 mg to about 2500 mg, and
    (b) said ascorbic acid is in an amount ranging from about 75 mg to about 3000 mg,
    (c) said choline is in an amount ranging from about 15 mg to about 250 mg,
    (d) said taurine is in an amount ranging from about 75 mg to about 3000 mg,
    (e) said magnesium is in an amount ranging from about 30 mg to about 1000 mg, and
    (d) said folic acid is in an amount ranging from about 0.03 mg to about 2 mg.

63. A method for treating a patient who is undergoing nocturnal combined biguanide and sulfonylurea therapy for the preservation of plasma and mitochondrial membrane integrity for the management, and clinical amelioration of insulin resistance and type 2 diabetes and conditions giving rise thereto, to reduce undesirable physiological side effects, and enhance the therapeutic effectiveness, of said combined biguanide and sulfonylurea therapy, said method comprising administering to said patient a unit dosage form comprising as active ingredients:
    (a) melatonin,
    (b) L-Carnitine,
    (c) ubiquinone,
    (d) folic acid,
    (e) magnesium, and
    (f) L-arginine.

64. A method in accordance with claim 63 in which said active ingredients are formulated as a substantially homogeneous tablet or capsule that releases all of said active ingredients into the stomach upon ingestion for contact with gastric fluid.

65. A method in accordance with claim 64 in which:
    (a) said melatonin is in an amount ranging from about 0.15 mg to about 7.5 mg,
    (b) said L-carnitine is in an amount ranging from about 90 mg to about 2500 mg,
    (c) said ubiquinone is in an amount ranging from about 4.5 mg to about 225 mg,
    (d) said folic acid is in an amount ranging from about 0.03 mg to about 2 mg,
    (e) said magnesium is in an amount ranging from about 30 mg to about 1000 mg, and
    (f) said L-arginine is in an amount ranging from about 75 mg to about 3100 mg.

66. A method for treating a patient who is undergoing combined biguanide and sulfonylurea therapy as an alternative to insulin for the management, and clinical amelioration of insulin resistance and type 2 diabetes and conditions giving rise thereto, to reduce undesirable physiological side effects, and enhance the therapeutic effectiveness, of said combined biguanide and sulfonylurea therapy, said method comprising administering to said patient a unit dosage form comprising as active ingredients:
    (a) vanadium,
    (b) L-arginine,
    (c) chromium, and
    (d) zinc.

67. A method in accordance with claim 66 in which said active ingredients are formulated as a substantially homogeneous tablet or capsule that releases all of said active ingredients into the stomach upon ingestion for contact with gastric fluid.

68. A method in accordance with claim 67 in which:
    (a) said vanadium is in an amount ranging from about 7.5 mg to about 375 mg,
    (b) said L-arginine is in an amount ranging from about 75 mg to about 3100 mg,
    (c) said chromium is in an amount ranging from about 0.01 mg to about 0.63 mg, and
    (d) said zinc is in an amount ranging from about 1.5 mg to about 100 mg.

69. A method in accordance with claim 67 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
| --- | --- | --- |
| L, carnitine | 40–60% | balance |
| ascorbic acid | 40–60% | balance |
| choline | 100% |  |
| folic acid | 100% |  |

-continued

|  | Immediate-Release Layer | Sustained-Release Layer |
|---|---|---|
| taurine | 40–60% | balance |
| magnesium | 40–60% | balance |

70. A method in accordance with claim 63 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
|---|---|---|
| melatonin | 40–60% | balance |
| L-carnitine | 40–60% | balance |
| zinc | 40%–60% | balance |
| folic acid | 100% |  |
| magnesium | 40–60% | balance |
| ubiquinone | 100% |  |

71. A method in accordance with claim 66 in which said unit dosage form is a bilayer tablet comprising an immediate-release layer and a sustained-release layer, said active ingredients are distributed between said immediate-release layer and said sustained-release layer in the following approximate proportions expressed as relative weight percents:

|  | Immediate-Release Layer | Sustained-Release Layer |
|---|---|---|
| vanadium | 40–60% | balance |
| L-arginine | 40–60% | balance |
| chromium | 40%–60% | balance |
| zinc | 40%–60% | balance |

72. A method in accordance with claim 63, or 66 in which said L-arginine is in the form of a member selected from the group consisting of L arginine ascorbate, bis-L arginine ascorbate, L arginine salt of a metal ion selected from the group consisting of $Mg^{2+}$ and $Zn^{2+}$, bis-L arginine salt of a metal ion selected from the group consisting of $Mg^{2+}$ and $Zn^{2+}$, and a complex of L arginine or bis-L arginine, a metal ion selected from the group consisting of $Mg^{2+}$ and $Zn^{2+}$, and an anion selected from the group consisting of hydroxide, halide, acetate, and ascorbate.

73. A method in accordance with claim 59 or 63 in which said L-carnitine is in the form of a member selected from the group consisting of L carnitine ascorbate, bis-L carnitine ascorbate, L carnitine salt of a metal ion selected from the group consisting of $Mg^{2+}$ and $Zn^{2+}$, bis-L carnitine salt of a metal ion selected from the group consisting of $Mg^{2+}$ and $Zn^{2+}$, and a complex of L carnitine or bis-L carnitine, a metal ion selected from the group consisting of $Mg^{2+}$ and $Zn^{2+}$, and an anion selected from the group consisting of hydroxide, halide, acetate, and ascorbate.

74. A method in accordance with claim 59 in which said L-taurine is in the form of a member selected from the group consisting of L taurine ascorbate, bis-L taurine ascorbate, L taurine salt of a metal ion selected from the group consisting of $Mg^{2+}$ and $Zn^{2+}$, bis-L taurine salt of a metal ion selected from the group consisting of $Mg^{2+}$ and $Zn^{2+}$, and a complex of L taurine or bis-L taurine, a metal ion selected from the group consisting of $Mg^{2+}$ and $Zn^{2+}$, and an anion selected from the group consisting of hydroxide, halide, acetate, and ascorbate.

75. A method in accordance with claim 60 or 63 in which said magnesium is in the form of a member selected from the group consisting of magnesium, magnesium L-arginate, magnesium L-arginine ascorbate and bis-ascorbate, magnesium α-lipoate, magnesium α-lipoate ascorbate and bis-ascorbate, magnesium taurate, magnesium taurine ascorbate and bis-ascorbate, magnesium L-acetylcysteine, magnesium L-carnitate, magnesium L-carnitine ascorbate and bis-ascorbate, magnesium ascorbate and magnesium bis-ascorbate.

76. A method in accordance with claim 66 in which said zinc is in the form of a member selected from the group consisting of zinc halide, zinc sulfate, zinc L-carnitate, zinc L-carnitate ascorbate and bis-ascorbate, zinc taurate, zinc taurine ascorbate and bis-ascorbate, zinc L-arginate, zinc L-arginine ascorbate and bis-ascorbate, zinc L-carnitate, zinc L-carnitine ascorbate and bis-ascorbate, zinc phosphate, zinc acetate, zinc ascorbate, and zinc bis-ascorbate.

77. A method in accordance with claim 66 in which said vanadium is in the form of a member selected from the group consisting of vanadate, peroxovanadate, vanadyl sulfate salts, and bis(maltolato)oxovanadium(IV).

78. A method in accordance with claim 66 in which said chromium is in the form of a member selected from the group consisting of chromium dinicotinate, and chromium tripicolinate.

* * * * *